US009771391B2

(12) United States Patent
Vlahov et al.

(10) Patent No.: US 9,771,391 B2
(45) Date of Patent: Sep. 26, 2017

(54) PROCESS FOR PREPARING TUBULYSINS

(71) Applicant: ENDOCYTE, INC., West Lafayette, IN (US)

(72) Inventors: Iontcho Radoslavov Vlahov, West Lafayette, IN (US); Christopher Paul Leamon, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 0 days.

(21) Appl. No.: 14/771,532

(22) PCT Filed: Feb. 28, 2014

(86) PCT No.: PCT/US2014/019605
§ 371 (c)(1),
(2) Date: Aug. 31, 2015

(87) PCT Pub. No.: WO2014/134543
PCT Pub. Date: Sep. 4, 2014

(65) Prior Publication Data
US 2016/0016993 A1 Jan. 21, 2016

Related U.S. Application Data

(60) Provisional application No. 61/771,429, filed on Mar. 1, 2013, provisional application No. 61/793,082, filed on Mar. 15, 2013.

(51) Int. Cl.
C07K 5/00 (2006.01)
C07K 5/02 (2006.01)
C07K 5/062 (2006.01)
C07D 417/14 (2006.01)
C07D 417/12 (2006.01)
C07K 5/097 (2006.01)

(52) U.S. Cl.
CPC .......... C07K 5/0606 (2013.01); C07D 417/12 (2013.01); C07D 417/14 (2013.01); C07K 5/0821 (2013.01)

(58) Field of Classification Search
None
See application file for complete search history.

(56) References Cited

U.S. PATENT DOCUMENTS

| | | | |
|---|---|---|---|
| 5,627,165 A | 5/1997 | Glazier | |
| 7,601,332 B2 | 10/2009 | Vlahov et al. | |
| 7,754,885 B2 | 7/2010 | Hoefle et al. | |
| 7,776,814 B2 | 8/2010 | Dömling et al. | |
| 7,816,377 B2 | 10/2010 | Domling et al. | |
| 8,889,880 B2 | 11/2014 | Vlahov et al. | |
| 9,187,521 B2* | 11/2015 | Vlahov | C07K 5/06139 |
| 9,273,091 B2 | 3/2016 | Vlahov et al. | |
| 9,499,849 B2 | 11/2016 | Vlahov et al. | |
| 9,505,747 B2* | 11/2016 | Vlahov | C07K 5/02 |

| | | |
|---|---|---|
| 2006/0128754 A1 | 6/2006 | Hoefle et al. |
| 2010/0240701 A1 | 9/2010 | Vlahov et al. |
| 2011/0027274 A1 | 2/2011 | Cheng et al. |
| 2011/0263650 A1 | 10/2011 | Ellman et al. |

FOREIGN PATENT DOCUMENTS

| | | |
|---|---|---|
| WO | 2008/112873 | 11/2008 |
| WO | WO2009/055562 | 4/2009 |
| WO | 2011/069116 | 6/2011 |
| WO | 2011/006639 | 11/2011 |
| WO | 2012/019123 | 2/2012 |
| WO | WO2012/019123 | 2/2012 |
| WO | WO2013/149185 | 10/2013 |

OTHER PUBLICATIONS

Peltier, JACS, 2006, 128, 16018-16019 (cited in prosecution of related applications).*
Vlahov, Bioorganic & Medicinal Chemistry Letters 21 (2011) 6778-6781.*
Shibue, 2010, Chem. Eur. J., 16, 11678-11688.*
Peltier, 2006, JACS, 128, 16018-16019.*
Pando, 2009, Organic Letters, 11, 5567-5569.*
PCT Search Report and Written Opinion for PCT/US2014/019605, completed Jun. 30, 2014.
Wang, Zhiyong, et al. "Structure-activity and High-content Imaging Analyses of Novel Tubulysins," Chemical Biology & Drug Design 70(2): 75-86, (2007).
Patterson, Andrew W., et al. "Design, synthesis, and biological properties of highly potent tubulysin D analogues," Chemistry—A European Journal 13(34): 9534-9541, (2007).
Steinmetz, Heinrich, et al. "Isolation, crystal and solution structure determination, and biosynthesis of tubulysins—powerful inhibitors of tubulin polymerization from myxobacteria," Angewandte Chemie International Edition 43(37): 4888-4892, (2004).
March, Jerry. Advanced organic chemistry: reactions, mechanisms, and structure. vol. 4. New York: McGraw-Hill, 1968, p. 362-363, 816, 885, 896.
Lopes, Francisca, Rui Moreira, and Jim Iley. "Acyloxymethyl as a drug protecting group. Part 5.1 Kinetics and mechanism of the hydrolysis of tertiary N-acyloxymethylsulfonamides," J. Chem. Soc., Perkin Trans. 2, vol. 3: 431-440, (1999).
Churlaud, Carine, et al., "Novel 4-(Trimethylsilyl)aminoalkanes and 4-(Trimethylsilyl)aminoalk-2-enes, via a 1,5-Hydride Shift, in the Reaction of r-Unsaturated Silanes with Aminomethylbenzotriazoles," Organometallics, 18(21): 4270-4274.
Peltier, Hillary M., et al. "The total synthesis of tubulysin D," Journal of the American Chemical Society 128(50): 16018-16019 (2006).

(Continued)

Primary Examiner — Satyanarayana R Gudibande
(74) Attorney, Agent, or Firm — Barnes & Thornburg LLP

(57) ABSTRACT

The invention described herein pertains to processes for preparing tubulysins and derivatives thereof. The invention described herein also pertains to processes for preparing tubulysin conjugates. The invention described herein also pertains to processes for preparing intermediates for preparing tubulysin conjugates. In one step, the alpha-thiazolyl alcohol is protected with triethylsilyl chloride in the presence of imidazole in an aprotic solvent.

16 Claims, No Drawings

(56) References Cited

OTHER PUBLICATIONS

Wu, Shih Hsiung, Zhi Wei Guo, and Charles J. Sih. "Enhancing the enantioselectivity of Candida lipase-catalyzed ester hydrolysis via noncovalent enzyme modification," Journal of the American Chemical Society 112(5) (1990).
Sasse, F., et al. "Tubulysins, new cytostatic peptides from myxobacteria acting on microtubuli. Production, isolation, physicochemical and biological properties," J Antibiot 53:879-885 (2000).
Kaur, G., et al., "Biological evaluation of tubulysin A: a potential anticancer and antiangiogenic natural product," Biochem. J. 396, 235-242, (2006).
Domling, A., et al., "Myxobacterial epothilones and tubulysins as promising anticancer agents," Mol. Diversity, 9:141-147, (2005).
Pando, O., et al, "First Total Synthesis of Tubulysin B." Org. Lett., 11(24): 5567-5569, (2009).
G. Hofle, G., et al., "Semisynthesis and degradation of the tubulin inhibitors epothilone and tubulysin," Pure Appi. Chem. 75:167-178, (2003).
Rose, "Taxol-based combination chemotherapy and other in vivo preclinical antitumor studies," J Natl Cancer Inst Monogr, 15:47-53 (1993).
Lee et al., "BMS-247550: a novel epothilone analog with a mode of action similar to paclitaxel but possessing superior antitumor efficacy," Clin Cancer Res 7:1429-1437 (2001).
PCT Search Report and Written Opinion for PCT/US2011/046797, completed Dec. 23, 2011.
Speckamp, et al., "New Developments in the Chemistry of N-Acyliminium Ions and Related Intermediates," Tetrahedron 56(24):3817-3856 (2000).
European Search Report prepared for corresponding European Application Serial No. 08841521.1, mailed Jul. 18, 2011.
Raghavan, Bhooma, et al. "Cytotoxic Simplified Tubulysin Analogues," J. Med. Chem. 51:1530-1533 (2008).
PCT Search Report and Written Opinion for PCT/EP2003/011603, completed Feb. 11, 2011.
Patterson, Andrew W., Hillary M. Peltier, and Jonathan A. Ellman. "Expedient synthesis of N-methyl tubulysin analogues with high cytotoxicity," The Journal of Organic Chemistry, 73(12): 4362-4369 (2008).
Kularatne, S., "Synthesis and Biological Analysis of Prostate-Specific Membrane Antigen-Targeted Anticancer Prodrugs," J. Med. Chem, 2010, 53(21), 7767-7777.
Vlahov, I. et al., "Design and regioselective synthesis of a new generation of targeted chemotherapeutics. Part II: Folic acid conjugates of tubulysins and their hydrazides," Bioorg. Med. Chem. Lett., 2008, 18(16), 4558-4561.

* cited by examiner

PROCESS FOR PREPARING TUBULYSINS

CROSS REFERENCE TO RELATED APPLICATIONS

This application is a U.S. national stage application under 35 U.S.C. §371(b) of International Application No. PCT/US2014/019605 filed Feb. 28, 2014, and claims priority under 35 U.S.C. §119(e) to U.S. Provisional Application Ser. No. 61/771,429, filed Mar. 1, 2013 and U.S. Provisional Application Ser. No. 61/793,082, filed Mar. 15, 2013, in which all of which are incorporated herein by reference in their entirety.

TECHNICAL FIELD

The invention described herein pertains to processes for preparing tubulysins and derivatives thereof. The invention described herein also pertains to processes for preparing tubulysin conjugates. The invention described herein also pertains to processes for preparing intermediates for preparing tubulysin conjugates.

BACKGROUND AND SUMMARY OF THE INVENTION

Tubulysins are members of a new class of natural products isolated from myxobacterial species (F. Sasse, et al., *J. Antibiot.* 2000, 53, 879-885). As cytoskeleton interacting agents, the tubulysins are mitotic poisons that inhibit tubulin polymerization and lead to cell cycle arrest and apoptosis (H. Steinmetz, et al., *Chem. Int. Ed.* 2004, 43, 4888-4892; M. Khalil, et al., *ChemBioChem.* 2006, 7, 678-683; G. Kaur, et al., *Biochem. J.* 2006, 396, 235-242). Tubulysins are extremely potent cytotoxic molecules, exceeding the cell growth inhibition of any clinically relevant traditional chemotherapeutic, including epothilones, paclitaxel, and vinblastine. Furthermore, tubulysins are potent against multidrug resistant cell lines (A. Dömling, et al., *Mol. Diversity* 2005, 9, 141-147). These compounds show high cytotoxicity tested against a panel of cancer cell lines with $IC_{50}$ values in the low picomolar range; thus, they are of interest as potential anticancer therapeutics.

Tubulysins and processes for preparing tubulysins are described herein. In one embodiment, tubulysins and processes for preparing them are described herein that include linear tetrapeptoid backbones, including illustrative compounds having formula T or TE

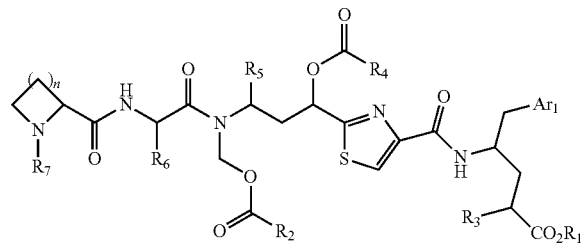
(T)

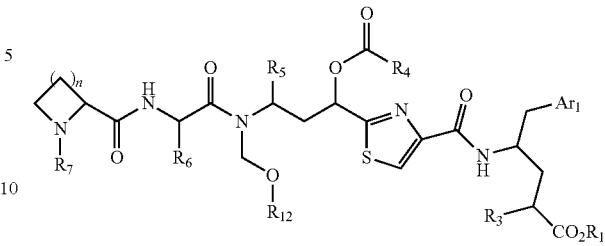
(TE)

and pharmaceutically acceptable salts thereof; wherein $Ar_1$ is optionally substituted aryl or optionally substituted heteroaryl;

$R_1$ is hydrogen, optionally substituted alkyl, optionally substituted arylalkyl or a pro-drug forming group;

$R_2$ is selected from the group consisting of optionally substituted alkyl, optionally substituted cycloalkyl, optionally substituted arylalkyl, and optionally substituted heteroarylalkyl;

$R_{12}$ is alkyl, alkenyl, alkynyl, heteroalkyl, cycloalkyl, heterocycloalkyl, aryl, heteroaryl, arylalkyl or heteroarylalkyl, each of which is optionally substituted;

$R_3$ is optionally substituted alkyl;

$R_4$ is optionally substituted alkyl or optionally substituted cycloalkyl;

$R_5$ and $R_6$ are each independently selected from the group consisting of optionally substituted alkyl and optionally substituted cycloalkyl;

$R_7$ is hydrogen or optionally substituted alkyl; and n is 1, 2, 3, or 4.

In another embodiment, tubulysin amide and hydrazide derivatives, and processes for preparing them are described herein, such as compounds of the following formulae

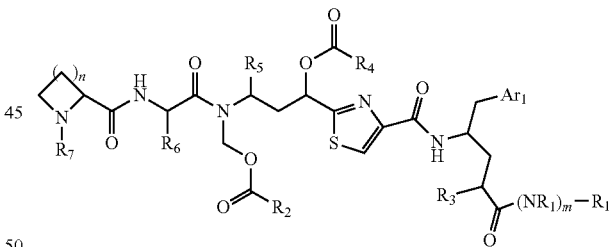

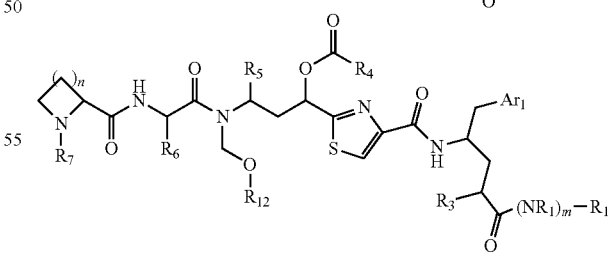

and pharmaceutically acceptable salts thereof; wherein $R_1$, $R_2$, $R_{12}$, $R_3$, $R_4$, $R_5$, $R_6$, $R_7$, and n are each independently selected from any of the various embodiments described herein; and m is 1 or 2.

In another embodiment, tubulysins and processes for preparing them are described herein that comprise one or more radicals formed from N-methyl pipecolic acid (Mep), isoleucine (Ile), and/or one or more non-naturally occurring or hydrophobic amino acid segments, such as

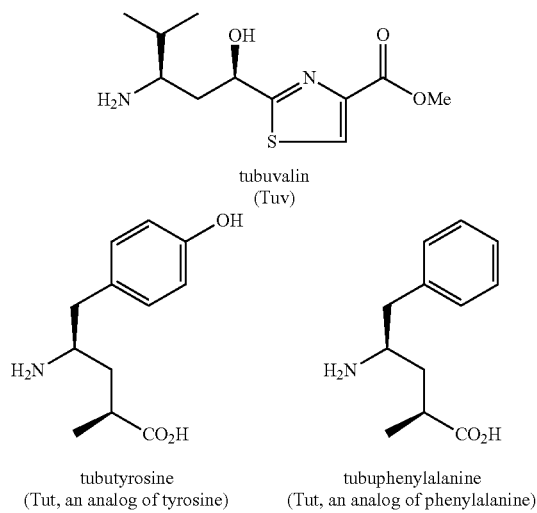

and analogs and derivatives of each of the foregoing. Without being bound by theory, it is believed herein that a common feature in the molecular architecture of the more potent natural occurring tubulysins is the acid and/or base sensitive N-acyloxymethyl substituent (or a N,O-acetal of formaldehyde) represented by $R_2$—C(O) in the formula (T).

In another embodiment, tubulysins and processes for preparing them are described herein that have formula 1, and are naturally occurring.

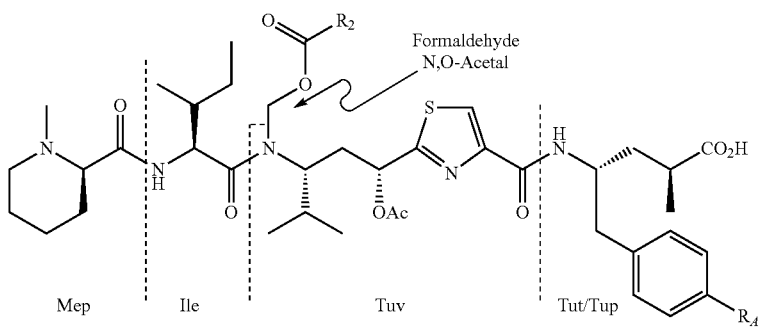

Formula 1, Structures of several natural tubulysins

| Tubulysin | $R_A$ | $R_2$ |
|---|---|---|
| A | OH | $CH_2CH(CH_3)_2$ |
| B | OH | $CH_2CH_2CH_3$ |
| C | OH | $CH_2CH_3$ |
| D | H | $CH_2CH(CH_3)_2$ |
| E | H | $CH_2CH_2CH_3$ |
| F | H | $CH_2CH_3$ |
| G | OH | $CH=C(CH_3)_2$ |
| H | H | $CH_3$ |
| I | OH | $CH_3$ |

A total synthesis of tubulysin D has been reported (see, Peltier et al., J Am Chem Soc 128:16018-19 (2006)). Recently, a modified synthetic protocol toward the synthesis of tubulysin B has been reported (Pando et at., Org Lett 11:5567-69 (2009)). However, attempts to follow the published procedures to provide larger quantities of tubulysins were unsuccessful, and were hampered by low yields, difficult to remove impurities, the need for expensive chromatographic steps, and/or the lack of reproducibility of several steps, among other things. The interest in using tubulysins for anticancer therapeutics accents the need for reliable and efficient processes for preparing tubulysins, and analogs and derivatives thereof. Described herein are improved processes for making tubulysins, or analogs or derivatives thereof, including compounds of formula T and TE.

In one illustrative embodiment of the invention, processes for preparing tubulysins, or analogs or derivatives thereof, including compounds of formula T and TE, are described. The processes include one or more steps in the following embodiments.

In another embodiment, a process is described for preparing a compound of formula B, wherein $R_5$ and $R_6$ are independently selected from any of the various embodiments described herein, and $R_8$ is $C_1$-$C_6$ n-alkyl or arylalkyl, such as benzyl. The process comprises the step of treating a compound of formula A with a silylating agent, such as triethylsilyl chloride, and a base, such as imidazole in an aprotic solvent.

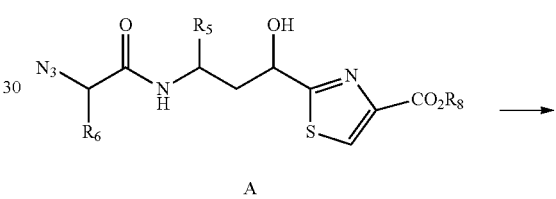

A

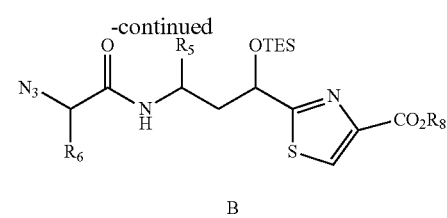

B

In another embodiment, a process is described for preparing a compound of formula C, wherein $R_2$, $R_5$, $R_6$, and $R_8$ are each independently selected from any of the various embodiments described herein. The process comprises the step of treating a compound of formula B with a base and a compound of the formula $ClCH_2OC(O)R_2$ in an aprotic solvent at a temperature below ambient temperature, such as in the range from about −78° C. to about 0° C.; wherein the molar ratio of the compound of the formula ClCH$_2$OC(O)R$_2$ to the compound of formula B from about 1 to about 1.5.

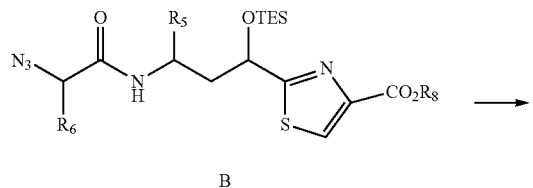

B

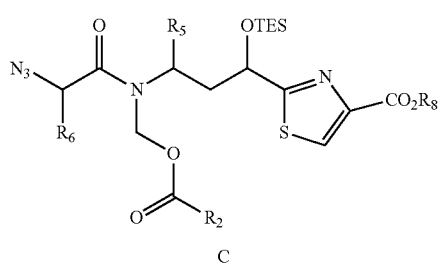

C

In another embodiment, a process is described for preparing a compound of formula D, wherein n, R$_2$, R$_5$, R$_6$, and R$_8$ are each independently selected from any of the various embodiments described herein, and R$_7$ is optionally substituted alkyl. The process comprises the steps of a) preparing a compound of formula (E1) where X$_1$ is a leaving group or acyl activating group from a compound of formula E; and b) treating a compound of formula C under reducing conditions in the presence of the compound of formula E1.

In another embodiment, a process is described for preparing a compound of formula FE, wherein n, R$_2$, R$_5$, R$_6$, R$_7$, and R$_8$ are each independently selected from any of the various embodiments described herein. The process comprises the step of contacting compound D with an alcohol, R$_{12}$OH, where R$_{12}$ is alkyl, alkenyl, alkynyl, heteroalkyl, cycloalkyl, heterocycloalkyl, aryl, arylalkyl or heteroarylalkyl, each of which is optionally substituted; and a transesterification catalyst. In one embodiment the transesterification catalyst is trifluoroacetic acid (TFA). In another embodiment, the transesterification catalyst is selected from the group consisting of (R$_{13}$)$_8$Sn$_4$O$_2$(NCS)$_4$, (R$_{13}$)$_2$Sn(OAc)$_2$, (R$_{13}$)$_2$SnO, (R$_{13}$)$_2$SnCl$_2$, (R$_{13}$)$_2$SnS, (R$_{13}$)$_3$SnOH, and (R$_{13}$)$_3$SnOSn(R$_{13}$)$_3$, where R$_{13}$ is independently selected from alkyl, arylalkyl, aryl, or cycloalkyl, each of which is optionally substituted. In another embodiment, the transesterification catalyst is (R$_{13}$)$_2$SnO. Illustrative examples of R$_{13}$ are methyl, n-butyl, n-octyl, phenyl, o-MeO-phenyl, p-MeO-phenyl, phenethyl, benzyl, and the like.

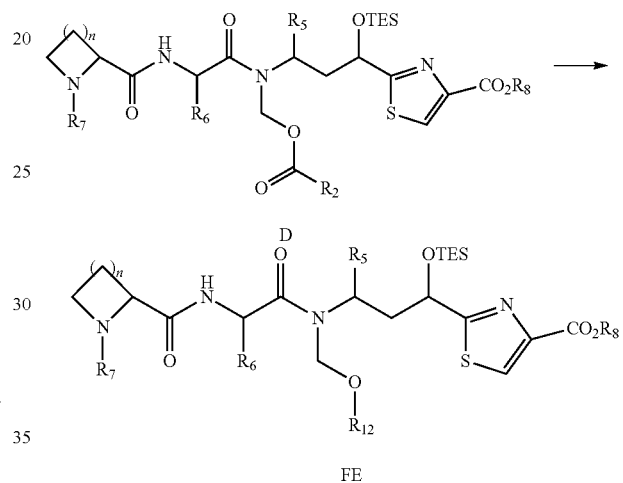

FE

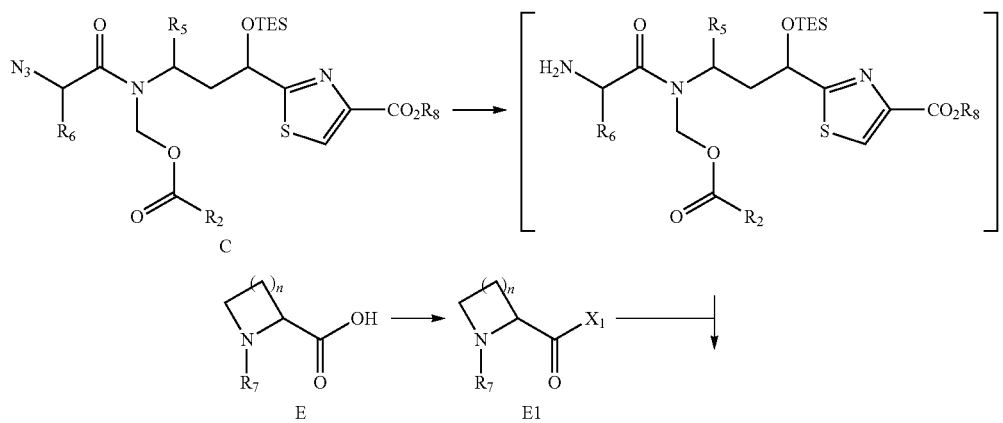

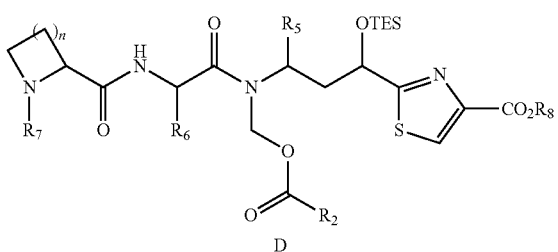

D

In another embodiment, a process is described for preparing a compound of formula IE, wherein n, $R_5$, $R_6$, $R_7$, and $R_{12}$ are each independently selected from any of the various embodiments described herein. The process comprises the step of contacting compound FE with a metal hydroxide or carbonate. Illustrative examples of a metal hydroxide or carbonate include LiOH, $Li_2CO_3$, NaOH, $Na_2CO_3$, KOH, $K_2CO_3$, $Ca(OH)_2$, $CaCO_3$, $Mg(OH)_2$, $MgCO_3$, and the like.

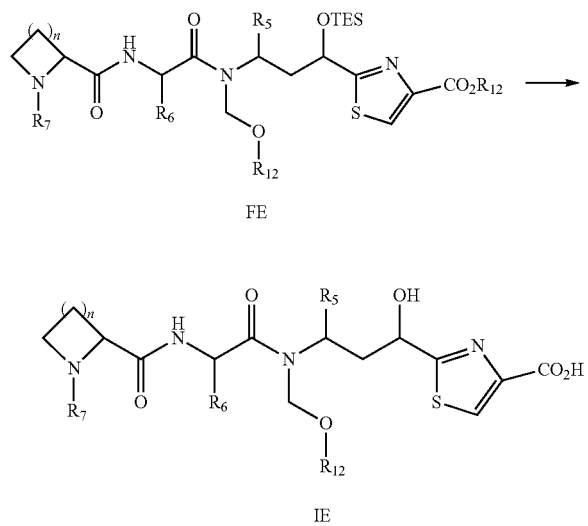

FE

IE

In another embodiment, a process is described for preparing a compound of formula G, wherein n, $R_2$, $R_5$, $R_6$, $R_7$, and $R_8$ are each independently selected from any of the various embodiments described herein. The process comprises the step of treating compound D with a hydrolase enzyme.

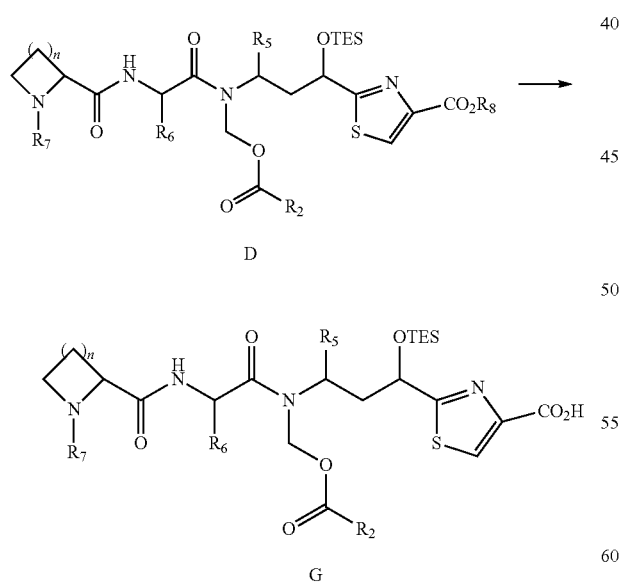

D

G

In another embodiment, a process is described for preparing a compound of formula I, wherein n, $R_2$, $R_5$, $R_6$, and $R_7$ are each independently selected from any of the various embodiments described herein. The process comprises the step of treating the silyl ether of compound G with a non-basic fluoride containing reagent.

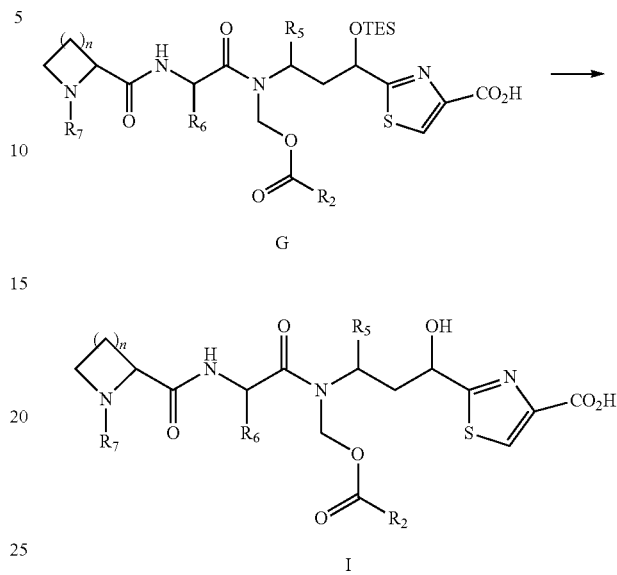

G

I

In another embodiment, a process is described for preparing a compound of formula GE, wherein n, $R_2$, $R_5$, $R_6$, and $R_7$ are each independently selected from any of the various embodiments described herein. The process comprises the step of contacting compound G with an alcohol, $R_{12}OH$, and a transesterification catalyst, as described herein.

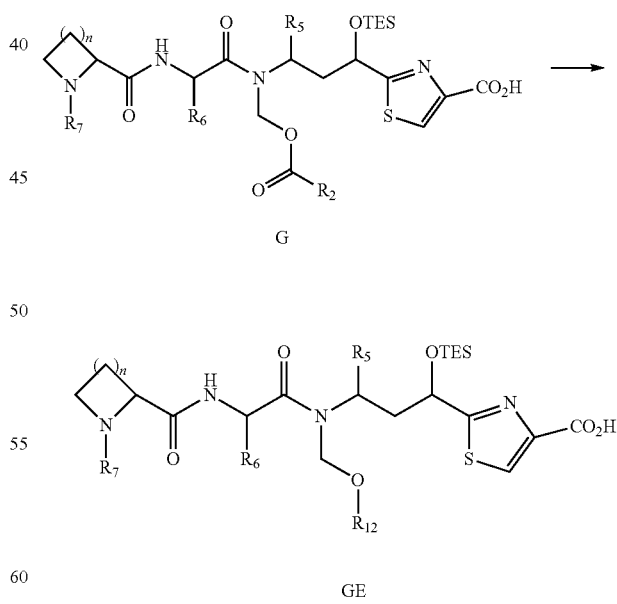

G

GE

In another embodiment, a process is described for preparing a compound of formula IE, wherein n, $R_5$, $R_6$, $R_7$, and $R_{12}$ are each independently selected from any of the various embodiments described herein. The process comprises the step of treating the silyl ether of compound GE with a non-basic fluoride containing reagent.

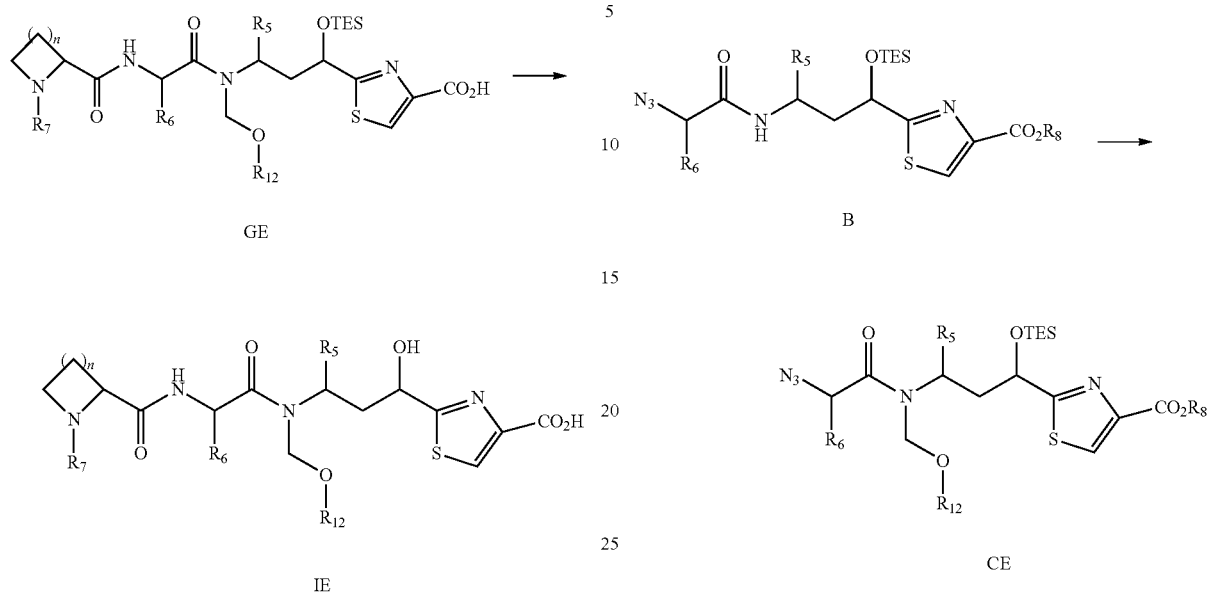

In another embodiment, a process is described for preparing a compound of formula CE, wherein $R_5$, $R_{12}$, $R_6$, and $R_8$ are each independently selected from any of the various embodiments described herein. The process comprises the step of treating a compound of formula B with a base and a compound of the formula $YCH_2OR_{12}$, where Y is a leaving group such as a halogen selected from chloro, bromo, and iodo, in an aprotic solvent at a temperature below ambient temperature, such as in the range from about −78° C. to about 0° C.; wherein the molar ratio of the compound of the formula $YCH_2OR_{12}$ to the compound of formula B from about 1 to about 1.3.

In another embodiment, a process is described for preparing a compound of formula DE, wherein n, $R_{12}$, $R_5$, $R_6$, and $R_8$ are each independently selected from any of the various embodiments described herein, and $R_7$ is optionally substituted alkyl. The process comprises the steps of a) preparing a compound of formula (E1) where $X_1$ is a leaving group or acyl activating group from a compound of formula E; and b) treating a compound of formula CE under reducing conditions in the presence of the compound of formula E1.

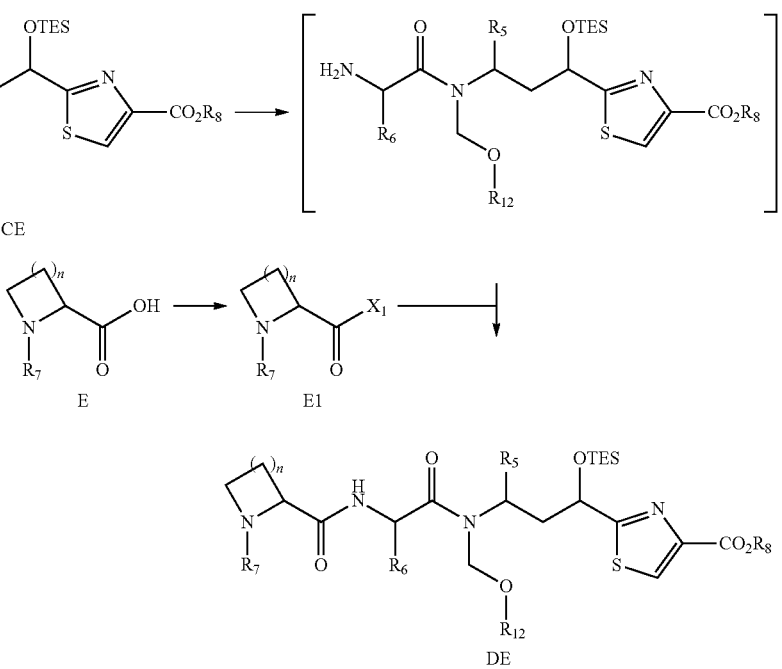

In another embodiment, a process is described for preparing a compound of formula IE, wherein n, $R_{12}$, $R_5$, $R_6$, $R_7$, and $R_8$ are each independently selected from any of the various embodiments described herein. The process comprises the step of treating the silyl ether/ester of compound DE with a base.

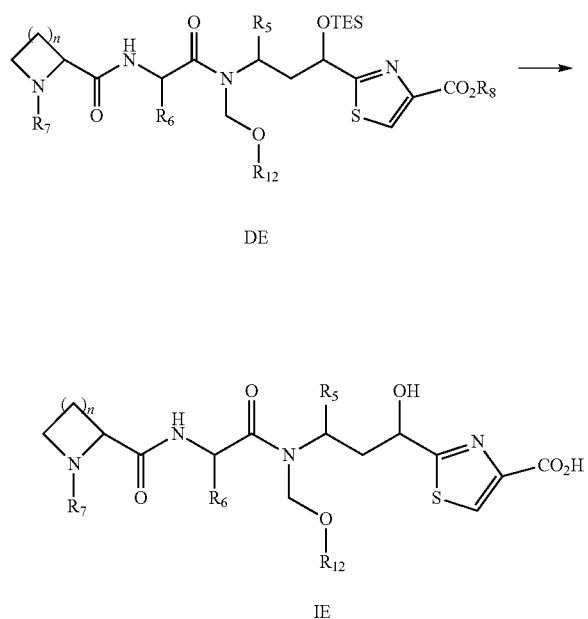

DE

IE

In another embodiment, a process is described for preparing a compound of formula JE, wherein n, $R_{12}$, $R_4$, $R_5$, $R_6$, and $R_7$ are each independently selected from any of the various embodiments described herein. The process comprises the step of treating a compound of formula IE with an acylating agent of formula $R_4C(O)X_2$, where $X_2$ is a leaving group.

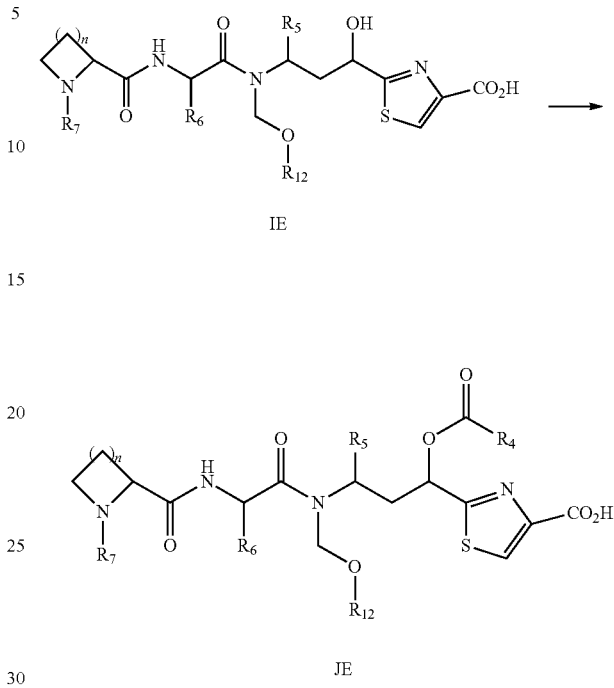

IE

JE

In another embodiment, a process is described for preparing a tubulysin of formula (TE), wherein n, $Ar_1$, $R_1$, $R_3$, $R_4$, $R_5$, $R_6$, $R_7$, and $R_{12}$ are each independently selected from any of the various embodiments described herein. The process comprises the step of forming an active ester intermediate from a compound of formula JE; and reacting the active ester intermediate with a compound of the formula M to give a compound of the formula TE.

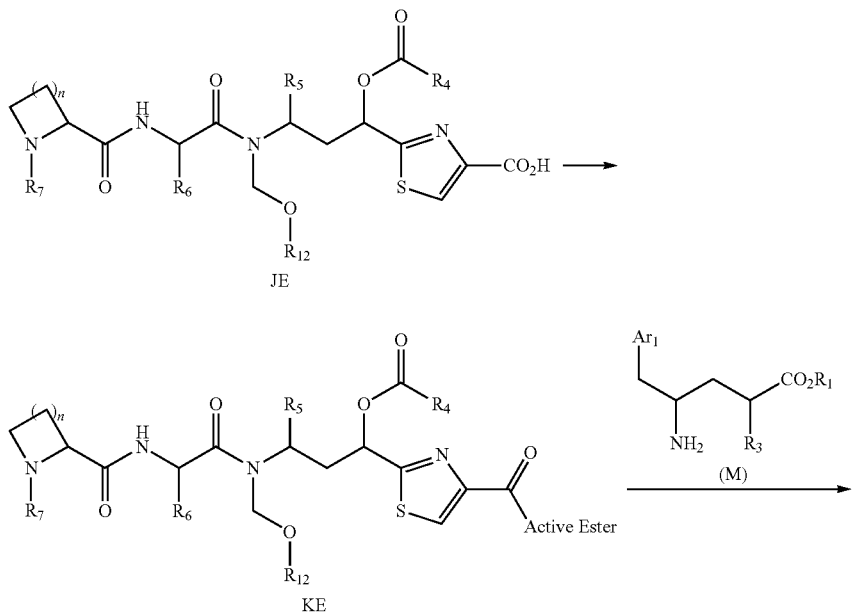

JE

KE (M)

-continued

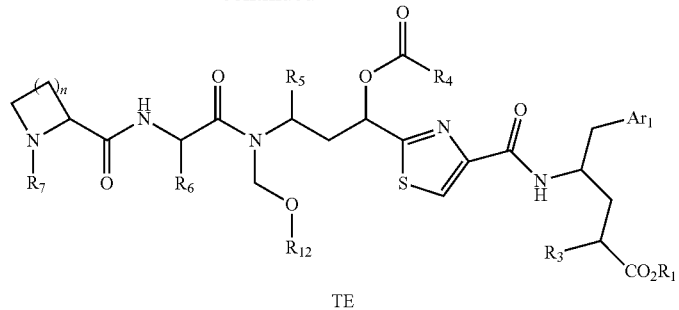

TE

In another embodiment, a process is described for preparing a tubulysin linker derivative of formula (TE-L-X), wherein n, $Ar_1$, $R_1$, $R_3$, $R_4$, $R_5$, $R_6$, $R_7$, and $R_{12}$ are each independently selected from any of the various embodiments described herein;

L is selected from the group consisting of

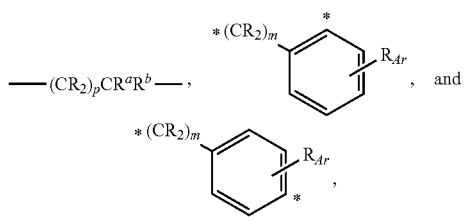

where p is an integer from about 1 to about 3, m is an integer from about 1 to about 4, and * indicates the points of attachment; where $R^a$, $R^b$, and R are each independently selected in each instance from the group consisting of hydrogen and alkyl; or at least two of $R^a$, $R^b$, or R are taken together with the attached carbon atoms to form a carbocyclic ring;

$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof; and X is an activated sulfur that includes a leaving group that allows formation of a bond between the sulfur and a nucleophile.

The process comprises the step of contacting compound T-L-X, with an alcohol, $R_{12}OH$, and a transesterification catalyst, as defined herein.

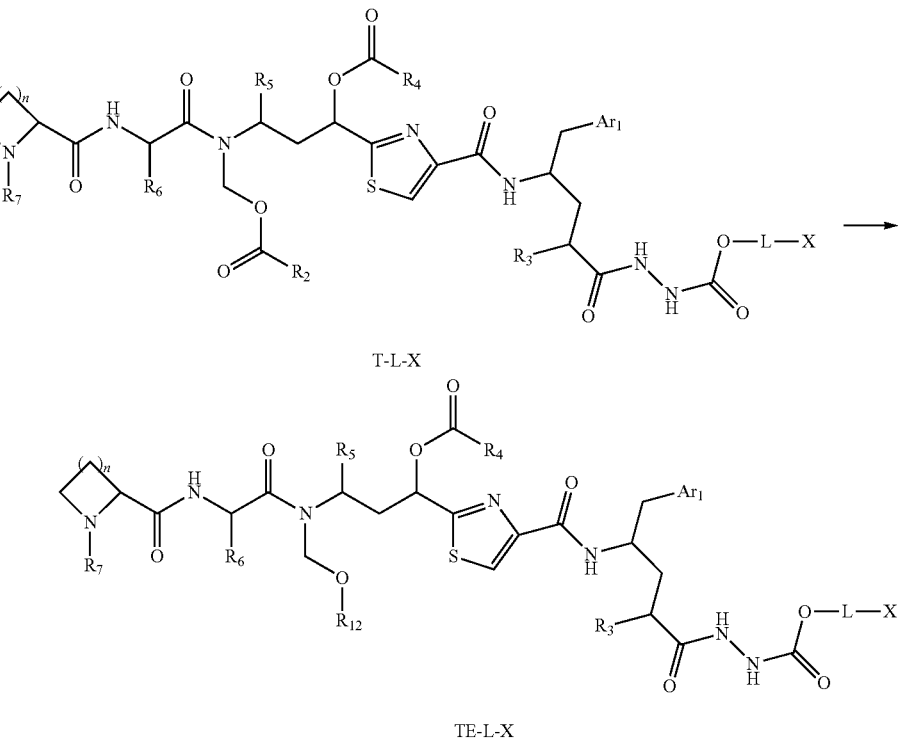

T-L-X

TE-L-X

Compounds of formula T-L-X are prepared according to the processes described in PCT international application serial No. PCT/US2013/034672, the disclosure of which is incorporated herein by reference. In another embodiment, the transesterification catalyst is TFA. In another embodiment, X is SS—$Ar_2$, where $Ar_2$ is optionally substituted aryl or optionally substituted heteroaryl. In another embodiment, $Ar_2$ is selected from optionally substituted pyridin-2-yl, pyridin-2-yl, nitrophenyl, and the like.

In another embodiment, a process is described for preparing a tubulysin linker derivative of formula (TE-L-X), wherein L, X, n, $Ar_1$, $R_1$, $R_2$, $R_3$, $R_4$, $R_5$, $R_6$, $R_7$, and $R_{12}$ are each independently selected from any of the various embodiments described herein. The process comprises the step of forming an active ester intermediate KE, where Y is a leaving group, from a compound of formula JE; and reacting the active ester intermediate KE with a compound of the formula M-L-X to give a compound of the formula TE-L-X.

example, in another illustrative embodiment of any of the processes or process steps described hereinabove or hereinbelow, $Ar_1$ is optionally substituted aryl. In another illustrative embodiment of any of the processes or process steps described hereinabove or hereinbelow, $Ar_1$ is optionally substituted heteroaryl.

It is also to be understood that each of $Ar_1$, $Ar_2$, $R_1$, $R_2$, $R_{12}$, $R_3$, $R_4$, $R_5$, $R_6$, and $R_7$ may include any necessary or desirable conventional protection groups as appropriate for the reaction conditions in the corresponding process step.

DETAILED DESCRIPTION

In another embodiment, a process is described for preparing a compound of formula B, where the process comprises the step of treating a compound of formula A with triethylsilyl chloride and imidazole in an aprotic solvent.

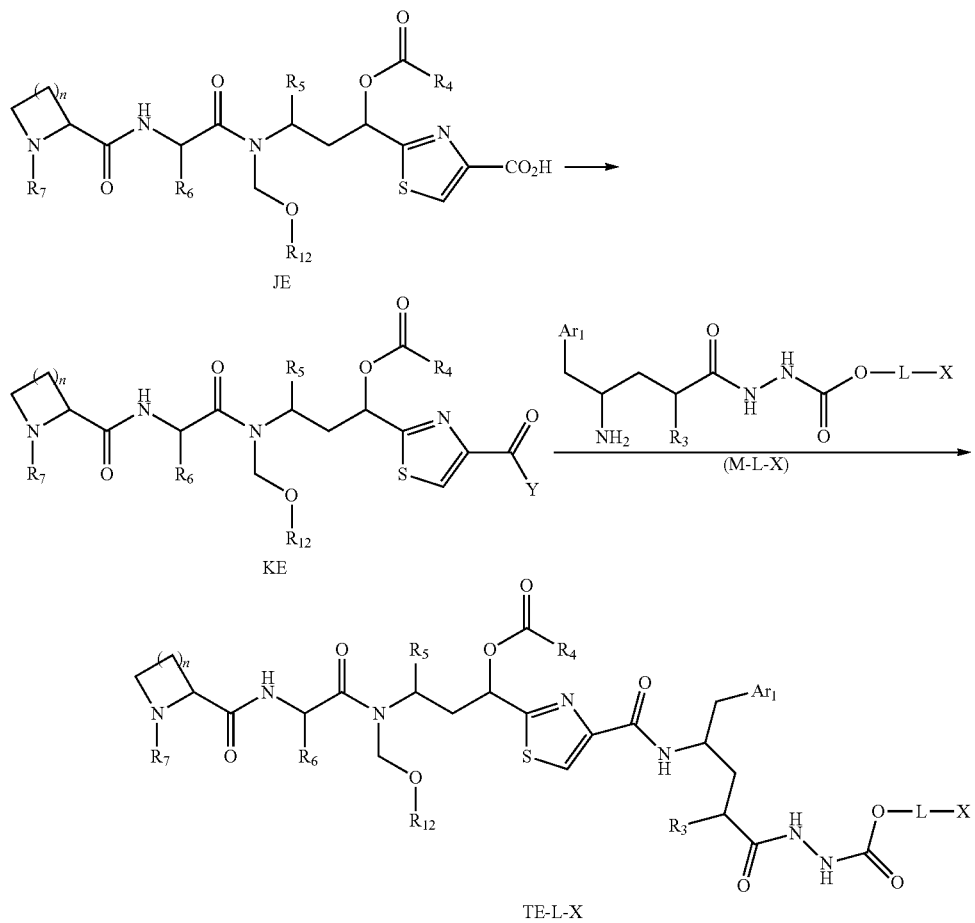

Compounds of formula M-L-X are prepared according to the processes described in PCT international application serial No. PCT/US2013/034672, the disclosure of which is incorporated herein by reference.

It is to be understood that in each process or process step described hereinabove or hereinbelow, each group L, X, n, $Ar_1$, $R_1$, $R_2$, $R_3$, $R_4$, $R_5$, $R_6$, $R_7$, and $R_{12}$ is independently selected in each instance from any of the various embodiments, genera, subgenera, or lists described herein. For

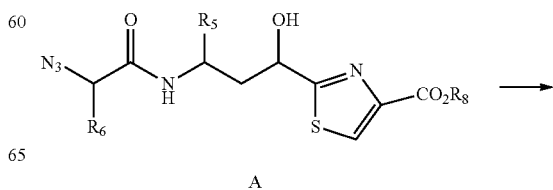

A

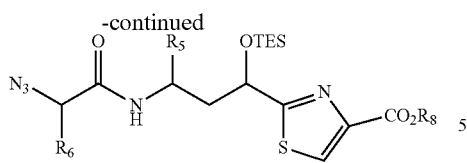

B

In an illustrative example of the processes described herein, a process for preparing the silyl ether 2 in high yield is described wherein compound 1 is treated with 1.05 equivalent of TESCl and 1.1 equivalent of imidazole.

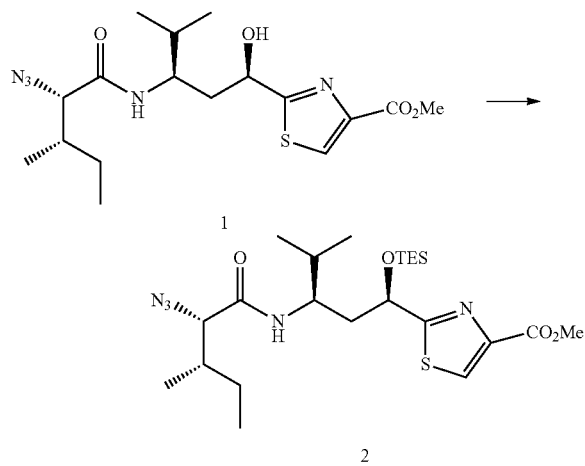

In one alternative of the foregoing example, the compound 2 is not purified by chromatography.

In another embodiment, a process is described for preparing a compound of formula C, where the process comprises the step of treating a compound of formula B with from about 1 equivalent to about 1.5 equivalent of base and from about 1 equivalent to about 1.5 equivalent of a compound of the formula ClCH$_2$OC(O)R$_2$ in an aprotic solvent at a temperature from about −78° C. to about 0° C.

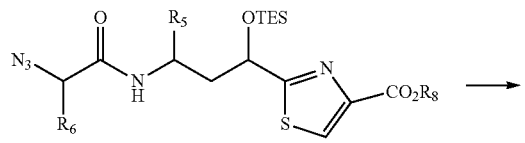

B

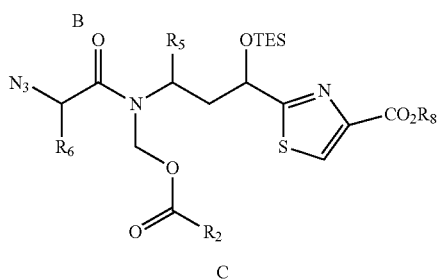

C

In another embodiment, the process of the preceding embodiment is described wherein the compounds of formulae B and C have the stereochemistry shown in the following scheme for B1 and C1.

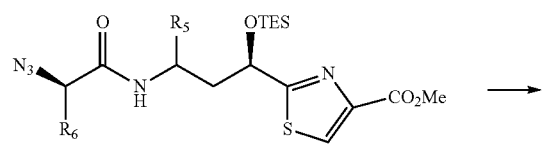

B1

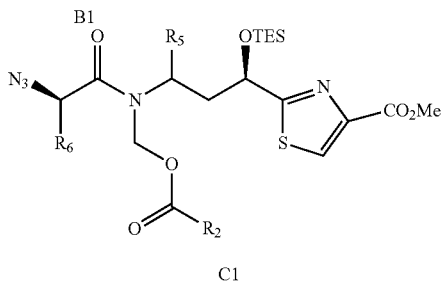

C1

In another illustrative embodiment, the process of any one of the preceding embodiments is described wherein about 1 equivalent to about 1.3 equivalent of a compound of the formula YCH$_2$OC(O)R$_2$ is used, where Y is a leaving group, such as halo selected from chloro, bromo, and iodo. In another illustrative example, the process of any one of the preceding embodiments is described, wherein about 1.2 equivalent of a compound of the formula ClCH$_2$OC(O)R$_2$ is used. In another illustrative example, the process of any one of the preceding embodiments is described wherein R$_2$ is n-propyl. In another alternative of the foregoing embodiments, and each additional embodiment described herein, R$_2$ is CH$_2$CH(CH$_3$)$_2$, CH$_2$CH$_2$CH$_3$, CH$_2$CH$_3$, CH=C(CH$_3$)$_2$, or CH$_3$.

In an illustrative example of the processes described herein, a process for preparing the N,O-acetal 3 is described. In another illustrative example, compound 2 is treated with 1.1 equivalent of potassium hexamethyldisilazane (KHMDS) and 1.2 equivalent of chloromethyl butanoate in a nonprotic solvent at about −45° C. In another illustrative example, the product formed by any of the preceding examples may be used without chromatographic purification.

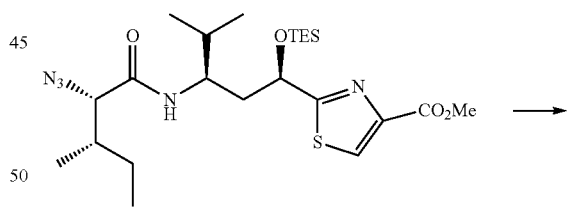

2

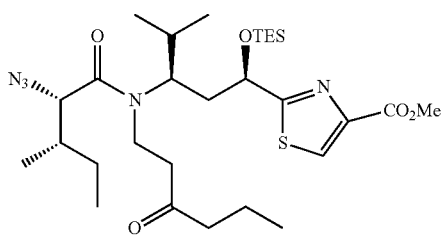

3

In another embodiment, a process is described for preparing a compound of formula D, where the process comprises the steps of a) preparing a compound of formula (E1) where $X_1$ is a leaving group or acyl activating group from a compound of formula E; and b) treating a compound of formula C under reducing conditions with the compound of formula E1.

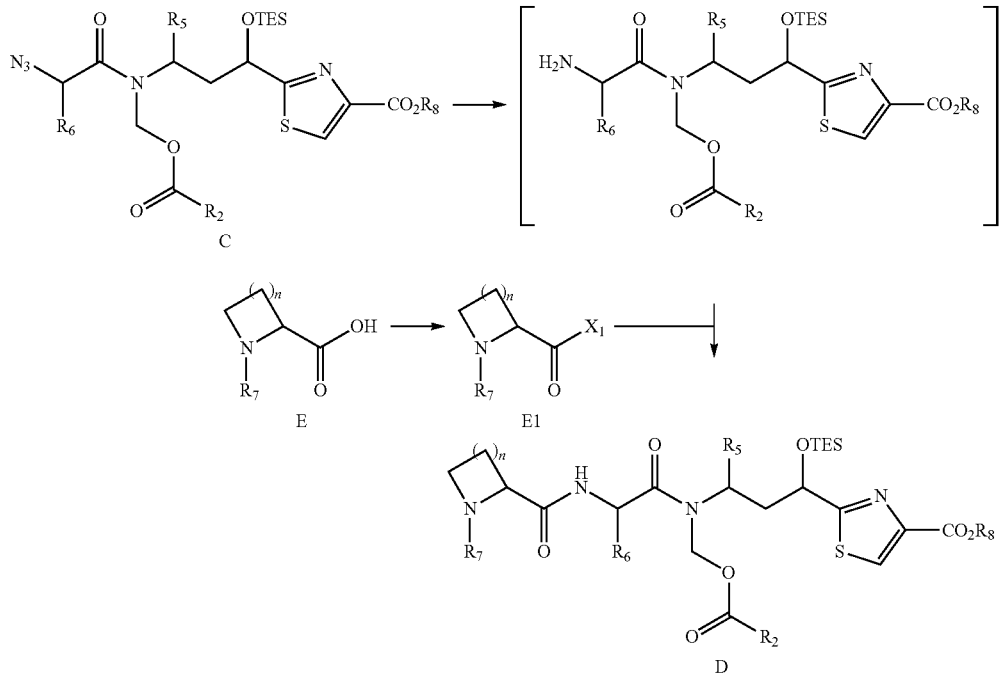

In another alternative of the foregoing embodiments, and each additional embodiment described herein, n is 3. In another alternative of the foregoing embodiments, and each additional embodiment described herein, $R_7$ is methyl. In one illustrative example, a mixture of compound 3 and the pentafluorophenyl ester of D-N-methyl-pipecolic acid is reduced using $H_2$ and a palladium-on-charcoal catalyst (Pd/C) to yield compound 4.

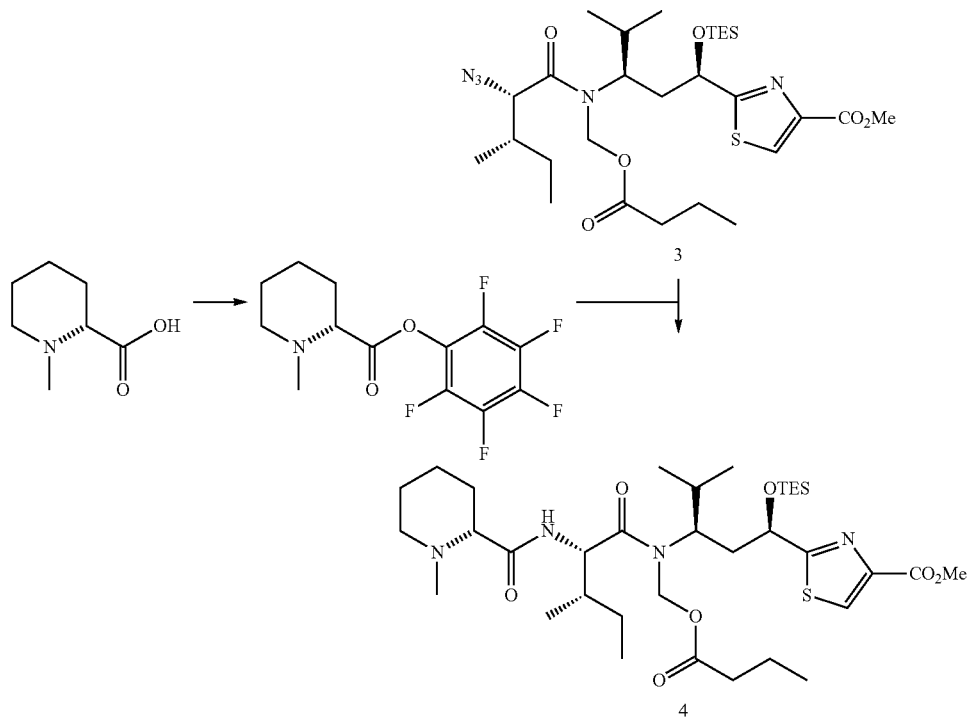

In another embodiment, a process is described for preparing a compound of formula FE, wherein $R_5$ and $R_6$ are as described in the various embodiments herein, such as being selected from optionally substituted alkyl or optionally substituted cycloalkyl; $R_2$ is as described in the various embodiments herein, such as being selected from optionally substituted alkyl or optionally substituted cycloalkyl; and $R_7$ is optionally substituted alkyl; wherein the process comprises the step of contacting compound D with an alcohol, $R_{12}OH$, where $R_{12}$ is alkyl, alkenyl, alkynyl, heteroalkyl, cycloalkyl, heterocycloalkyl, aryl, arylalkyl or heteroarylalkyl, each of which is optionally substituted; and a transesterification catalyst. In another embodiment the transesterification catalyst is trifluoroacetic acid (TFA). In another embodiment, the transesterification catalyst is selected from the group consisting of $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where $R_{13}$ is independently selected from alkyl, arylalkyl, aryl, or cycloalkyl, each of which is optionally substituted. In another embodiment, the transesterification catalyst is $(R_{13})_2SnO$. Illustrative examples of $R_{13}$ are methyl, n-butyl, n-octyl, phenyl, o-MeO-phenyl, p-MeO phenyl, phenethyl, benzyl, and the like.

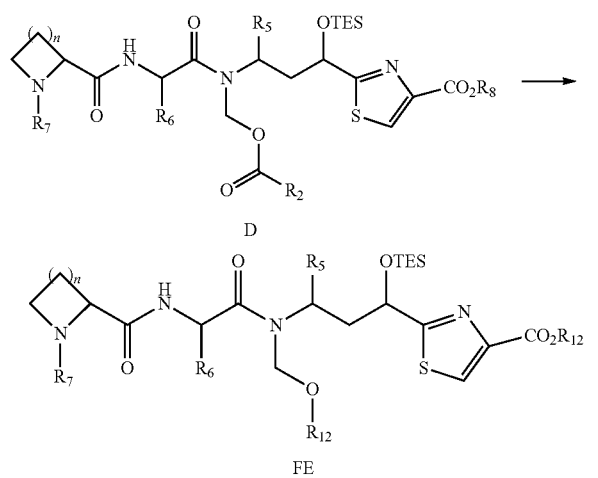

D

FE

In an illustrative example, compound 4 is heated with an alcohol and di-n-butyltin oxide at about 100° C. to yield ether FE1 (10), where R is as defined in the various embodiments herein. It is appreciated that a co-solvent may be present. In one embodiment, the molar ratio (tin oxide)/(compound 4) is about 0.01 to about 0.30, or about 0.02 to about 0.20, or about 0.05 to about 0.15, or about 0.05 to about 0.10

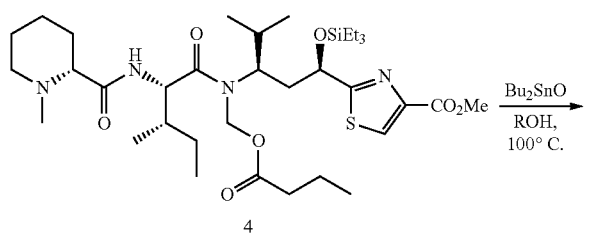

4

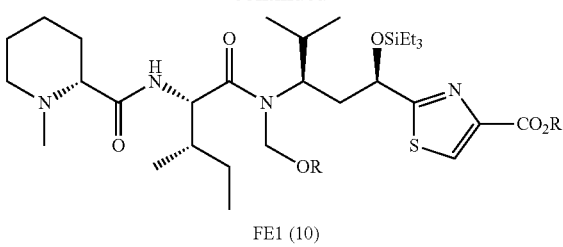

FE1 (10)

In another embodiment, a process is described for preparing a transesterification product of each of the compounds of formula A and/or B, wherein $R_5$, $R_6$, and $R_8$ are as described in the various embodiments herein, and where $R_{12}$ is different from $R_8$; wherein the process comprises the step of contacting compound A or B with an alcohol, $R_{12}OH$, and a transesterification catalyst, as described herein.

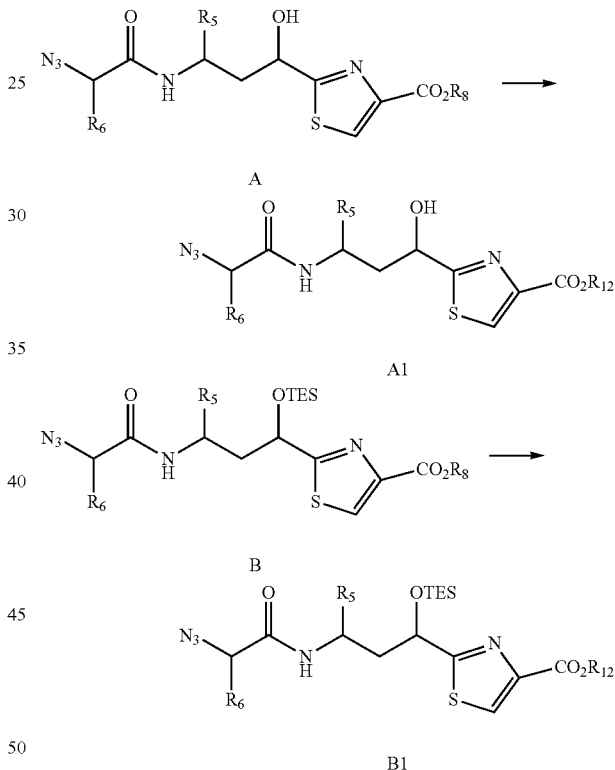

In another embodiment, a process is described for preparing a compound of formula IE, wherein $R_5$ and $R_6$ are as described in the various embodiments herein, such as being selected from optionally substituted alkyl or optionally substituted cycloalkyl; $R_{12}$ is as described in the various embodiments herein, such as being selected from alkyl, alkenyl, alkynyl, heteroalkyl, cycloalkyl, heterocycloalkyl, aryl, arylalkyl or heteroarylalkyl, each of which is optionally substituted; and $R_7$ is optionally substituted alkyl; wherein the process comprises the step of contacting compound FE with a metal hydroxide or carbonate. Illustrative examples of a metal hydroxide or carbonate include LiOH, $Li_2CO_3$, NaOH, $Na_2CO_3$, KOH, $K_2CO_3$, $Ca(OH)_2$, $CaCO_3$, $Mg(OH)_2$, $MgCO_3$, and the like.

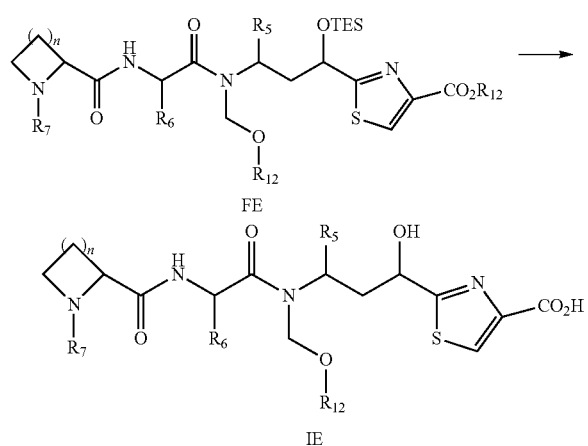

FE

IE

It is to be understood that $R_5$, $R_6$, $R_7$, and $R_{12}$ may each include conventional protection groups on the optional substituents.

In an illustrative example, compound FE1 (10) is treated with LiOH·H$_2$O in a mixture of THF and water at about room temperature to yield compound IE1 (11). It is appreciated that the THF may be replaced with other solvents.

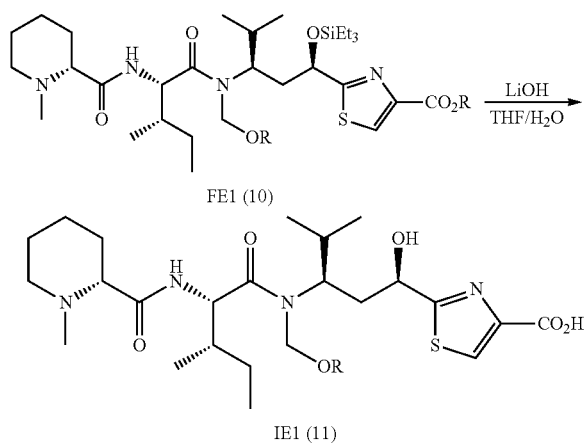

FE1 (10)

IE1 (11)

In another embodiment, a process is described for preparing a compound of formula JE, wherein $R_5$, $R_6$, $R_{12}$, $R_4$, and $R_7$ are each independently selected from any of the various embodiments described herein; wherein the process comprises the step of treating a compound of formula IE with an acylating agent of formula $R_4C(O)X_2$, where $X_2$ is a leaving group. It is appreciated that the resulting product may contain varying amounts of the mixed anhydride of compound JE and $R_4CO_2H$. In another embodiment, the process described in the preceding embodiment further comprises the step of treating the reaction product with water to prepare JE, free of or substantially free of anhydride. In another embodiment, the process of the preceding embodiments wherein $X_2$ is $R_4CO_2$, is described. In another embodiment, the process of any one of the preceding embodiments wherein $R_4$ is C1-C4 alkyl is described. In another alternative of the foregoing embodiments, and each additional embodiment described herein, $R_4$ is methyl. In another embodiment, the process of any one of the preceding embodiments wherein $R_6$ is sec-butyl is described. In another embodiment, the process of any one of the preceding embodiments wherein $R_7$ is methyl is described.

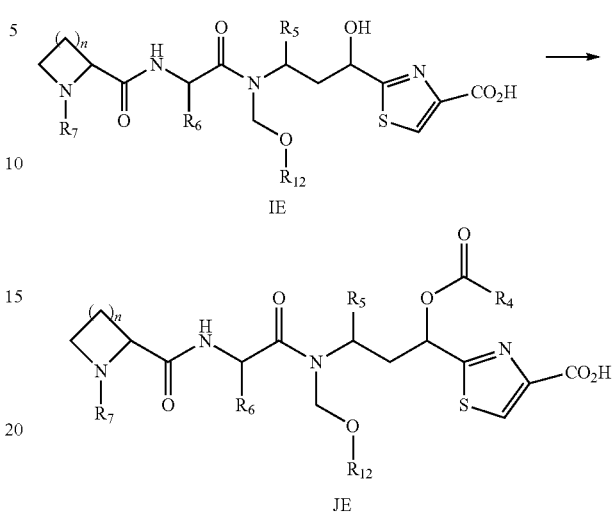

IE

JE

In an illustrative example, compound IE1 (11) is treated with acetic anhydride in pyridine. It is appreciated that the resulting product JE1 (12) may contain varying amounts of the corresponding mixed anhydride of the terminal carboxylic acid of JE1 (12) and acetic acid. In another embodiment, treatment of the reaction product resulting from the preceding step with water in dioxane yields compound JE1 (12), free of or substantially free of the corresponding anhydride. It is to be understood that other solvents can be substituted for dioxane in the hydrolysis of the intermediate mixed anhydride. Alternatively, the step may be performed without solvent.

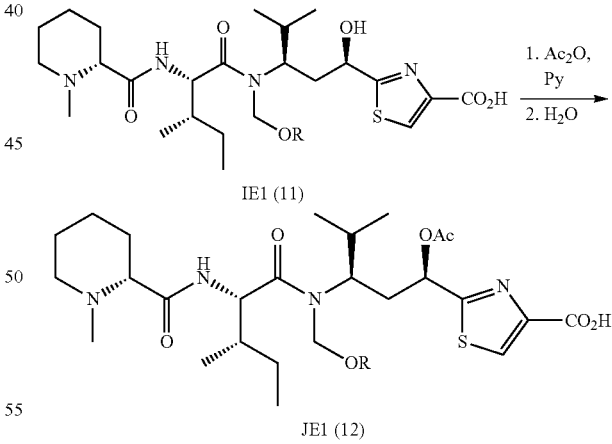

IE1 (11)

JE1 (12)

In another embodiment, a process is described for preparing a tubulysin of formula (TE), wherein Ar$_1$ is optionally substituted aryl; $R_1$ is hydrogen, optionally substituted alkyl, optionally substituted arylalkyl or a pro-drug forming group; $R_5$ and $R_6$ are as described in the various embodiments herein, such as being selected from optionally substituted alkyl or optionally substituted cycloalkyl; $R_3$ is optionally substituted alkyl; $R_4$ is as described in the various embodiments herein, such as being selected from optionally substituted alkyl or optionally substituted cycloalkyl; $R_{12}$ is as described in the various embodiments herein, such as being selected from alkyl, alkenyl, alkynyl, heteroalkyl, cycloalkyl, heterocycloalkyl, aryl, arylalkyl or heteroarylalkyl, each of which is optionally substituted; and $R_7$ is optionally substituted alkyl; wherein the process comprises the step of forming an active ester intermediate from a compound of formula JE; and reacting the active ester intermediate with a compound of the formula M to give a compound of the formula TE.

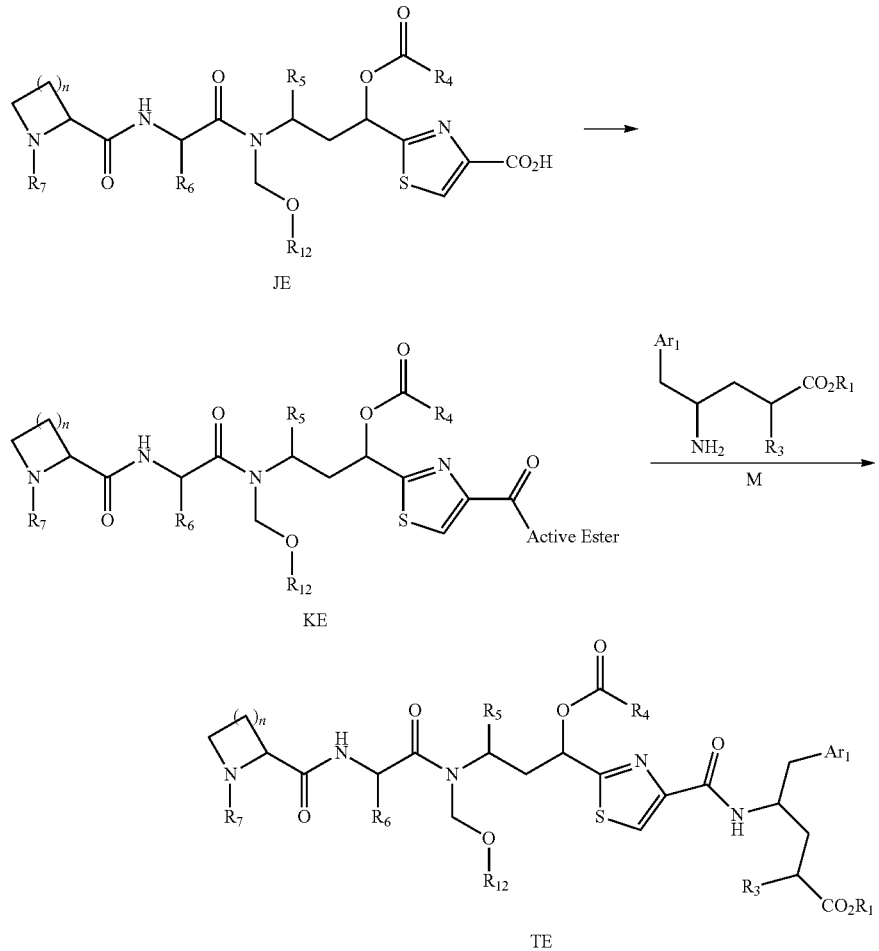

In another embodiment, a process is described for preparing a tubulysin linker derivative of formula (TE-L-X), wherein L, X, n, $Ar_1$, $R_1$, $R_3$, $R_4$, $R_5$, $R_6$, $R_7$, and $R_{12}$ are each independently selected from any of the various embodiments described herein. The process comprises the step of forming an active ester intermediate KE, where Y is a leaving group, from a compound of formula JE; and reacting the active ester intermediate KE with a compound of the formula M-L-X to give a compound of the formula TE-L-X.

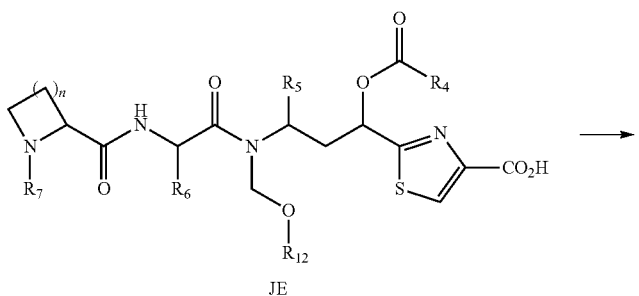

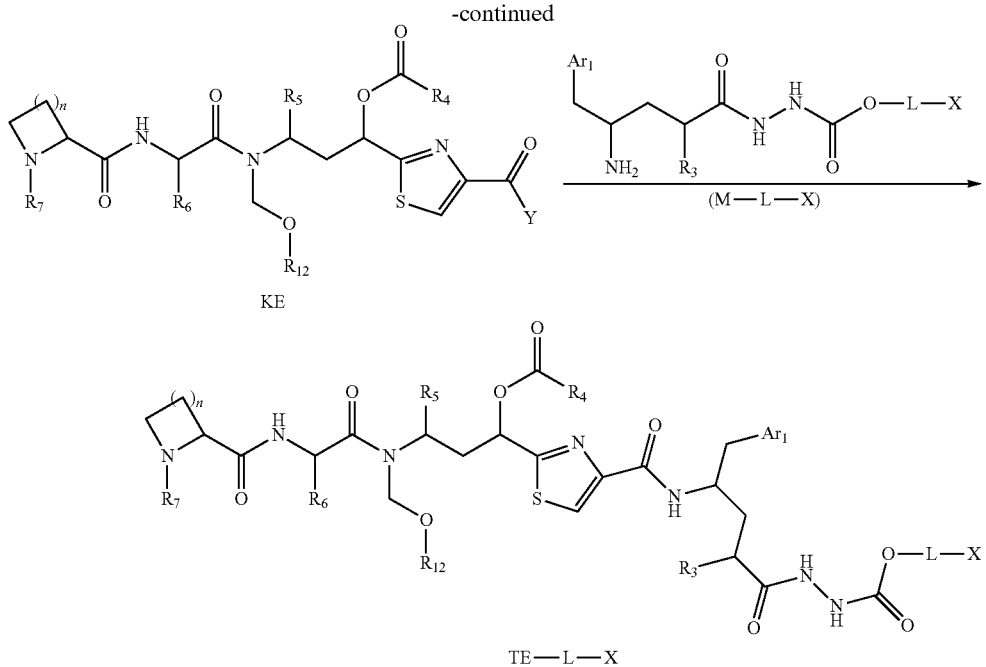

KE

TE—L—X

Compounds of formula M-L-X are prepared according to the processes described in PCT international application serial No. PCT/US2013/034672, the disclosure of which is incorporated herein by reference.

In one embodiment, compound JE is treated with an excess amount of active ester forming agent and pentafluorophenol to form the pentafluorophenol ester of compound JE, followed by removal of the excess active ester forming agent prior to the addition of compound I. In another alternative of the foregoing embodiments, and each additional embodiment described herein, $Ar_1$ is phenyl. In another alternative of the foregoing embodiments, and each additional embodiment described herein, $Ar_1$ is substituted phenyl. In another alternative of the foregoing embodiments, and each additional embodiment described herein, $Ar_1$ is 4-substituted phenyl. In another alternative of the foregoing embodiments, and each additional embodiment described herein, $Ar_1$ is $R_A$-substituted phenyl. In another alternative of the foregoing embodiments, and each additional embodiment described herein, $Ar_1$ is 4-hydroxyphenyl, or a hydroxyl protected form thereof. In another alternative of the foregoing embodiments, and each additional embodiment described herein, $R_3$ is methyl. In another alternative of the foregoing embodiments, and each additional embodiment described herein, $R_1$ is hydrogen.

In an illustrative example, compound JE1 (12) is treated with an excess amount of a polymeric version of a carbodiimide and pentafluorophenol to form the pentafluorophenyl ester of JE1 (12), the polymeric carbodiimide is removed by filtration; and amino acid (S)-tubutyrosine is added to the solution to yield the tubulysin, compound TE1 (13). In another embodiment, the process of any one of the preceding embodiments wherein the polymeric carbodiimide is polystyrene-$CH_2$—N=C=N-cyclohexane (PS-DCC) is described.

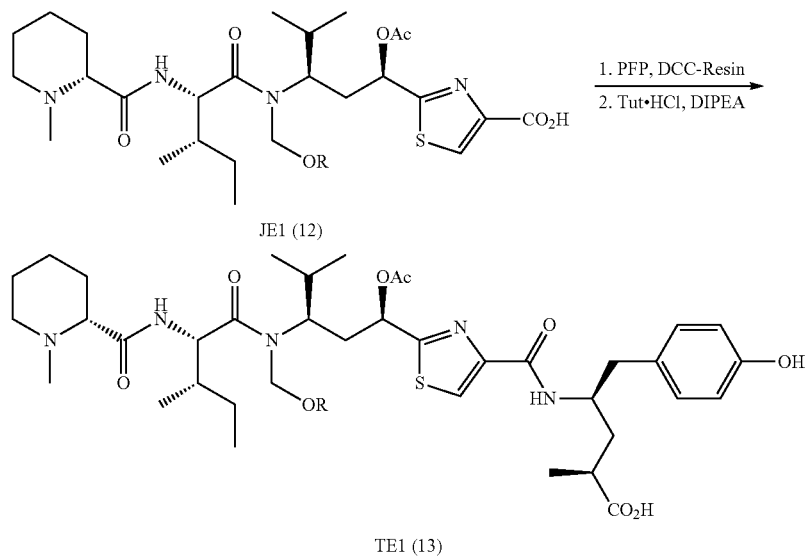

JE1 (12)

TE1 (13)

In another embodiment, the ether analog 8-e can be converted to the ether analog 2-e, via the ether analog 15-e, where R is allyl, or $CH_2(CH_2)_nCH_3$, and n is 1, 2, 3, 4, 5, or 6.

In another embodiment, the following compound is described wherein $R_{12}$, $R_5$, $R_6$, $R_7$ and $R_8$ are as described in the any of the embodiments described herein.

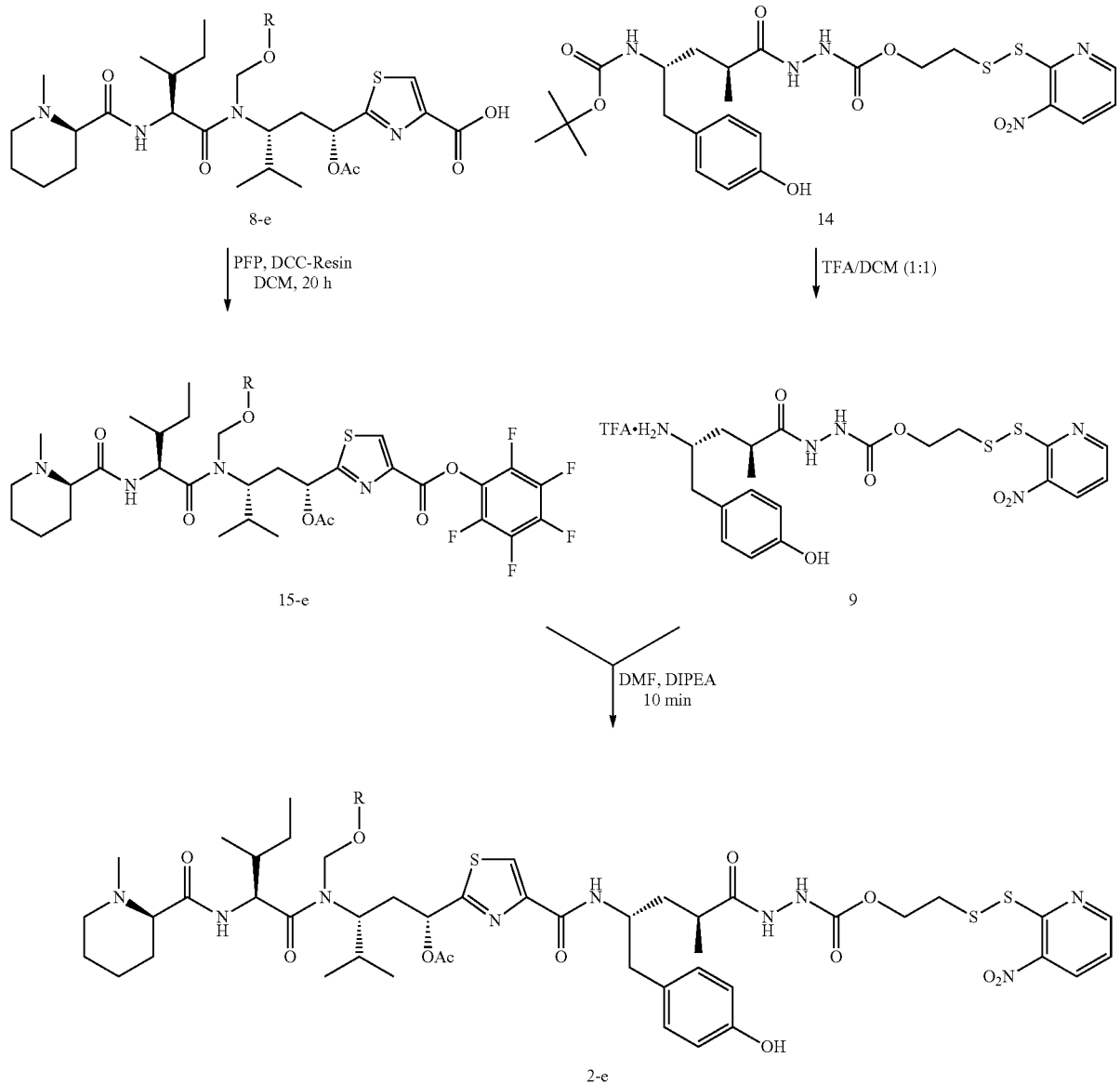

In another embodiment, a compound FE is described wherein $R_{12}$, $R_5$, $R_6$, and $R_7$ are as described in the any of the embodiments described herein.

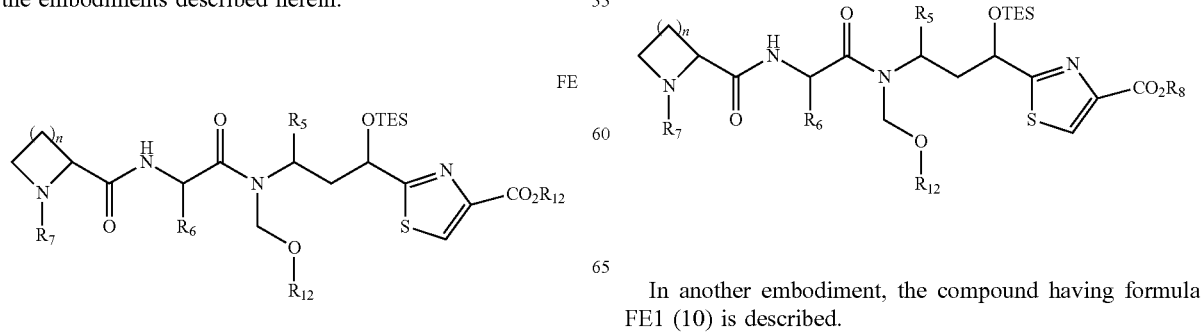

In another embodiment, the compound having formula FE1 (10) is described.

FE1 (10)

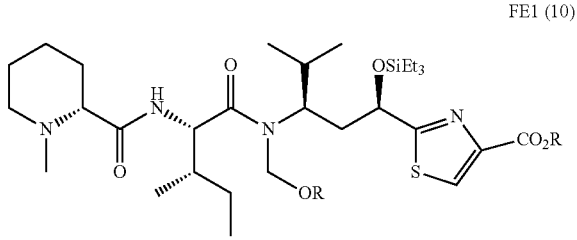

where R is selected from any of the various embodiments described herein.

In another embodiment a compound IE, is described, wherein $R_{12}$, $R_5$, $R_6$, and $R_7$ are as described in any of the embodiments described herein.

IE

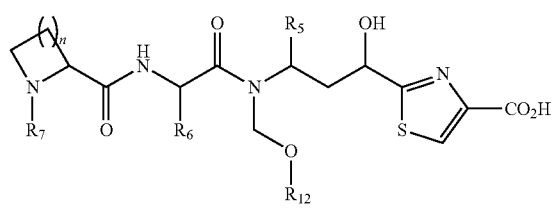

In another embodiment, compound IE 1(11) is described.

IE 1(11)

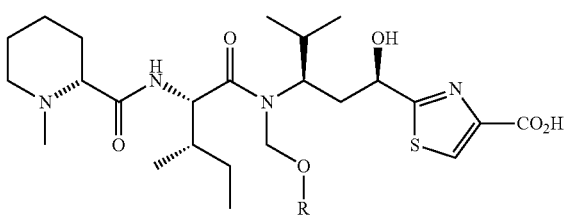

In another embodiment, compound JE1 (12) is described.

JE1 (12)

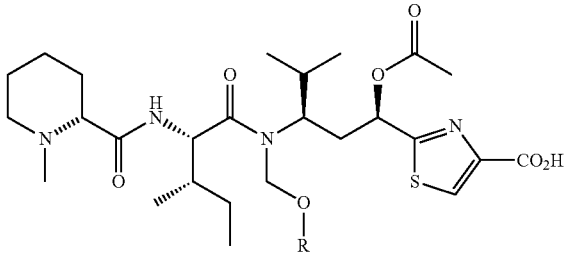

In another embodiment, a compound JE is described wherein $R_4$ is Me and $R_{12}$, $R_5$, $R_6$, and $R_7$ are as described in any of the embodiments described herein.

JE

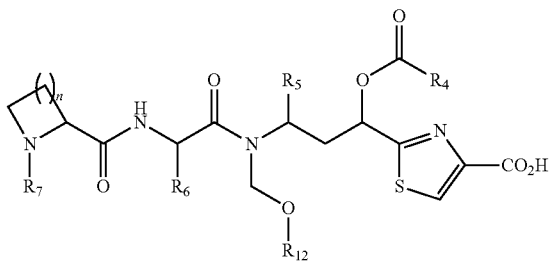

In another alternative of the foregoing embodiments, and each additional embodiment described herein, $R_5$ is isopropyl. In another alternative of the foregoing embodiments, and each additional embodiment described herein, $R_3$ is methyl. In another alternative of the foregoing embodiments, and each additional embodiment described herein, $R_1$ is hydrogen.

It is to be understood that the acyloxymethyl group ($R_2$—C(O)—O—CH$_2$) present on any of compounds C, D, F, G, H, and T may be converted into the corresponding ether group ($R_{12}$—O—CH$_2$), or other group using the process of contacting the compound with trifluoroacetic acid (TFA), as described herein, and also as described in WO 2009/055562, the disclosure of which is incorporated herein by reference.

Illustrative embodiments of the invention are further described by the following delineated clauses:

A process for preparing a compound of the formula (TE)

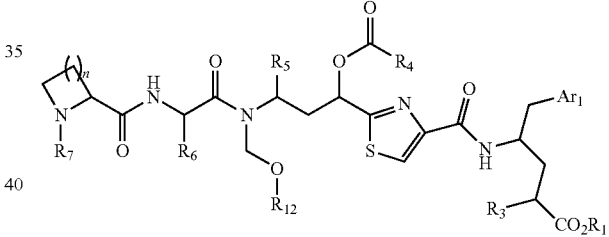

or a pharmaceutically acceptable salt thereof; wherein $Ar_1$ is optionally substituted aryl or optionally substituted heteroaryl;

$R_1$ is hydrogen, optionally substituted alkyl, optionally substituted arylalkyl or a pro-drug forming group;

$R_2$ is selected from the group consisting of optionally substituted alkyl, optionally substituted cycloalkyl, optionally substituted arylalkyl, and optionally substituted heteroarylalkyl;

$R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted;

$R_3$ is optionally substituted alkyl;

$R_4$ is optionally substituted alkyl or optionally substituted cycloalkyl;

$R_5$ and $R_6$ are each independently selected from the group consisting of optionally substituted alkyl and optionally substituted cycloalkyl;

$R_7$ is hydrogen or optionally substituted alkyl; and n is 1, 2, 3, or 4;

the process comprising the step of (a) treating a compound of formula A with triethylsilyl chloride and imidazole in an aprotic solvent, where $R_8$ is $C_1$-$C_6$ unbranched alkyl, such as methyl, or arylalkyl, such as benzyl;

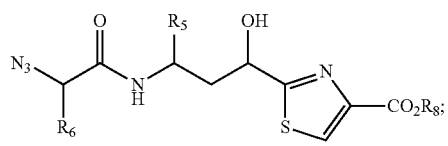

A or (b) treating a compound of formula B with a base and a compound of the formula $YCH_2OC(O)R_2$, where Y is a leaving group, such as chloro, bromo, or iodo, and where $R_8$ is $C_1$-$C_6$ unbranched alkyl, such as methyl, or arylalkyl, such as benzyl

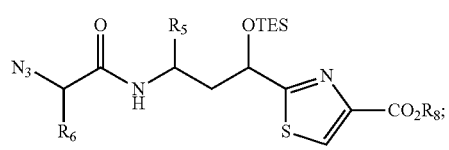

B or the steps of (c1) preparing a compound of formula (E1), where $X_1$ is a leaving group, from a compound of formula E

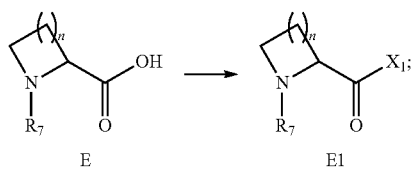

and (c2) mixing a compound of formula C under reducing conditions with the compound of formula E1

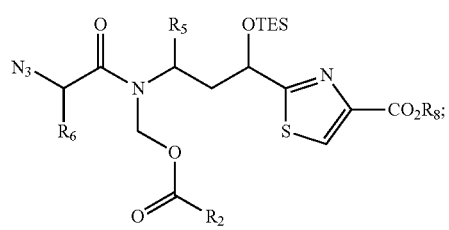

C or the step of (d) contacting compound D with an alcohol, $R_{12}OH$; and a transesterification catalyst selected from the group consisting of trifluoroacetic acid, $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where $R_{13}$ is independently selected from alkyl, arylalkyl, aryl, or cycloalkyl, each of which is optionally substituted;

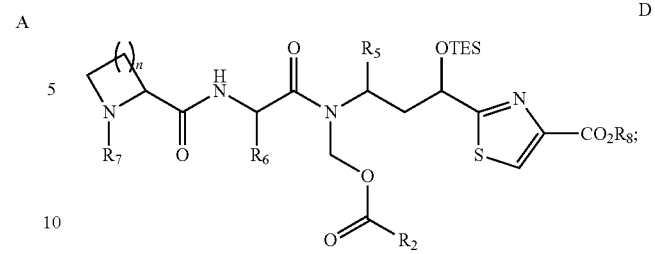

D or the step of (e) treating a compound of the formula FE with a metal hydroxide or a metal carbonate;

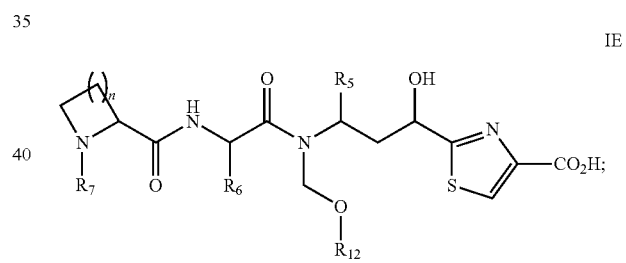

FE or the step of (f) treating a compound of the formula IE with an acylating agent of the formula $R_4C(O)X_2$, where $X_2$ is a leaving group

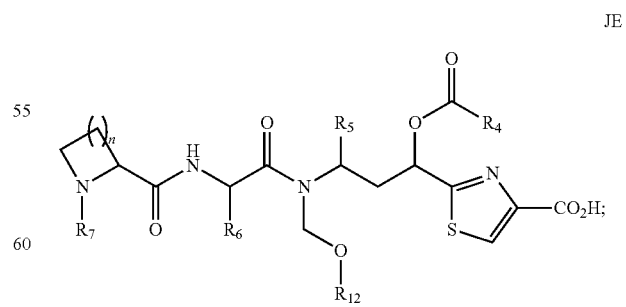

IE or the steps of (g1) forming an active ester intermediate from a compound of formula JE

JE and (g2) reacting the active ester intermediate with a compound of the formula M

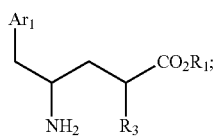

or one or more combinations of any of the foregoing steps.

A process for preparing a compound of the formula (TE-L-X)

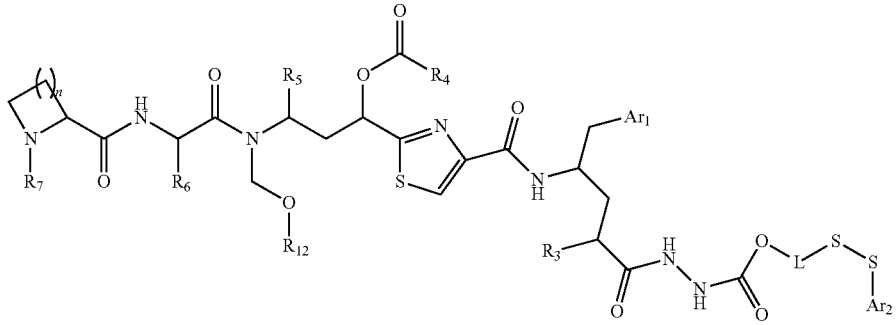

(TE-L-X)

wherein n, $Ar_1$, $Ar_2$, $R_2$, $R_3$, $R_4$, $R_5$, $R_6$, $R_7$, and $R_{12}$ are each independently selected from any of the embodiments described herein;

L is selected from the group consisting of

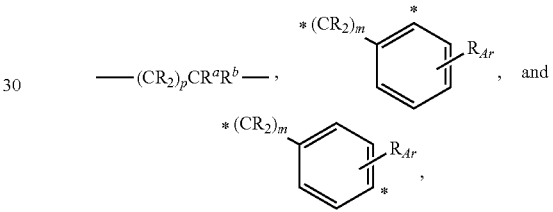

where p is an integer from about 1 to about 3, m is an integer from about 1 to about 4, and * indicates the points of attachment;

$R^a$, $R^b$, and R are each independently selected in each instance from the group consisting of hydrogen and alkyl; or at least two of $R^a$, $R^b$, or R are taken together with the attached carbon atoms to form a carbocyclic ring;

$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof; and $Ar_2$ taken together with the attached sulfur forms a leaving group;

the process comprising the step of contacting a compound of the formula (T-L-X)

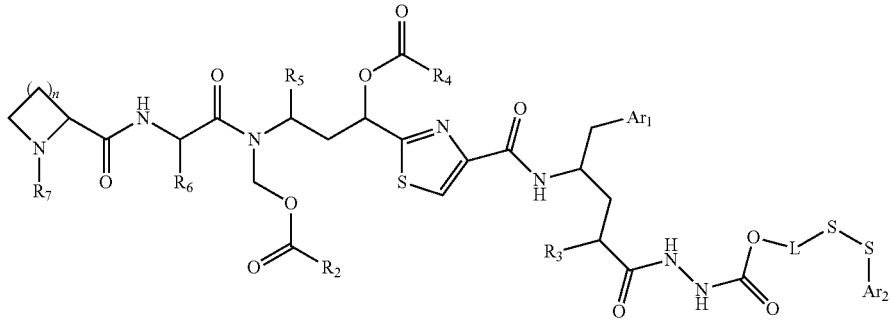

(T-L-X)

with $R_{12}OH$; and a transesterification catalyst, where the transesterification catalyst is independently selected from any of the embodiments described herein.

A process for preparing a compound of the formula (TE-L-X)

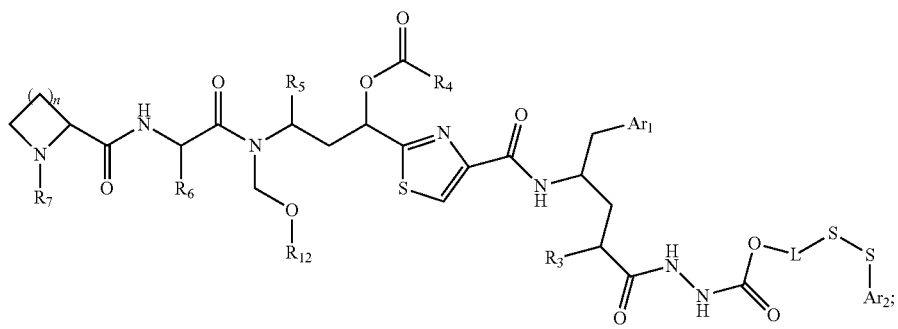

(TE-L-X)

wherein n, L, $Ar_1$, $Ar_2$, $R_3$, $R_4$, $R_5$, $R_6$, $R_7$, and $R_{12}$ are each independently selected from any of the embodiments described herein the process comprising the step of mixing a compound of the formula KE, where Y is a leaving group

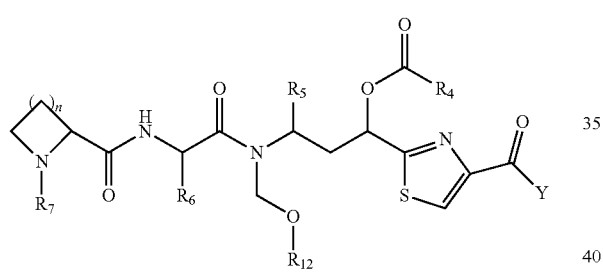

KE with a compound of the formula
M-L-X, where X is the radical SS—$Ar_2$ (M-L-X)

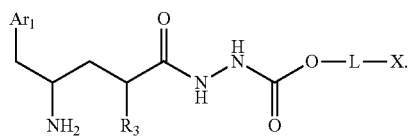

The process of any one of the preceding clauses comprising step (a).

The process of any one of the preceding clauses comprising step (b).

The process of the previous clause wherein step (b) is performed in an aprotic solvent; and/or step (b) is performed at a temperature from about −78° C. to about 0° C.; and/or step (b) is performed where the molar ratio of the compound of the formula $YCH_2OC(O)R_2$ to the compound of formula B is from about 1 to about 1.5.

The process of any one of the preceding clauses comprising steps (c1) and (c2).

The process of any one of the preceding clauses comprising step (d).

The process of the previous clause wherein the transesterification catalyst is selected from the group consisting of $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where $R_{13}$ is independently selected from any of the embodiments described herein.

The process of any one of the preceding clauses comprising step (e).

The process of any one of the preceding clauses comprising step (f).

The process of any one of the preceding clauses comprising steps (g1) and (g2).

A process for preparing a compound of the formula

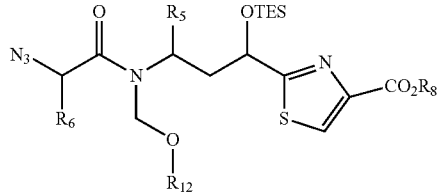

the process comprising the step of contacting a compound of the formula

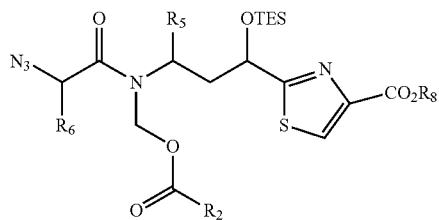

with an acid and $R_{12}OH$; where $R_2$, $R_5$, $R_6$, $R_8$, and $R_{12}$ are each independently selected from any of the embodiments described herein.

A process for preparing a compound of the formula

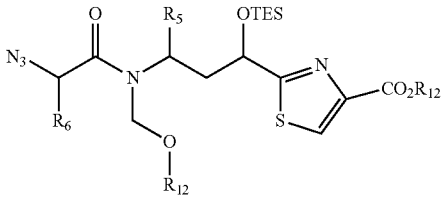

the process comprising the step of contacting a compound of the formula

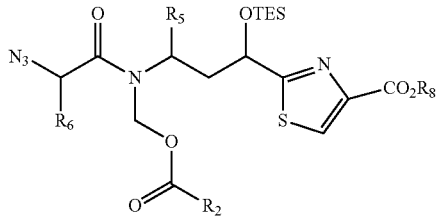

with a transesterification catalyst selected from the group consisting of $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where $R_{13}$ and $R_{12}OH$; where $R_2$, $R_5$, $R_6$, $R_8$, $R_{12}$, and $R_{13}$ are each independently selected from any of the embodiments described herein.

A process for preparing a compound of the formula

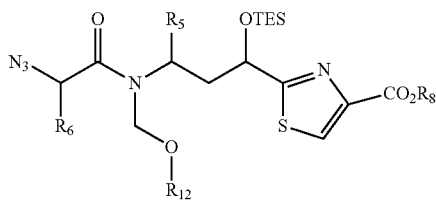

the process comprising the step of contacting a compound of the formula

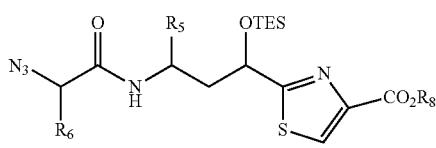

with a base and $R_{12}OCH_2X$, where X is Cl or Br; and $R_5$, $R_6$, $R_8$, and $R_{12}$ are each independently selected from any of the embodiments described herein; or $R_{12}OCH_2X$ is n-$O_5H_{11}OCH_2Br$.

A process for preparing a compound of the formula

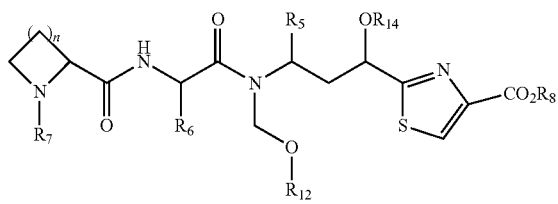

the process comprising the step of contacting a compound of the formula

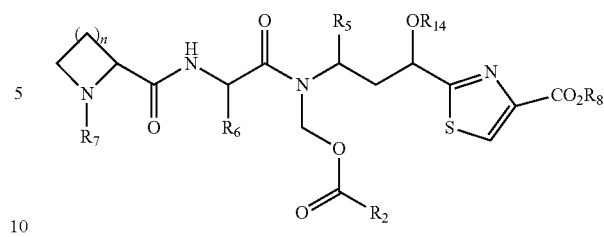

with an acid and $R_{12}OH$, wherein $R_{14}$ is $Et_3Si$ or $R_4C(O)$, and n, $R_2$, $R_4$, $R_5$, $R_6$, $R_7$, $R_8$, and $R_{12}$ are each independently selected from any of the embodiments described herein.

A process for preparing a compound of the formula

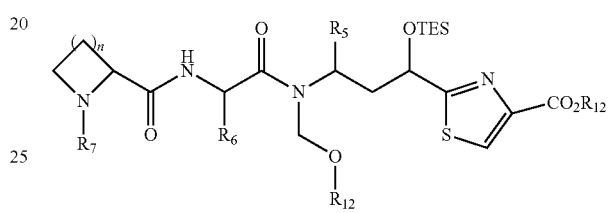

the process comprising the step of contacting a compound of the formula

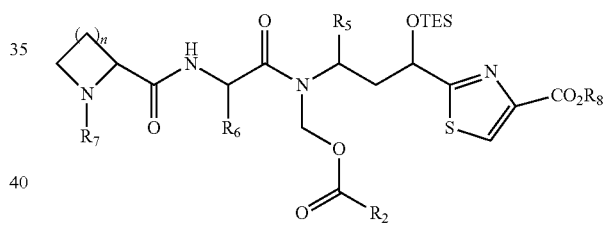

with a transesterification catalyst selected from the group consisting of $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where wherein n, $R_2$, $R_5$, $R_6$, $R_7$, $R_8$, $R_{12}$, and $R_{13}$ are each independently selected from any of the embodiments described herein.

The process of any one of the previous clauses comprising the step of treating a compound of formula A with triethylsilyl chloride and imidazole in an aprotic solvent, where $R_8$ is $C_1$-$C_6$ unbranched alkyl, such as methyl, or arylalkyl, such as benzyl

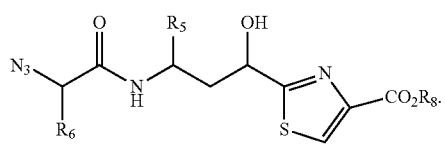

A

A process for preparing a compound of the formula

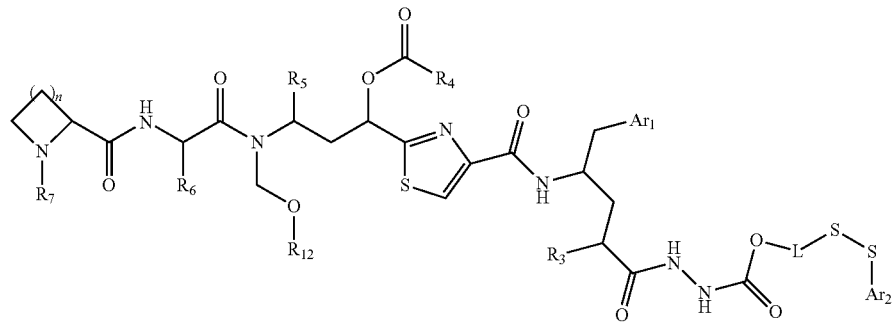

the process comprising the step of contacting a compound of the formula

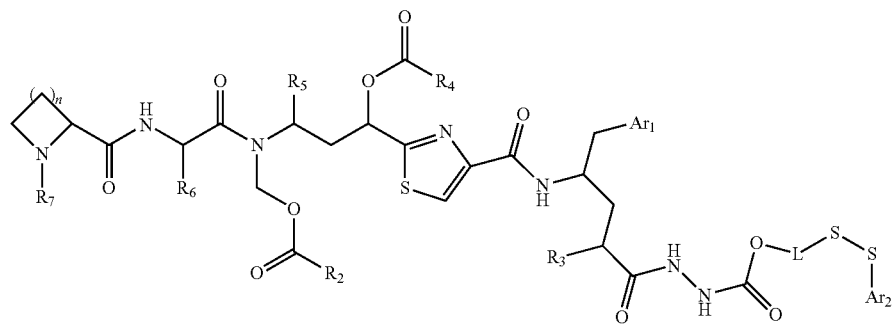

with an acid and $R_{12}OH$, wherein n, $R_2$, $R_3$, $R_4$, $R_5$, $R_6$, $R_7$, $Ar_1$, $Ar_2$, L and $R_{12}$ are each independently selected from any of the embodiments described herein.

The process of any one of the preceding clauses wherein the metal carbonate is selected from $Li_2CO_3$, $Na_2CO_3$, $K_2CO_3$, $CaCO_3$, or $MgCO_3$.

The process of any one of the preceding clauses wherein the metal hydroxide is selected from LiOH, NaOH, KOH, $Ca(OH)_2$, or $Mg(OH)_2$ The process of any one of the preceding clauses wherein the metal hydroxide is LiOH.

The process of any one of the preceding clauses wherein the acid selected for the conversion of the $NCH_2OC(O)R_2$ moiety to the $NCH_2OR_{12}$ moiety is TFA.

The process of any one of the preceding clauses wherein the catalyst selected for the conversion of the $NCH_2OC(O)R_2$ moiety to the $NCH_2OR_{12}$ moiety is $(R_{13})_2SnO$.

The process of any one of the preceding clauses wherein the catalyst selected for the conversion of the $NCH_2OC(O)R_2$ moiety to the $NCH_2OR_{12}$ moiety is $(n-Bu)_2SnO$.

A compound of the formula

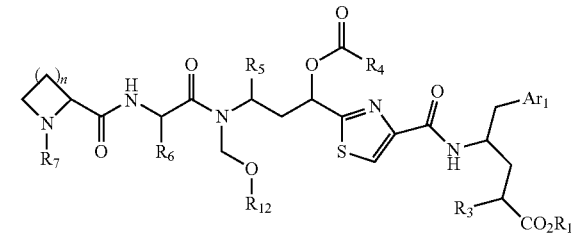

or a pharmaceutically acceptable salt thereof; wherein $Ar_1$ is optionally substituted aryl;

$R_1$ is hydrogen, alkyl, arylalkyl or a pro-drug forming group;

$R_{12}$ is alkyl, alkenyl, alkynyl, heteroalkyl, cycloalkyl, heterocycloalkyl, aryl, arylalkyl or heteroarylalkyl, each of which is optionally substituted;

$R_3$ is optionally substituted alkyl;

$R_4$ is optionally substituted alkyl or optionally substituted cycloalkyl;

$R_5$ and $R_6$ are each independently selected from the group consisting of optionally substituted alkyl and optionally substituted cycloalkyl; $R_7$ is optionally substituted alkyl; and n is 1, 2, 3, or 4.

The process of any one of the previous clauses comprising the step of treating compound D with a hydrolase enzyme or a trialkyltin hydroxide, where $R_8$ is $C_1$-$C_6$ unbranched alkyl, such as methyl, or arylalkyl, such as benzyl

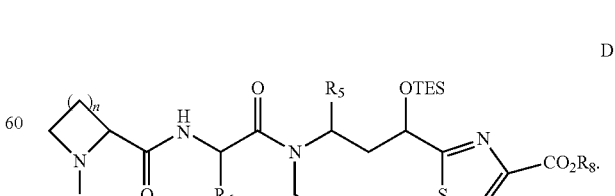

A compound of formula

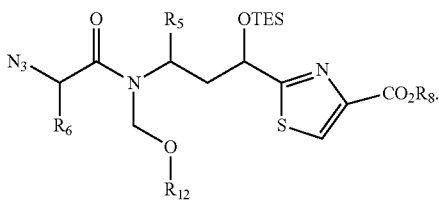

A compound of formula

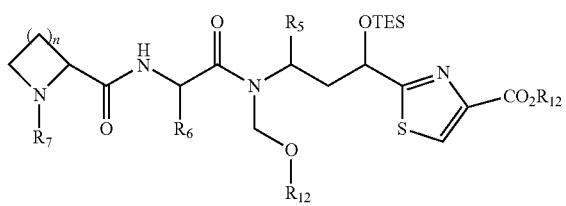

A compound of formula

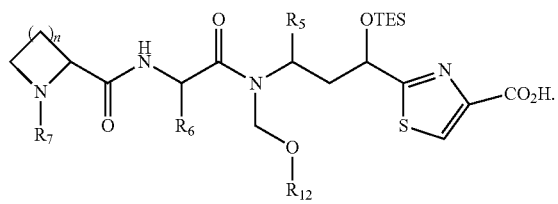

A compound of formula

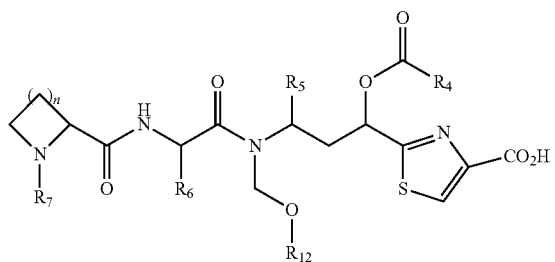

The process or compound of any one of the previous clauses wherein:

$R_1$ is hydrogen, alkyl, arylalkyl or a pro-drug forming group; and/or $R_2$ is selected from the group consisting of optionally substituted alkyl, optionally substituted cycloalkyl, and optionally substituted arylalkyl; and/or $R_2$ is selected from the group consisting of optionally substituted alkyl and optionally substituted cycloalkyl; and/or $R_7$ is optionally substituted alkyl.

The process or compound of any one of the previous clauses wherein $Ar_1$ is optionally substituted aryl.

The process or compound of any one of the previous clauses wherein $Ar_1$ is optionally substituted heteroaryl.

The process or compound of any one of the preceding clauses wherein $R_4$ is optionally substituted alkyl.

The process or compound of any one of the preceding clauses wherein $R_4$ is alkyl.

The process or compound of any one of the preceding clauses wherein $R_1$ is hydrogen, benzyl, or C1-C4 alkyl.

The process or compound of any one of the preceding clauses wherein $R_1$ is hydrogen.

The process or compound of any one of the preceding clauses wherein $R_2$ is $C_1$-$C_8$ alkyl or $C_3$-$C_8$ cycloalkyl.

The process or compound of any one of the preceding clauses wherein $R_2$ is n-butyl.

The process or compound of any one of the preceding clauses wherein $R_3$ is $C_1$-$C_4$ alkyl.

The process or compound of any one of the preceding clauses wherein $R_3$ is methyl.

The process or compound of any one of the preceding clauses wherein $R_4$ is C1-C8 alkyl or C3-C8 cycloalkyl.

The process or compound of any one of the preceding clauses wherein $R_4$ is methyl.

The process or compound of any one of the preceding clauses wherein $R_5$ is branched C3-C6 or C3-C8 cycloalkyl.

The process or compound of any one of the preceding clauses wherein $R_5$ is iso-propyl.

The process or compound of any one of the preceding clauses wherein $R_6$ is branched C3-C6 or C3-C8 cycloalkyl.

The process or compound of any one of the preceding clauses wherein $R_6$ is sec-butyl.

The process or compound of any one of the preceding clauses wherein $R_7$ is C1-C6 alkyl.

The process or compound of any one of the preceding clauses wherein $R_7$ is methyl.

The process or compound of any one of the preceding clauses wherein $R_2$ is $CH_2CH(CH_3)_2$, $CH_2CH_2CH_3$, $CH_2CH_3$, $CH{=}C(CH_3)_2$, or $CH_3$.

The process or compound of any one of the preceding clauses wherein $R_{12}$ is $CH_2CH{=}CH_2$, or $CH_2(CH_2)nCH_3$, where n=1, 2, 3, 4, 5, or 6.

The process or compound of any one of the preceding clauses wherein $R_{12}$ is $CH_2CH{=}CH_2$, $CH_2CH_2CH_2CH_3$, or $CH_2CH_2CH_2CH_2CH_3$ The process or compound of any one of the preceding clauses wherein $Ar_1$ is substituted phenyl.

The process or compound of any one of the preceding clauses wherein $Ar_1$ is $R_{Ar}$-substituted phenyl.

The process or compound of any one of the preceding clauses wherein $Ar_1$ is 4-substituted phenyl.

The process or compound of any one of the preceding clauses wherein $Ar_1$ is phenyl or hydroxyphenyl.

The process or compound of any one of the preceding clauses wherein $Ar_1$ is phenyl.

The process or compound of any one of the preceding clauses wherein $Ar_1$ is 4-hydroxyphenyl, or a hydroxyl protected form thereof.

The process or compound of any one of the preceding clauses wherein $Ar_1$ is 4-hydroxyphenyl.

The process or compound of any one of the preceding clauses wherein $Ar_1$ is 4-hydroxyphenyl where the 4-hydroxyl is in a protected form.

The process or compound of any one of the preceding clauses wherein $R_{13}$ is $CH_2CH_2CH_2CH_3$.

The process or compound of any one of the preceding clauses wherein L is —$(CR_2)_p CR^a R^b$—.

The process or compound of any one of the preceding clauses wherein L is —$(CR_2)_p CR^a R^b$—, p is 1, and each of $R^a$ and $R^b$ is methyl.

The process or compound of any one of the preceding clauses wherein L is

[chemical structure: *(CR$_2$)$_m$—phenyl—R$_{Ar}$*]

The process or compound of any one of the preceding clauses wherein L is

[chemical structure: *(CR$_2$)$_m$—phenyl—R$_{Ar}$, with * at other position]

The process or compound of any one of the preceding clauses wherein O-L-S is O—(CR$_2$)$_p$CR$^a$R$^b$—S.

The process or compound of any one of the preceding clauses wherein O-L-S is

[chemical structure: O—C(R)(R)—(CR$_2$)$_m$—phenyl(R$_{Ar}$)—S]

The process or compound of any one of the preceding clauses wherein O-L-S is

[chemical structure: O—C(R)(R)—(CR$_2$)$_m$—phenyl(R$_{Ar}$)—S with additional S]

The process or compound of any one of the preceding clauses wherein O-L-S is

[chemical structure: O—(C)$_m$—phenyl—S ortho]

The process or compound of any one of the preceding clauses wherein O-L-S is

[chemical structure: O—(C)$_m$—phenyl—S para]

The process or compound of any one of the preceding clauses wherein L is —(CR$_2$)$_p$CR$^a$R$^b$—, p is 1, and each of R$^a$ and R$^b$ is methyl.

The process or compound of any one of the preceding clauses wherein L is

[chemical structure: *H$_2$C—phenyl*]

The process or compound of any one of the preceding clauses wherein L is

[chemical structure: *H$_2$C—phenyl*]

The process or compound of any one of the preceding clauses wherein L is —(CH$_2$)$_p$CCH$_2$—.

The process or compound of any one of the preceding clauses wherein p is 2.

The process or compound of any one of the preceding clauses wherein p is 1.

The process or compound of any one of the preceding clauses wherein R$^a$ and R$^b$ are each hydrogen.

The process or compound of any one of the preceding clauses wherein m is 1.

The process or compound of any one of the preceding clauses wherein each R is hydrogen.

The process or compound of any one of the preceding clauses wherein R$^a$ is hydrogen and R$^b$ is methyl.

The process or compound of any one of the preceding clauses wherein R is hydrogen.

The process or compound of any one of the preceding clauses wherein R$^a$ and R$^b$ are each methyl.

The process or compound of any one of the preceding clauses wherein R$^a$ and R$^b$ are taken together with the attached carbon to form cyclopropyl.

The process or compound of any one of the preceding clauses wherein n is 3.

The process or compound of any one of the preceding clauses wherein R$_8$ is methyl.

The process or compound of any one of the preceding clauses wherein Ar$_2$ is optionally substituted aryl.

The process or compound of any one of the preceding clauses wherein Ar$_2$ is optionally substituted heteroaryl.

The process or compound of any one of the preceding clauses wherein Ar$_2$ is nitrophenyl or nitropyridine-2-yl.

The compound selected from the group consisting of

[chemical structures of two complex compounds shown at bottom of page]

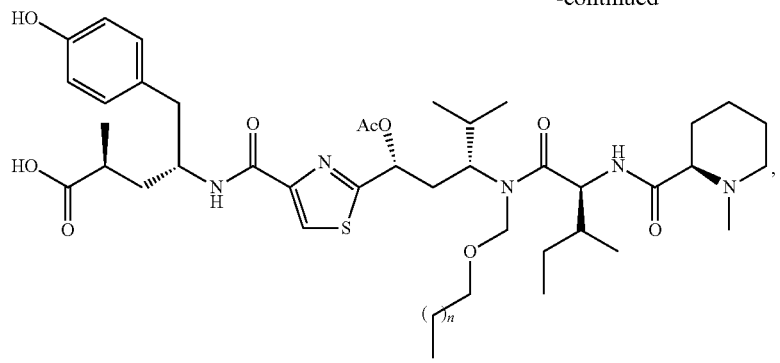
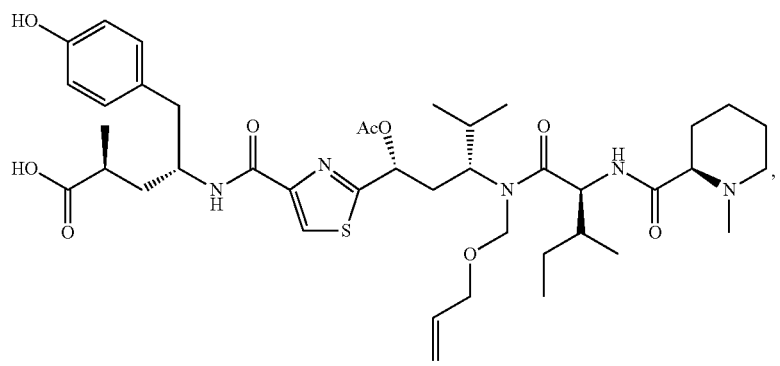
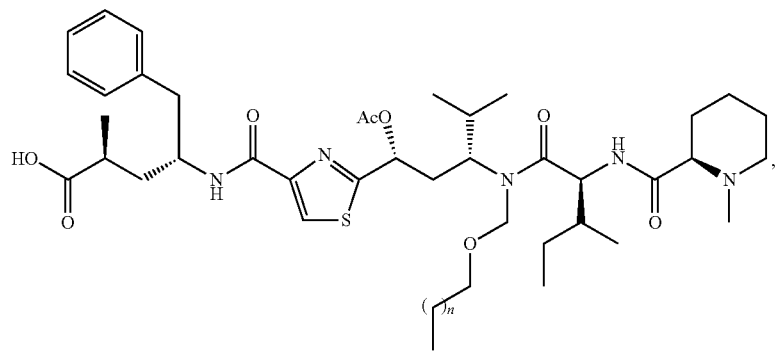
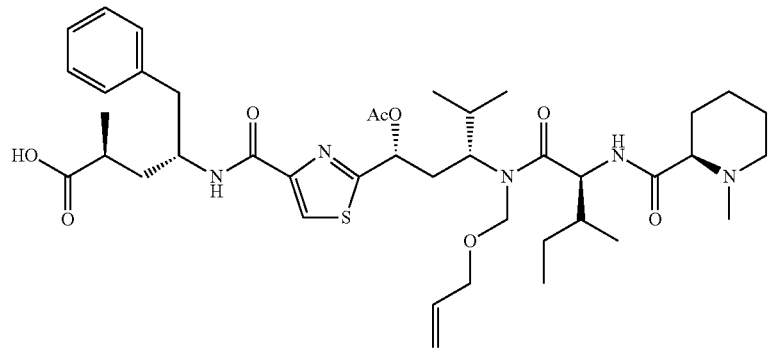

-continued
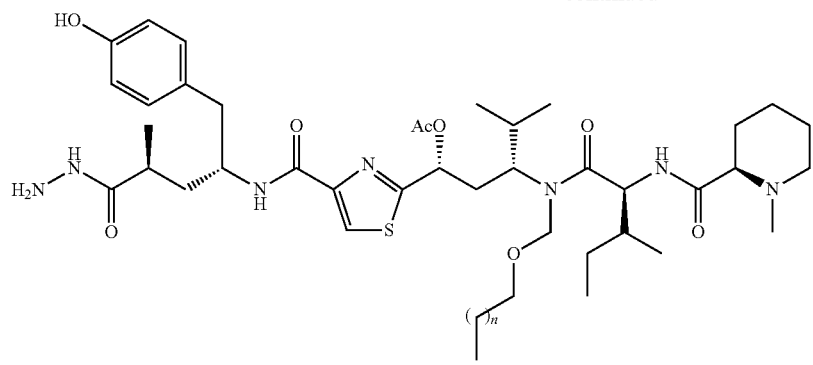
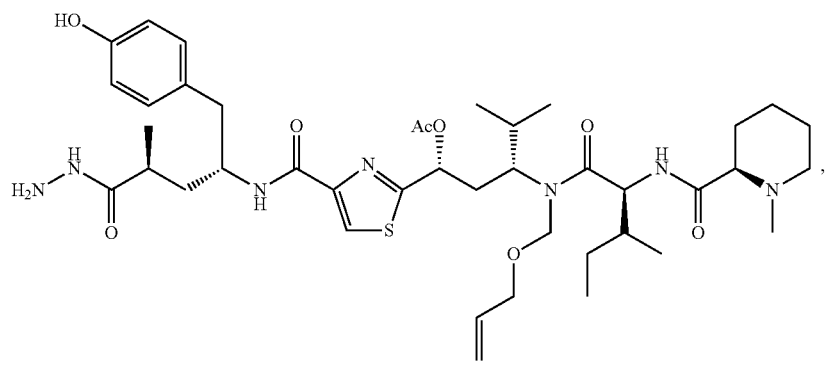
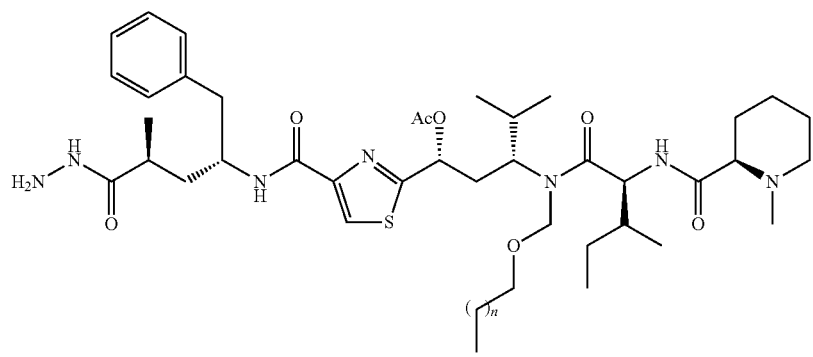
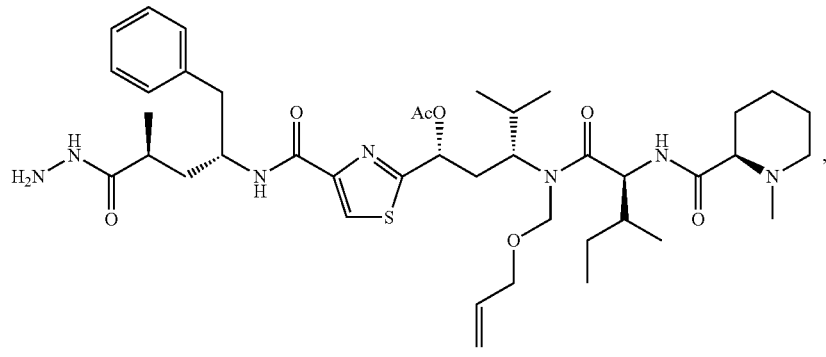

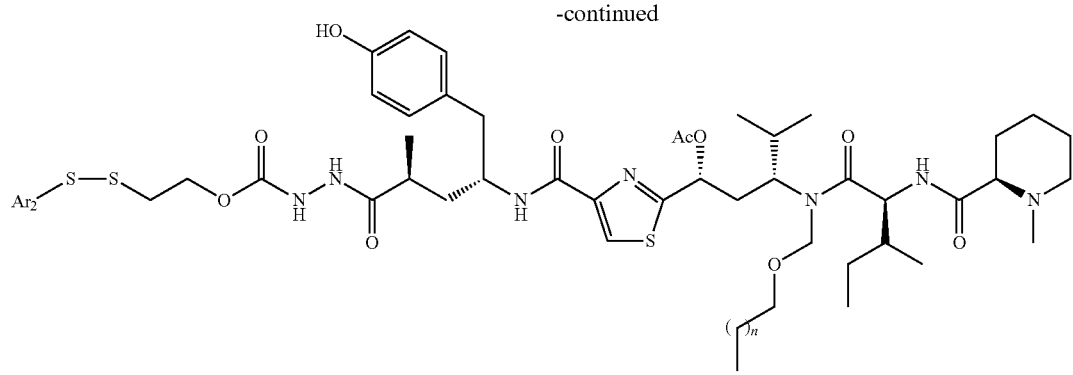

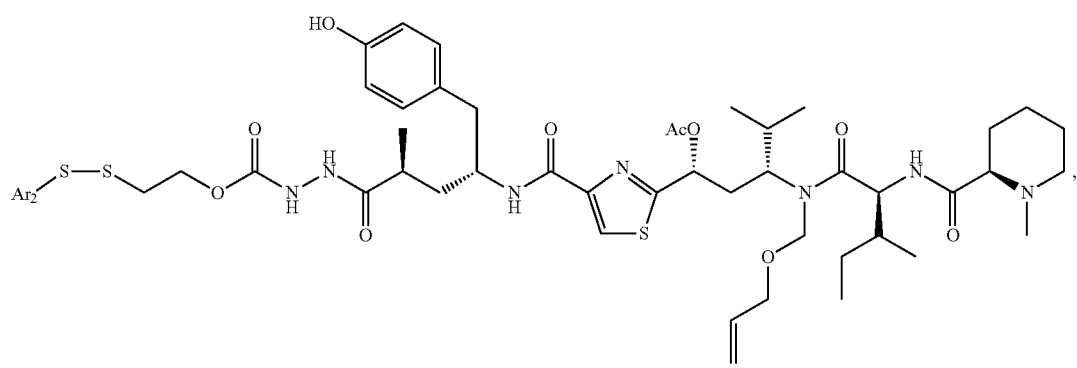

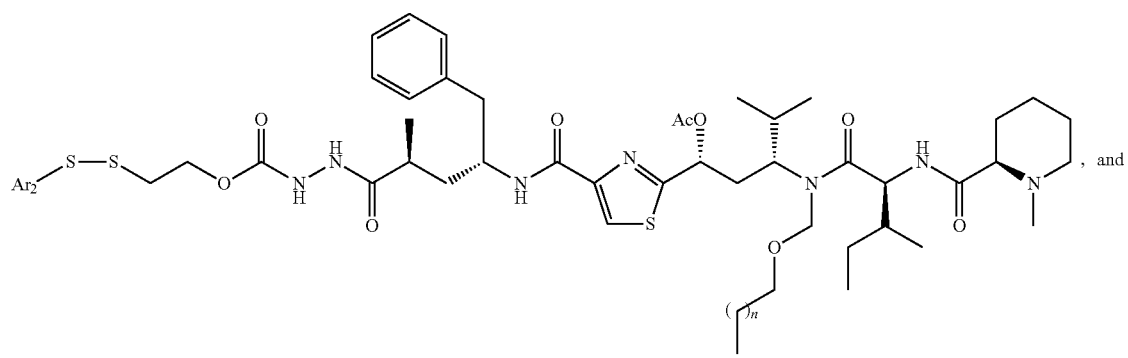

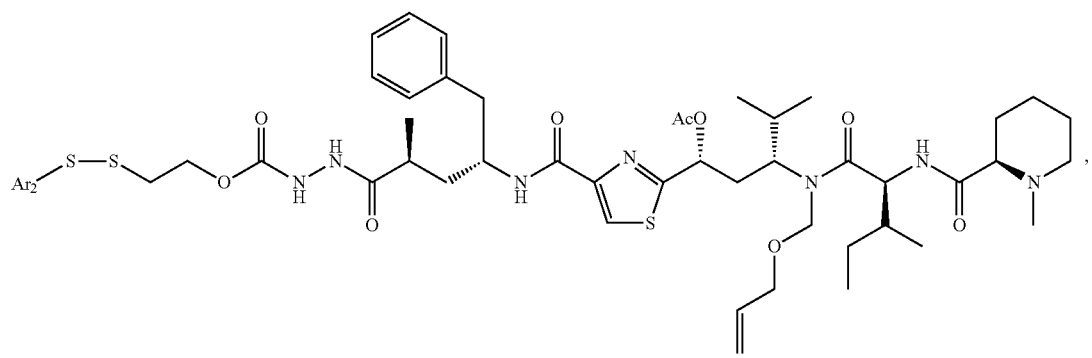

where n=1, 2, 3, 4, 5, or 6.

It is to be understood that as used herein, the term tubulysin refers both collectively and individually to the naturally occurring tubulysins, and the analogs and derivatives of tubulysins, including the tubulysins prepared using the processes described herein.

As used herein, the term tubulysin generally refers to the compounds described herein and analogs and derivatives thereof. It is also to be understood that in each of the foregoing, any corresponding pharmaceutically acceptable salt is also included in the illustrative embodiments described herein.

It is to be understood that such derivatives may include prodrugs of the compounds described herein, compounds described herein that include one or more protection or protecting groups, including compounds that are used in the preparation of other compounds described herein.

As used herein, the term "in a protected form" refers to the attachment to the functional group "in a protected form" of any protecting group for that functional group known to a person skilled in the art of organic synthesis.

In addition, as used herein the term tubulysin also refers to prodrug derivatives of the compounds described herein, and including prodrugs of the various analogs and derivatives thereof. In addition, as used herein, the term tubulysin refers to both the amorphous as well as any and all morphological forms of each of the compounds described herein. In addition, as used herein, the term tubulysin refers to any and all hydrates, or other solvates, of the compounds described herein.

It is to be understood that each of the foregoing embodiments may be combined in chemically relevant ways to generate subsets of the embodiments described herein. Accordingly, it is to be further understood that all such subsets are also illustrative embodiments of the invention described herein.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, (E)-, and (Z)-double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term aprotic solvent refers to a solvent which does not yield a proton to the solute(s) under reaction conditions. Illustrative examples of nonprotic solvents are tetrahydrofuran (THF), 2,5-dimethyl-tetrahydrofuran, 2-methyl-tetrahydrofuran, tetrahydropyran, diethyl ether, t-butyl methyl ether, dimethyl formamide, N-methylpyrrolidinone (NMP), and the like. It is appreciated that mixtures of these solvents may also be used in the processes described herein.

As used herein, an equivalent amount of a reagent refers to the theoretical amount of the reagent necessary to transform a starting material into a desired product, i.e. if 1 mole of reagent is theoretically required to transform 1 mole of the starting material into 1 mole of product, then 1 equivalent of the reagent represents 1 mole of the reagent; if X moles of reagent are theoretically required to convert 1 mole of the starting material into 1 mole of product, then 1 equivalent of reagent represents X moles of reagent.

As used herein, the term active ester forming agent generally refers to any reagent or combinations of reagents that may be used to convert a carboxylic acid into an active ester.

As used herein, the term active ester generally refers to a carboxylic acid ester compound wherein the divalent oxygen portion of the ester is a leaving group resulting in an ester that is activated for reacting with compounds containing functional groups, such as amines, alcohols or sulfhydryl groups. Illustrative examples of active ester-forming compounds are N-hydroxysuccinimide, N-hydroxyphthalimide, phenols substituted with electron withdrawing groups, such as but not limited to 4-nitrophenol, pentafluorophenol, N,N'-disubstituted isoureas, substituted hydroxyheteroaryls, such as but not limited to 2-pyridinols, 1-hydroxybenzotriazoles, 1-hydroxy-7-aza-benzotriazoles, cyanomethanol, and the like. Illustratively, the reaction conditions for displacing the active ester with a compound having an amino, hydroxy or thiol group are mild. Illustratively, the reaction conditions for displacing the active ester with a compound having an amino, hydroxy or thiol group are performed at ambient or below ambient temperatures. Illustratively, the reaction conditions for displacing the active ester with a compound having an amino, hydroxy or thiol group are performed without the addition of a strong base. Illustratively, the reaction conditions for displacing the active ester with a compound having an amino, hydroxy or thiol group are performed with the addition of a tertiary amine base, such as a tertiary amine base having a conjugate acid pKa of about 11 or less, about 10.5 or less, and the like.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic groups, including aromatic carbocyclic and aromatic heterocyclic groups, each of which may be optionally substituted. As used herein, the term "carbaryl" includes aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, acylcarbonyl, and the like, each of which is optionally substituted.

As used herein, the term "carboxylate and derivatives thereof" includes the group $CO_2H$ and salts thereof, and esters and amides thereof, and CN.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

Illustrative substituents include, but are not limited to, a radical —$(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from —$CO_2R^4$ and —$CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —NR$_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl$(C_2-C_{16})$alkanoyl; optionally substituted aroyl, such as unsubstituted aroyl or aroyl substituted by 1 to 3 substituents selected from the group consisting of halogen, cyano, trifluoromethanesulphonyloxy, $(C_1-C_3)$alkyl and $(C_1-C_3)$alkoxy, each of which is optionally further substituted with one or more of 1 to 3 halogen atoms; optionally substituted aryl$(C_2-C_{16})$alkanoyl, such as the aryl radical being unsubstituted or substituted by 1 to 3 substituents selected from the group consisting of halogen, $(C_1-C_3)$alkyl and $(C_1-C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

As used herein, the term "treating", "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

EXAMPLES

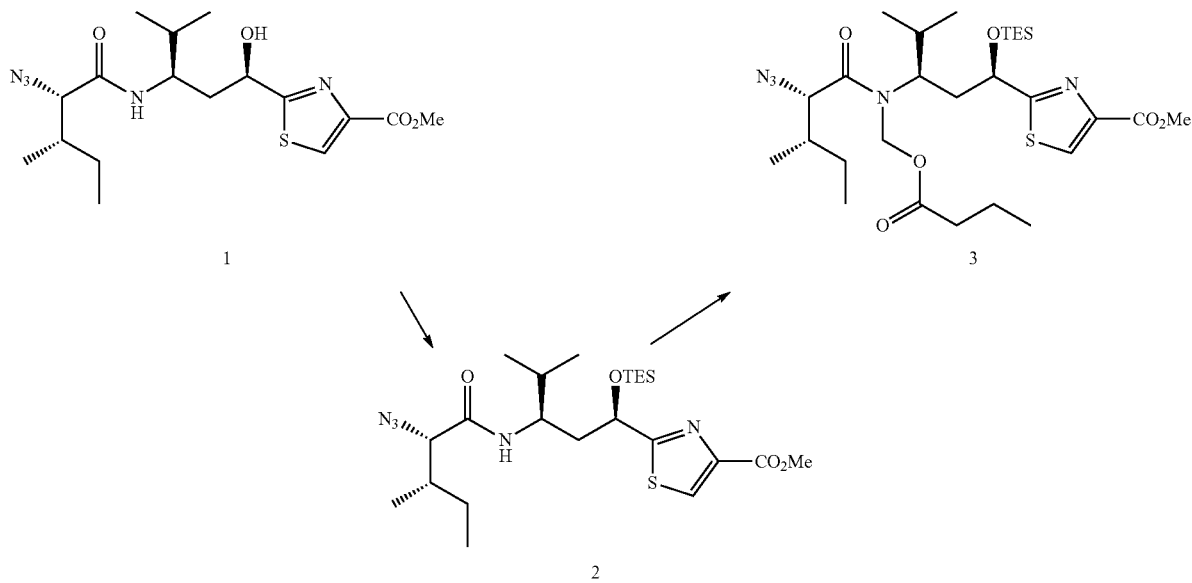

Synthesis of Dipeptide 3.

4.9 g of dipeptide 1 (11.6 mmol) was dissolved in 60 mL dichloromethane, imidazole (0.87 g, 12.7 mmol) was added to the resulting solution at 0° C. The reaction mixture was warmed slightly to dissolve all solids and re-cooled to 0° C. TESCl (2.02 mL, 12.1 mmol) was added drop-wise at 0° C., the reaction mixture was stirred under argon and warmed to room temperature over 2 h. TLC (3:1 hexanes/EtOAc) showed complete conversion. The reaction was filtered to remove the imidazole HCl salt, extracted with de-ionized water, and the aqueous phase was back-washed with dichloromethane, the combined organic phase was washed with brine, dried over $Na_2SO_4$, filtered to remove the $Na_2SO_4$, concentrated under reduced pressure, co-evaporated with toluene and dried under high-vacuum overnight to give 6.4 g of crude product 2 (vs 5.9 g of theoretical yield).

The crude product 2 was co-evaporated with toluene again and used without further purification. TES protected dipeptide was dissolved in 38 mL THF (anhydrous, inhibitor-free) and cooled to −45° C. and stirred for 15 minutes before adding KHMDS (0.5 M in toluene, 25.5 mL, 12.8 mmol, 1.1 equiv) drop-wise. After the addition of KHMDS was complete, the reaction mixture was stirred at −45° C. for 15 minutes, and chloromethyl butyrate (1.8 mL, 1.2 equiv, 14 mmol) was added. The reaction mixture changed from light yellow to a blueish color. TLC (20% EtOAc/petroleum ether) showed the majority of starting material was converted. LC-MS showed about 7% starting material left. The reaction was quenched by adding 3 mL MeOH, the mixture was warmed to room temperature and concentrated under reduced pressure to an oily residue. The residue was dissolved in petroleum ether and passed through short silica plug to remove the potassium salt. The plug was washed with 13% EtOAc/petroleum ether, and the collected eluates were combined and concentrated under reduced pressure. The crude alkylated product was passed through an additional silica plug (product/silica=1:50) and eluted with 13% EtOAc/petroleum ether to remove residual starting material to give 5.7 g of product 3 (two steps, yield 76%)

Large Scale Synthesis of Dipeptide 3.

10.2 g of dipeptide 1 (25.6 mmol) was dissolved in 130 mL dichloromethane, imidazole (1.9 g, 28.1 mmol) was added to the resulting solution at 0° C. The reaction mixture was warmed slightly to dissolve all solids and re-cooled to 0° C. TESCl (4.5 mL, 26.8 mmol) was added drop-wise at 0° C., the reaction mixture was stirred under argon and warmed to room temperature over 2 h. TLC (3:1 hexanes/EtOAc) showed complete conversion. The reaction was filtered to remove the imidazole HCl salt, extracted with de-ionized water, and the aqueous phase was back-washed with dichloromethane, the combined organic phase was washed with brine, dried over $Na_2SO_4$, filtered to remove the $Na_2SO_4$, concentrated under reduced pressure, co-evaporated with toluene and dried under high-vacuum overnight to give 12.2 g of product 2.

The crude product 2 was co-evaporated with toluene again and used without further purification. TES protected dipeptide was dissolved in 80 mL THF (anhydrous, inhibitor-free) and cooled to −45° C. and stirred for 15 minutes before adding KHMDS (0.5 M in toluene, 50 mL, 25.0 mmol, 1.05 equiv) drop-wise. After the addition of KHMDS was complete, the reaction mixture was stirred at −45° C. for 15 minutes, and chloromethyl butyrate (3.6 mL, 1.2 equiv, 28.3 mmol) was added. The reaction mixture changed from light yellow to a blueish color. TLC (20% EtOAc/petroleum ether) showed the reaction was complete. The reaction was quenched by adding 20 mL MeOH, the mixture was warmed to room temperature and concentrated under reduced pressure to an oily residue. The residue was dissolved in petroleum ether and passed through short silica plug to remove the potassium salt. The plug was washed with 13% EtOAc/petroleum ether, and the collected eluents were combined and concentrated under reduced pressure to give 12.1 g of product 3 (two steps, yield 76%)

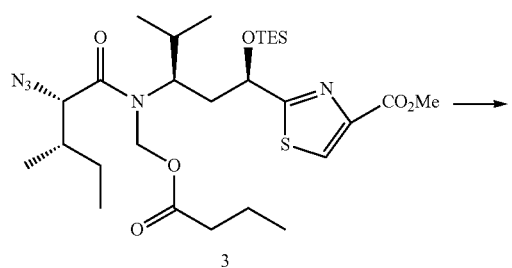

3

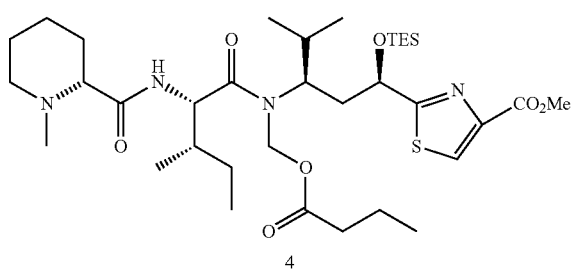

4

Synthesis of Tripeptide 4.

Alkylated dipeptide 3 (4.3 g, 7.0 mmol), N-methyl pipecolinate (MEP) (4.0 g, 28.0 mmol, 4 equiv) and pentafluorophenol (5.7 g, 30.8 mmol. 4.4 equiv) were added to a flask. N-methyl pyrrolidone (NMP, 86 mL) was added to the mixture. To the mixture was added diisopropylcarbodiimide (DIC, 4.77 mL, 30.8 mmol, 4.4 equiv) was added to the mixture. The mixture was stirred at room temperature for 1 h. Pd/C (10%, dry, 1.7 g) was added. The flask was shaken under hydrogen (30-35 psi) for 5 hours. The reaction mixture was analyzed by HPLC. The starting material was found to be less than 3%. The mixture was filtered through diatomaceous earth. The diatomaceous earth was extracted with 200 mL ethyl acetate. The filtrate and the ethyl acetate extract were combined and transferred to a separatory funnel and washed with 1% NaHCO₃/10% NaCl solution (200 mL×4). The organic layer was isolated and evaporated on a rotary evaporator under reduced pressure. The crude product was dissolved in 40 mL of MeOH/H₂O (3:1). The crude product solution was loaded onto a Biotage C18 column (Flash 65i, 350 g, 450 mL, 65×200 mm) and eluted with buffer A [10 mM NH₄OAc/ACN (1:1)] and B (ACN, acetonitrile). The fractions were collected and organic solvent was removed by evaporating on a rotary evaporator. 100 mL of 10% NaCl solution and 100 mL of methyl tert-butyl ether (MTBE) were added to the flask and the mixture was transferred to a separatory funnel. The organic layer was isolated and dried over anhydrous Na₂SO₄, filtered and evaporated on a rotary evaporator to dryness. 2.5 g of tripeptide intermediate 4 was obtained (yield 50%).

Large Scale Synthesis of Tripeptide 4.

Alkylated dipeptide 3 (7.6 g, 12.4 mmol), N-methyl pipecolinate (MEP) (7.0 g, 48.9 mmol, 4 equiv) and pentafluorophenol (10.0 g, 54.3 mmol. 4.4 equiv) were added to a flask. N-methyl pyrrolidone (NMP, 152 mL) was added to the mixture. To the mixture was added diisopropylcarbodiimide (DIC, 8.43 mL, 54.4 mmol, 4.4 equiv) was added to the mixture. The mixture was stirred at room temperature for 1 h. Pd/C (10%, dry, 3.0 g) was added. The flask was shaken under hydrogen (30-35 psi) for 5 hours. The reaction mixture was analyzed by HPLC. The reaction was complete. The mixture was filtered through celite. The celite was washed with 500 mL ethyl acetate. The solutions were combined and transferred to a separatory funnel and washed with 1% NaHCO₃/10% NaCl solution (250 mL×4). The organic layer was isolated and evaporated on a rotary evaporator under reduced pressure. The crude product was dissolved in dichloromethane and the urea was filtered. The crude product solution was loaded onto a Teledyne Redisep Silica Column (330 g) and purified with EtOAc/petroleum ether on CombiFlash flash chromatography system. The fractions were collected and organic solvent was removed by evaporating to give 5.0 g of the tripeptide (61%). NMR and mass spectral data were consistent with those measured for the Example.

The ether analog of compound 3 can also be prepared. Reductive condensation of that ether analog with MEP yields compound 10 directly.

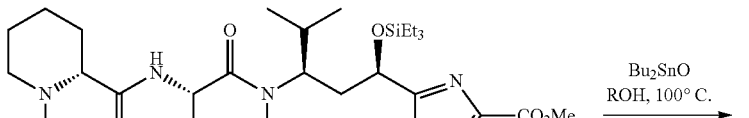

4

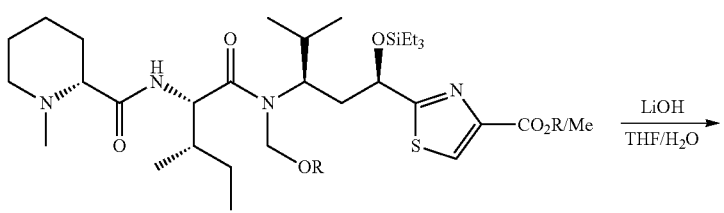

10

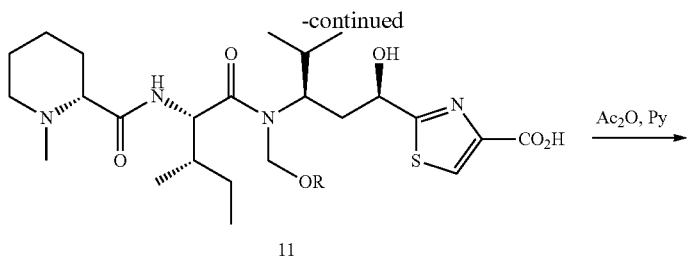

11

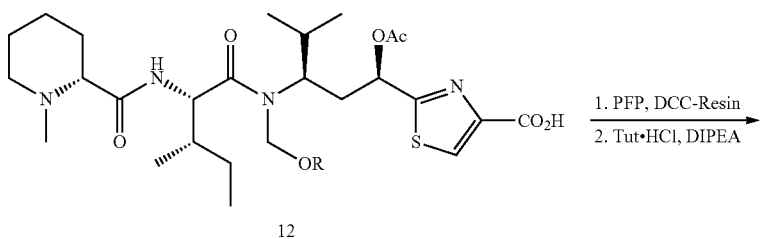

12

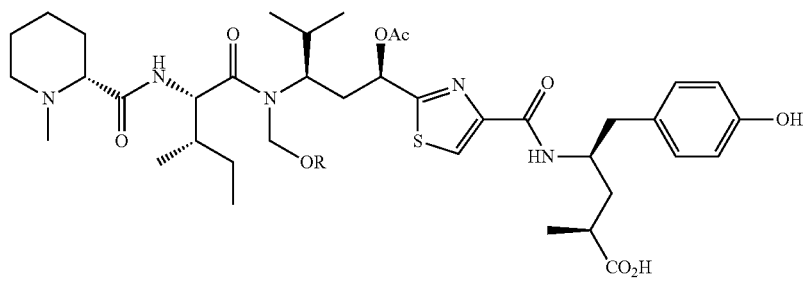

13

R: allyl, CH₂(CH₂)nCH₃
n = 1, 2, 3, 4, 5, or 6

R=allyl, alkyl, including $CH_2(CH_2)_nCH_3$, where n is 0, 1, 2, 3, 4, 5, or 6. Also described herein, is the conversion of 4 to 10 (R remains Me) by contacting 4 with TFA and an alcohol. In some illustrative examples of compound 10, R is allyl, or $CH_2(CH_2)nCH_3$, where n is 1, 2, 3, 4, 5, or 6.

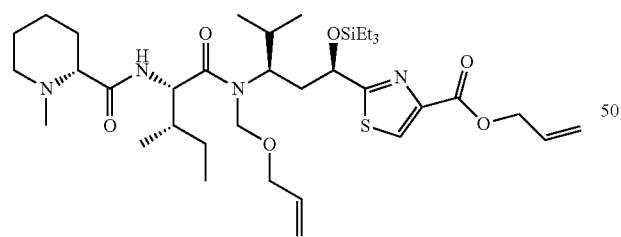

10a

Compound 4 (50 mg, 0.07 mmol) in allyl alcohol (5 mL) was treated with di-n-butyltin oxide (1.75 mg, 0.007 mmol, 10% mol). The reaction mixture was heated to reflux for 22 hrs till the reaction was complete. The reaction was concentrated and purified with HPLC in 10-100% ACN/ NH₃HCO₃ buffer (pH7.0) to give the title compound (32.4 mg, yield 65%). LCMS: [M+H]⁺ m/z=707.73. ¹H NMR (CD₃OD, δ in ppm): 8.35 (s, 1H), 6.01 (m, 2H); 5.2-5.5 (m, 3H), 5.14 (d, J=10.26 Hz, 1H), 5.04 (d, J=5.87 Hz, 1H), 4.88 (s, 3H), 4.82 (d, J=5.5 Hz, 2H), 4.70 (d, J=8.79 Hz, 1H), 4.50 (d, J=10.26 Hz, 1H), 4.42 (b, 1H), 4.06 (s, 2H), 2.92 (d, J=11.36 Hz, 1H), 2.55 (d, J=9.17 Hz, 1H), 1.95-2.20 (m, 7H), 1.45-1.82 (m, 7H), 1.22 (m, 2H), 0.82-1.00 (m, 17H), 0.77 (d, J=6.23 Hz, 3H), 0.59-0.70 (m, 6H); ¹³C NMR (CD₃OD, δ in ppm): 176.97, 175.08, 174.09, 160.95, 146.02, 134.13, 132.05, 127.94, 117.38, 116.37, 73.85, 70.32, 69.14, 68.40, 65.34, 56.89, 55.20, 53.55, 43.35, 40.37, 36.38, 31.59, 30.15, 24.80, 24.27, 22.93, 19.09, 18.71, 15.31, 9.52, 5.77, 4.41.

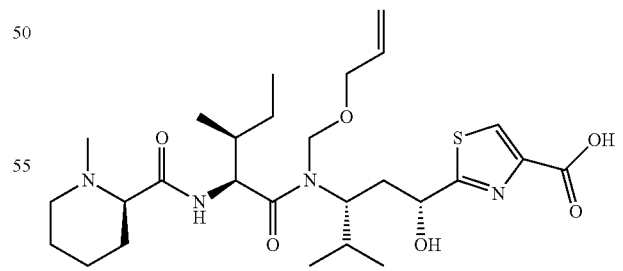

11a

Compound 10a (15.3 mg, 0.02 mmol) was subjected to hydrolysis with LiOH.H₂O (0.99 mg, 0.024 mmol) in 4:1 THF/H₂O (2.5 mL) for 19 hrs at room temperature (rt). The reaction was purified with HPLC in 10-100% ACN/ NH₃HCO₃ buffer (pH7.0) to provide compound 11a (9.2 mkg, yield 83%). LCMS: [M+H]⁺ m/z=553.55. ¹H NMR (CD₃OD, δ in ppm): 7.94 (s, 1H), 6.00 (m, 1H), 5.1-5.4 (m, 3H), 4.68 (d, J=9.09 Hz, 2H), 4.10 (d, J=3.81 Hz, 2H), 2.80 (b, 1H), 2.56 (s, 2H), 1.4-2.2 (m, 11H), 1.20 (m, 1H), 0.80-0.99 (m, 13H); $^{13}$C NMR (CD$_3$OD, δ in ppm): 17.90, 167.53, 153.18, 134.05, 123.09, 116.53, 68.63, 67.25, 54.85, 54.44, 42.10, 37.75, 36.53, 30.60, 29.13, 24.26, 23.25, 21.37, 20.32, 19.53, 14.72, 9.51.

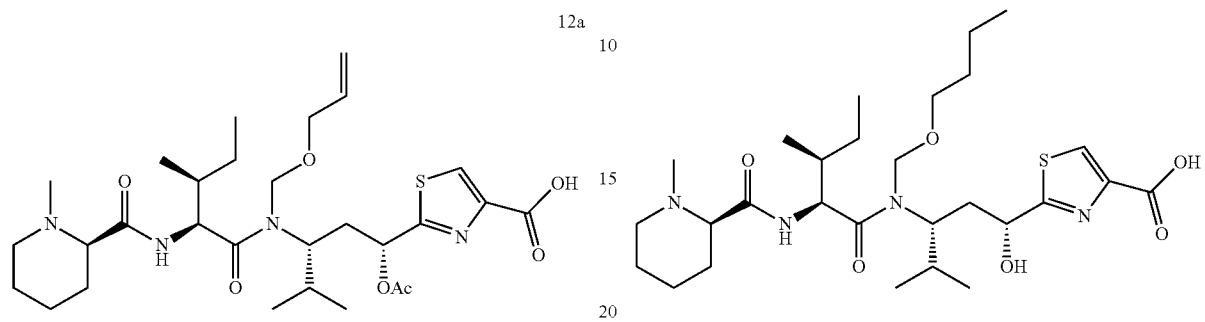

12a

To compound 11a (9.2 mg, 0.017 mmol) in pyridine (1 mL) was added acetic anhydride (15.7 μL, 0.165 mmol) and a catalytic amount of 4-dimethylamino pyridine (0.053 M in pyridine, 5 μL) at rt under argon. The reaction was stirred for 24 hrs. To the reaction mixture was added 0.4 mL of dioxane/water (1:1) and stirred for 10 min, and then the solvent was removed in vacuo. The residue was purified with HPLC in 10-100% ACN/NH$_3$HCO$_3$ buffer (pH7.0) to provide the product 12a 10.4 mg (quantitative yield). LCMS: [M+H]$^+$ m/z=595.59. $^1$H NMR (CD$_3$OD, δ in ppm): 7.96 (s, 1H), 5.8-6.0 (m, 2H), 5.33 (d, J=17.59 Hz, 1H), 5.19 (d, J=10.56 Hz, 1H), 4.71 (d, J=9.23 Hz, 2H), 4.05 (d, J=5.71 Hz, 2H), 3.30 (m, 6H), 2.50 (b, 4H), 2.10 (s, 3H), 1.40-2.00 (m, 7H), 1.20 (m, 1H), 0.80-1.02 (m, 11H); $^{13}$C NMR (CD$_3$OD, δ in ppm): 175.11, 170.44, 167.29, 153.45, 133.92, 123.40, 116.79, 116.55, 68.62, 67.82, 67.11, 54.75, 54.16, 42.39, 36.31, 36.12, 34.91, 30.55, 29.26, 24.09, 23.26, 21.25, 20.24, 19.48, 19.20, 14.78, 9.56.

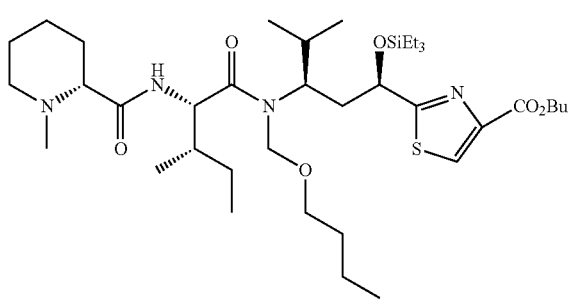

10b

Compound 4 (75.9 mg, 0.11 mmol) in n-butanol (4 mL) was treated with n-Bu$_2$SnO (2.12 mg, 0.0085 mmol, 8.0 mol %) at rt and the reaction was heated to 100° C. for 2 days. The solvent was reduced to a minimum and the product was purified with CombiFlash (Teledyne Redisep Silica column, eluted with 0 to 15% of MeOH/DCM) to give 44.0 mg (56%) of intermediate 10b. LCMS: [M+H]$^+$ m/z=739.61. $^1$H NMR (CDCl$_3$, δ in ppm): 8.07 (s, 1H), 7.02 (d, J=9.68 Hz, 1H), 5.27 (d, J=9.67 Hz, 1H), 5.02 (dd, J=8.36, 2.64 Hz, 1H), 4.69 (t, J=9.23 Hz, 4.20-4.40 (m, 4H), 3.47 (td, J=6.6, 1.76 Hz, 2H), 2.88 (d, J=11.44 Hz, 1H), 2.46 (dd, J=10.55, 3.08 Hz, 2H), 1.90-2.24 (m, 8H), 1.10-1.79 (m, 18H), 0.80-1.00 (m, 19H), 0.58-0.78 (m, 6H).

11b

The same procedure as compound 11a was followed. 11b (11.7 mg, 35%) was obtained from intermediate 10b (44.0 mg). LCMS: [M+H]$^+$ m/z=569.51. $^1$H NMR (CDCl$_3$ drops of CD$_3$OD, δ in ppm) 8.00 (s, 1H), 5.23 (b, 1H), 4.80 (b, 1H), 4.58 (d, J=8.80 Hz, 1H), 4.42 (b, 1H), 3.45 (t, J=6.38 Hz, 1H), 3.33 (b, 3H), 2.15-2.40 (m, 3H), 1.80-2.10 (m, 2H), 1.40-1.79 (m, 4H), 1.04-1.38 (m, 3H), 0.60-1.02 (m, 9H).

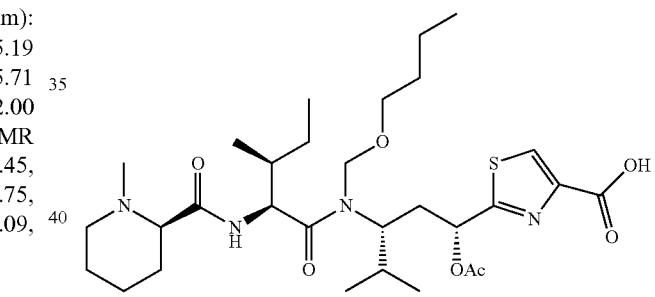

12b

In a 10 mL round bottom flask, 11b (11.7 mg, 0.021 mmol) and acetic anhydride (20 μL, 0.212 mmol) were dissolved in pyridine (1 mL). To this solution was added a catalytic amount of dimethylaminopyridine (1 mg, 0.008 mmol). This solution was stirred at room temperature for 16 h under Argon. LCMS (10-100% ACN, 50 mM NH$_4$HCO$_3$ pH7) indicated all of the starting material had been consumed and product had been formed. To the flask was added a 1:1 mixture of 1,4-dioxane and water (0.4 mL) and the solution was stirred for 10 min to hydrolyze any potential diacetate side product. The reaction mixture was concentrated under reduced pressure, then purified by preparative HPLC (10-100% ACN, 50 mM NH$_4$HCO$_3$ pH7) to yield 12b (9.6 mg, 76%). LCMS: [M+H]$^+$=611.53. $^1$H NMR (CDCl$_3$ w/2 drops CD$_3$OD): 7.97 (s, 1H) 5.83 (d, J=9.9 Hz, 1H) 5.28 (s, 1H) 4.58 (d, J=9.0 Hz, 1H) 4.24 (d, J=9.3 Hz, 2H) 3.42 (m, 3H) 2.60-2.95 (br, 7H) 2.20-2.58 (br, 6H) 1.76-2.20 (br, 11H) 1.40-1.56 (br, 12H) 1.02-1.20 (br, 12H) 0.40-1.10 (br, 27H) 0.04 (s, 8H). $^{13}$C NMR: 175.04, 170.53, 67.78, 53.74, 44.33, 36.79, 35.64, 31.69, 29.89, 24.86, 20.96, 20.49, 19.52, 15.95, 13.99, 10.65, 1.21

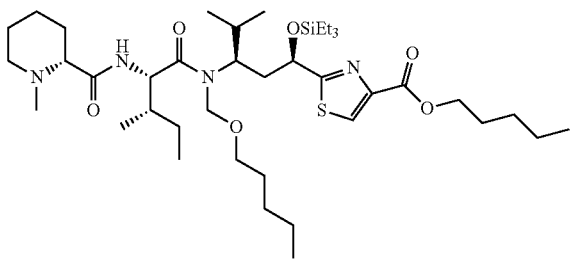

10c

Compound 4 (73.9 mg, 0.10 mmol) in n-pentanol (4 mL) was treated with n-Bu₂SnO (2.10 mg, 0.0083 mmol, 8.0 mol %) at rt and the reaction was heated to 100° C. for 2 days. The solvent was reduced to a minimum and the product was purified with CombiFlash (Teledyne Redisep Silica column, eluted with 0 to 15% of MeOH/DCM) to give 51.2 mg (64%) of intermediate 10b. LCMS: [M+H]⁺ m/z=767.64. ¹H NMR (CDCl₃, δ in ppm): 8.07 (m, 1H), 7.06 (t, J=9.23 Hz, 1H), 5.95 (d, J=12.3 Hz, 1H), 5.43 (d, J=12.32 Hz, 1H), 5.26 (d, J=9.68 Hz, 1H), 5.03 (dd, J=8.36, 2.64 Hz, 1H), 4.93 (dd, J=8.36, 6.24 Hz, 1H), 4.71 (dd, J=15.83, 8.80 Hz, 1H), 4.20-4.33 (m, 3H), 3.46 (m, 1H), 2.88 (d, J=11.43 Hz, 1H), 2.30-2.60 (m, 2H), 2.20 (s, 2H), 1.95-2.18 (m, 3H), 1.50-1.80 (m, 6H), 1.10-1.44 (m, 6H), 0.80-1.04 (m, 13H), 0.50-0.77 (m, 6H).

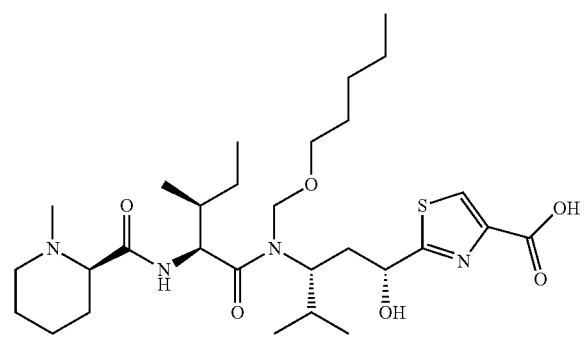

11c

The same procedure as for compound 11a was followed, intermediate 11c (14.9 mg, 38%) was obtained from 10c (51.2 mg). LCMS: [M+H]⁺ m/z=583.56. ¹H NMR (CD₃OD, δ in ppm): 7.97 (s, 1H), 5.27 (d, J=9.67 Hz, 1H), 4.67 (d, J=9.23 Hz, 1H), 4.58 (d, J=9.68 Hz, 1H), 3.53 (m, 3H), 2.80 (b, 1H), 2.58 (b, 4H), 1.48-2.18 (m, 13H), 1.10-1.42 (m, 6H), 0.70-1.08 (m, 18H).

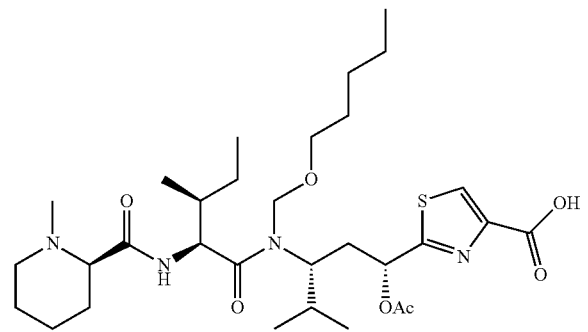

12c

In a 10 mL round bottom flask, 11c (14.9 mg, 0.026 mmol) and acetic anhydride (20 µL, 0.212 mmol) were dissolved in pyridine (1 mL). This solution was added a catalytic amount of dimethylaminopyridine (1 mg, 0.008 mmol). This solution was stirred at room temperature for 16 h under argon. LCMS (10-100% ACN, 50 mM NH₄HCO₃ pH7) indicated all of the starting material had been consumed and product had been formed. To the flask was added a 1:1 mixture of 1,4-dioxane and water (0.4 mL) and the solution was stirred for 10 min to hydrolyze any potential diacetate side product. The reaction mixture was concentrated under reduced pressure, then purified by preparative HPLC (10-100% ACN, 50 mM NH₄HCO₃ pH7) to yield 12c (4.8 mg, 30%). LCMS: [M+H]⁺ m/z=625.58. ¹H NMR (CDCl₃ w/2 drops CD₃OD) 7.98 (s, 1H) 5.82 (d, J=10.8 Hz, 1H) 5.26 (s, 1H) 4.57 (d, J=8.4 Hz, 1H) 4.23 (d, J=8.4 Hz, 2H) 3.42 (m, 3H) 2.60-2.92 (br, 8H) 2.15-2.40 (br, 4H) 1.90-2.12 (m, 7H) 1.38-1.90 (br, 14H) 1.00-1.38 (br, 13H) 0.50-1.00 (br, 22H), 0.03 (s, 13H). ¹³C NMR: 175.15, 150.56, 125.47, 69.55, 68.09, 55.33, 53.71, 44.59, 36.77, 35.74, 31.34, 30.19, 29.86, 29.32, 28.51, 24.84, 22.85, 22.55, 20.86, 20.40, 19.91, 15.94, 14.10, 10.63, 1.17

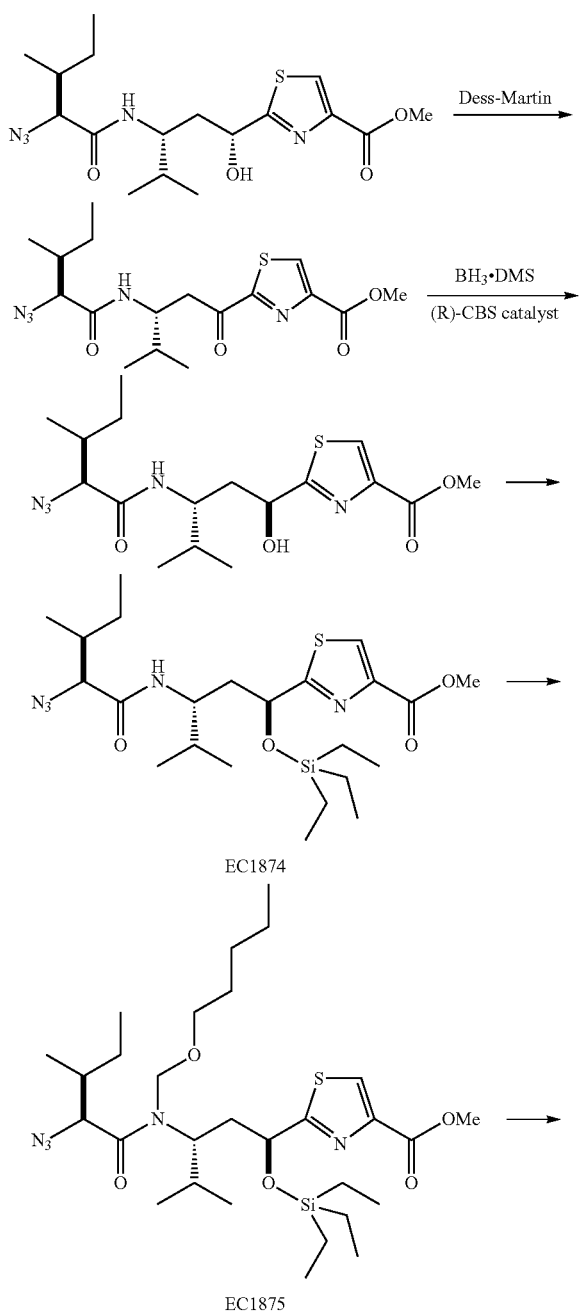

-continued

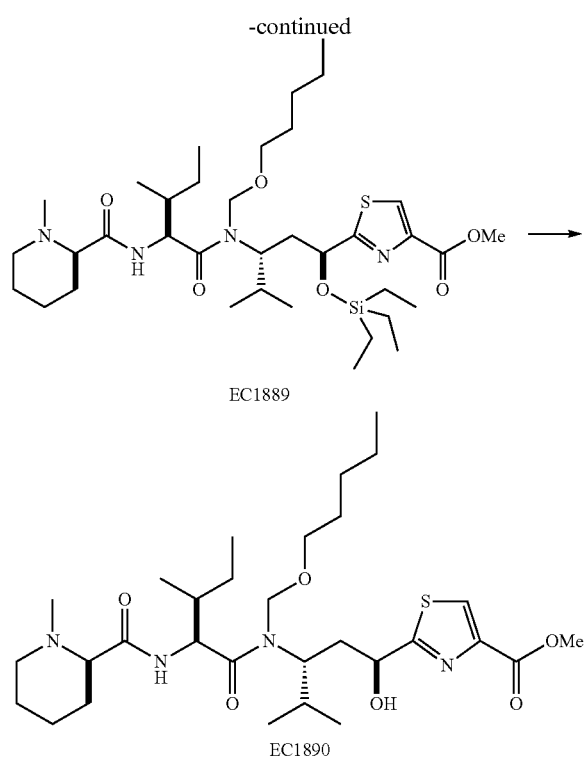

Synthesis of EC1890. 1.76 g (4.43 mmol) of dipeptide was dissolved in 40 mL of DCM and 1.8 g (21.43 mmol, 4.8 equiv.) of NaHCO₃, followed by 1.97 g (4.64 mmol, 1.05 equiv.) of Dess-Martin reagent were added at 0° C. The reaction was stirred at 0° C. for 1 hour. The reaction was partitioned between 10% Na₂SO₃ aqueous solution and DCM. The organic layer was washed with brine, dried over Na₂SO₄, and concentrated to give 1.75 g of the product. The crude product was used without further purification.

1.75 g of ketone (4.42 mmol) was dissolved in 15 mL of THF and 122 mg of (R)-CBS catalyst (0.1 equiv.) followed by 2.5 mL of 2 M BH₃.DMS in THF (1.1 equiv.) were then added at 0° C. After 3 hours, the reaction was partitioned between EtOAc and water. The organic layer was then washed with brine, dried over Na₂SO₄, and concentrated. Purification by SiO₂ column (Combiflash®) via gradient elution (EtOAc and pet. ether mobile phase) gave 0.963 g (55%) of the 5-(S)-isomer.

0.963 g of 5-(S)-dipeptide (2.42 mmol) was dissolved in 12 mL DCM and 181 mg of imidazole (2.62 mmol, 1.1 equiv.) was added to the solution. The mixture was cooled to 0° C., and then 0.43 mL of TESCl (2.56 mmol, 1.05 equiv.) was added. After 3 hrs, LC/MS showed about 40% of the starting material converted. An additional 127 mg of imidazole (1.87 mmol, 0.77 equiv.) and 0.3 mL TESCl (1.79 mmol, 0.74 equiv.) were added. After 1 hr, LC/MS showed completed conversion. The reaction was diluted with DCM and washed with water and brine, and then dried over Na₂SO₄ and concentrated. Purification by SiO₂ column (Combiflash®) via gradient elution (EtOAc and pet. ether mobile phase) gave 1.1 g (89%) of EC1874.

1.1 g of EC1874 (2.15 mmol) was dissolved in 8 mL of THF (anhydrous, inhibitor-free) and cooled to −45° C. 4.5 mL of KHMDS (0.5 M in toluene, 2.26 mmol, 1.05 equiv.) was added to the solution. After 15 minutes, 463 µL of bromomethyl pentyl ether (1.5 equiv.) was added at −45° C. After 30 minutes, the reaction was quenched with 10% NaCl/1% NaHCO₃ aqueous solution, extracted with EtOAc, washed with 10% NaCl/1% NaHCO₃ aqueous solution and then brine, dried over Na₂SO₄, and concentrated under reduced pressure. Purification by SiO₂ column (Combiflash®) via gradient elution (EtOAc and pet. ether mobile phase) gave 0.56 g (43%) of EC1875.

92 mg of MEP (0.64 mmol, 1.56 equiv.) was added to 1.0 mL of NMP in a hydrogenation flask. 127 mg of PFP (0.69 mmol, 1.68 equiv.) and 132 mg of EDC (0.69 mmol, 1.68 equiv.) were added and the reaction was stirred overnight at room temperature. 250 mg (0.41 mmol) of alkylated dipeptide methyl ether EC1875 in 1.0 mL NMP was transferred to the hydrogenation flask, and 34 mg of 10% Pd/C (dry, 0.05 equiv.) was added. The reaction was shaken under an atmosphere of hydrogen at 35 PSI for 2 hours. LC/MS showed no dipeptide left. The reaction mixture was filtered through celite and the filter cake washed with EtOAc. The filtrate was washed with a 10% NaCl-1% Na₂CO₃ aqueous solution (3 times) and brine, dried over Na₂SO₄, and concentrated under reduced pressure. Purification by SiO₂ column (Combiflash®) via gradient elution (DCM and MeOH mobile phase) gave 100 mg of EC1889 (34%).

100 mg of EC1889 (0.141 mmol) was dissolved in 0.6 mL of THF (anhydrous) and 25 µL of 3 HF.Et₃N (0.153 mmol) was added at room temperature. After 1 hour, LC/MS showed the complete conversion. Purification by SiO₂ column (Combiflash®) via gradient elution (DCM and MeOH mobile phase) gave 68 mg (81%) of EC1890.

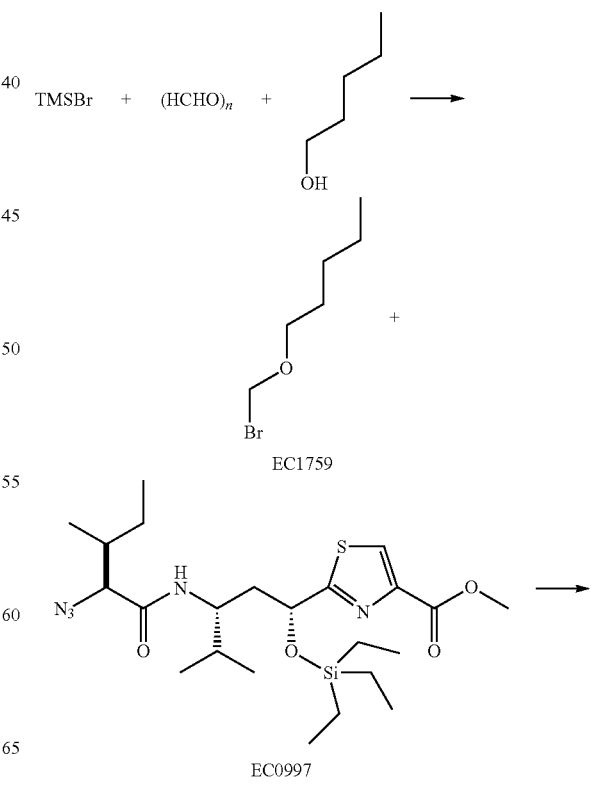

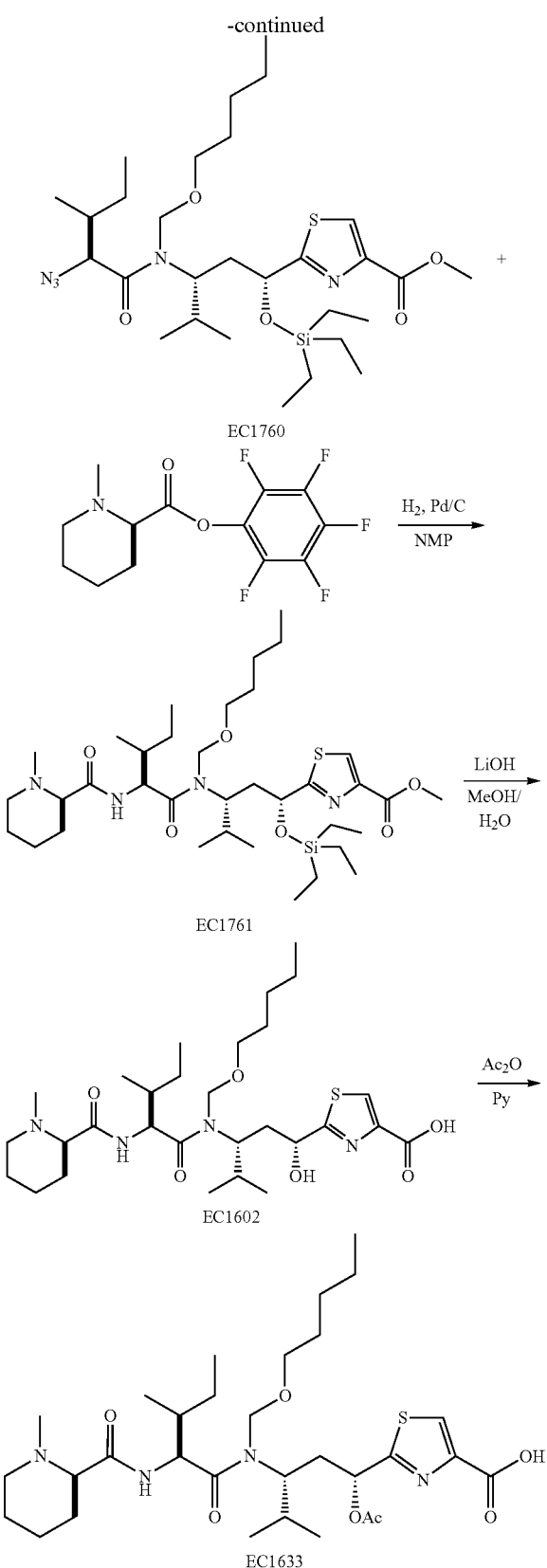

C. and warmed up to room temperature. After overnight, TMSBr was evaporated under reduced pressure. Vacuum distillation of the residue was carried out at 7 mm Hg pressure, the fraction came out at 56° C. was the desired product EC1759 (4.3 g, 59%).

Synthesis of EC1760

1.58 g (3.09 mmole) TES-dipeptide EC0997 was dissolved in 12 mL THF (anhydrous, inhibitor-free). The resulted solution was cooled to −45° C. To the solution, 6.5 mL of 0.5 M KHMDS in toluene (3.25 mmole, 1.05 equiv.) was added dropwise. After finishing the addition, the reaction mixture was stirred at −45° C. for 15 minutes. 600 μL of bromomethyl pentyl ether EC1759 (4.1 mmole, 1.33 equiv.) was added dropwise. The reaction mixture was warmed from −45° C. to −10° C. in 90 minutes, then quenched with 10% NaCl/1% NaHCO$_3$ aqueous solution, extracted with EtOAc. The organic phase was washed with 10% NaCl/1% NaHCO$_3$ aqueous solution three times, then brine. The separated organic phase was dried over Na$_2$SO$_4$. Na$_2$SO$_4$ was filtered off and the solvent was evaporated under vacuum to give 2.4 g of crude product. The crude product was purified with EtOAc/petroleum ether to give 1.47 g of product EC1760 (78%)

Synthesis of EC1761

0.38 g of MEP (2.65 mmole, 1.4 equiv.) was suspended in 1.2 mL NMP, 0.53 g of PFP (2.88 mmole, 1.5 equiv.) and 0.55 g of EDC (2.87 mmole, 1.5 equiv.) were added. The reactionmixture was stirred overnight in a hydrogenation vessel. 1.17 g (1.91 mmole) of alkylated dipeptide EC1760 was dissolved in 0.3 mL NMP and transferred to the above hydrogenation vessel, and the residue of the dipeptide was rinsed with 0.3 mL NMP and transferred to the hydrogenation vessel. 154 mg of 10% Pd/C (dry, 0.05 equiv.) was added to the solution. The hydrogenation was carried out at 35 PSI. After 5 hrs, LC/MS showed there was no starting material. The reaction mixture was filtered through celite pad and the reaction vessel was washed with EtOAc and filtered through celite pad. The combined solution was washed with 10% NaCl/1% Na$_2$CO$_3$ solution to remove PFP, then with brine. The organic phase was dried over Na$_2$SO$_4$. Na$_2$SO$_4$ was filtered off and the solvent was evaporated under vacuum to give 1.20 g (88%) of crude product EC1761.

Synthesis of EC1602

1.17 g (1.65 mmole) of tripeptide ester EC1761 was dissolved in 15 mL MeOH, the solution was cooled to 0° C. 300 mg of LiOH hydrate (7.15 mmole, 4.3 equiv.) dissolved in 5 mL H$_2$O was added to the ester solution, the resulted reaction mixture was stirred and warmed up to room temperature in 2 hours. LC/MS showed no starting material left. MeOH was removed using rotary evaporator, and the residual was worked up by extraction between EtOAc/brine. The organic phase was dried over Na$_2$SO$_4$. Na$_2$SO$_4$ was filtered off and the solvent was evaporated under vacuum to give 0.80 g (83%) of crude product EC1602.

Synthesis of EC1633

0.80 g (1.37 mmole) of tripeptide acid EC1602 was dissolved in 6.4 mL of pyridine, the solution was cooled to 0° C. 6.0 mg (0.049 mmole, 0.035 equiv) DMAP was added and then 2 mL of acetic anhydride (21.2 mmole, 15.5 equiv) was added, the reaction mixture was warmed up to room temperature in 5 hours and stored in −20 0° C. for 2 days. 20 mL dioxane/20 mL H2O was added to the reaction mixture at 0° C. and stirred for 1 hour. The solvent was evaporated under reduced pressure. 20 mL of phosphate buffer (20 mM) and 5 mL acetonitrile were added to the residue, the pH of the resulted solution was adjusted to 5.4 using saturated NaHCO$_3$ solution. The solution was loaded on Biotage 120 g C18 column. The flask containing the crude product was rinsed with 1 mL acetonitrile/5 mL phosphate buffer and loaded on the column. The purification was done using a gradient from 20% ACN/80% water to 70% ACN/30%. The fractions containing the desired product were combined and ACN was evaporated under reduced pressure, resulting in the formation of a white precipitate. Brine was added to the suspension and EtOAc was used to extract the desired product. The organic phase was dried over Na₂SO₄. Na₂SO₄ was filtered off and the solvent was evaporated under vacuum to give 0.49 g (57%) of product EC1633.

In a 25 mL round bottom flask, 12b (9.6 mg, 0.016 mmol) and pentafluorophenol (28.2 mg, 0.153 mmol) were dissolved in dry dichloromethane (5 mL). N-cyclohexylcarbodiimide, N'-methyl polystyrene (33.4 mg, 2.3 mmol/g, 0.077 mmol) was added and the reaction mixture was stirred at room temperature for 16 h under Argon. LCMS (10-100% ACN, 50 mM NH₄HCO₃ pH7) indicated all of the starting material had been consumed and activated intermediate had

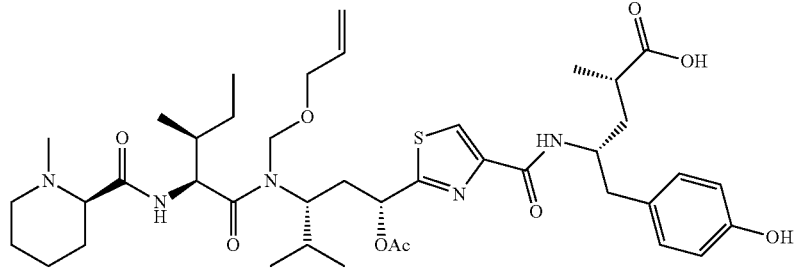

13a

Compound 12a (10.4 mg, 0.017 mmol) was dissolved in anhydrous methylene chloride (4 mL) and to this solution was added DCC-resin (2.3 mmol/g, 0.038 g, 0.087 mmol) and followed by pentafluorophenol (PFP, 6.26 mg, 0.034 mmol) at rt under argon. The reaction was stirred for 19 hrs at rt. The reaction mixture was filtered and the solution was concentrated. The residue was redissolved in dry DMF (4 mL). Then, (2S,4R)-4-amino-5-(4-hydroxyphenyl)-2-methylpentanoic acid (Tut acid) was added into the solution, followed by DIPEA (8.9 μL, 0.051 mmol). When completed, the reaction was concentrated in vacuo and the residue was purified with HPLC. Product 13a was obtained (13.1 mg, 96% yield). LCMS: [M+H]⁺ m/z=800.88. ¹H NMR (CD₃OD, δ in ppm): 8.08 (s, 1H), 7.02 (d, J=8.43 Hz, 2H), 6.68 (d, J=8.06 Hz, 2H), 5.99 (d, J=10.99 Hz, 1H), 5.80 (m, 1H), 5.38 (d, J=9.53 Hz, 1H), 5.31 (d, J=17.23 Hz, 1H), 5.13 (d, J=10.63 Hz, 1H), 4.66 (d, J=8.79 Hz, 1H), 4.55 (d, J=10.28 Hz, 1H), 4.30 (b, 2H), 4.00 (b, 2H), 3.16 (b, 2H), 2.80 (d, J=5.86 Hz, 2H), 2.40 (b, 4H), 2.10-2.30 (b, 2H), 1.40-1.90 (b, 6H), 1.23 (s, 3H), 1.17 (d, J=6.96 Hz, 3H), 1.05 (d, J=6.23 Hz, 2H), 0.94 (d, J=6.97 Hz, 2H), 0.90 (d, J=7.70 Hz, 2H), 0.79 (d, J=6.6 Hz, 3H); ¹³C NMR (CD₃OD, δ in ppm): 179.24, 174.88, 170.97, 170.43, 170.20, 161.29, 155.62, 149.30, 133.70, 130.23, 128.44, 123.54, 116.41, 114.72, 69.92, 68.15, 67.87, 54.96, 53.92, 49.27, 42.40, 39.62, 37.72, 36.91, 36.08, 35.29, 31.01, 29.51, 29.33, 24.08, 23.72, 21.93, 19.40, 19.34, 18.89, 17.24, 15.00, 9.34.

been formed. The reaction mixture was filtered and concentrated under reduced pressure, and the residue was dissolved in a solution of N,N-dimethylformamide (2 mL) and N,N-diisopropylethylamine (8 μL, 0.046 mmol). PFP ester intermediate (6.0 mg, 0.023 mmol) was added and the reaction mixture was stirred at room temperature for 2 h under argon. LCMS (10-100% ACN, 50 mM NH₄HCO₃ pH7) indicated all of the activated intermediate had been consumed and product had been formed. The reaction mixture was purified by preparative HPLC (10-100% ACN, 50 mM NH₄HCO₃ pH7) to yield 13b (4.7 mg, 37%). LCMS: [M+H]⁺ m/z=816.71. ¹H NMR (CDCl₃, δ in ppm): 8.04 (s, 1H) 7.05 (d, J=8.4 Hz, 2H) 6.80 (d, J=8.4 Hz, 2H) 5.90 (m, 1H) 5.38 (d, J=10.2 Hz, 1H) 4.63 (t, J=9.3 Hz, 1H) 4.38 (br, 1H) 4.27 (d, J=9.9 Hz, 1H) 3.48 (m, 1H) 3.34 (m, 2H) 2.86 (m, 6H) 2.56 (m, 3H) 2.23 (s, 3H) 2.16 (s, 3H) 1.22-2.10 (br, 16H) 1.12 (d, J=6.9 Hz, 3H) 1.03 (d, J=6.6 Hz, 3H) 0.88 (m, 14H). ¹³C NMR: 174.90, 170.44, 161.73, 155.52, 149.37, 130.77, 128.56, 124.33, 115.91, 70.40, 69.69, 67.62, 55.45, 53.70, 49.25, 44.61, 40.40, 36.94, 36.69, 35.93, 31.77, 31.16, 30.06, 24.94, 23.14, 21.08, 20.74, 20.20, 19.55, 17.78, 16.08, 14.05, 10.70

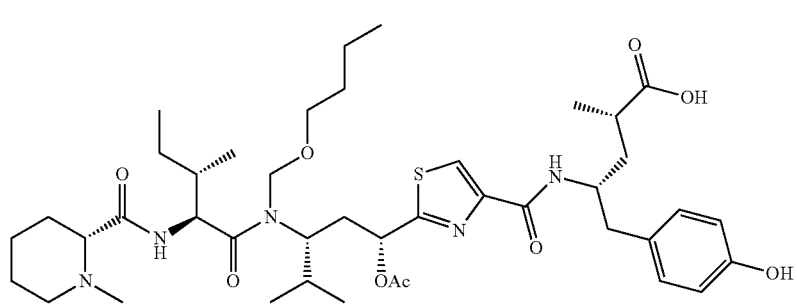

13b

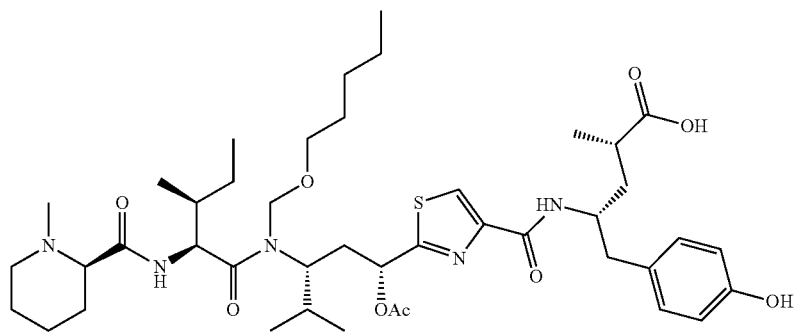

13c

In a 25 mL round bottom flask, 12c (4.8 mg, 0.008 mmol) and pentafluorophenol (14.1 mg, 0.077 mmol) were dissolved in dry dichloromethane (5 mL). N-cyclohexylcarbodiimide, N'-methyl polystyrene (16.7 mg, 2.3 mmol/g, 0.038 mmol) was added and the reaction mixture was stirred at room temperature for 16 h under Argon. LC-MS (10-100% ACN, 50 mM NH$_4$HCO$_3$ pH7) indicated all of the starting material had been consumed and activated intermediate had been formed. The reaction mixture was filtered and concentrated under reduced pressure, and the residue was dissolved in a solution of N,N-dimethylformamide (2 mL) and N, N-diisopropylethylamine (4 µL, 0.023 mmol). PFP ester intermediate (3.0 mg, 0.012 mmol) was added and the reaction mixture was stirred at room temperature for 2 h under Argon. LC-MS (10-100% ACN, 50 mM NH$_4$HCO$_3$ pH7) indicated all of the activated intermediate had been consumed and product had been formed. The reaction mixture was purified by preparative HPLC (10-100% ACN, 50 mM NH$_4$HCO$_3$ pH7) to yield 13c (1.1 mg, 17%). LCMS: [M+H]$^+$ m/z=830.76. $^1$H NMR (CDCl$_3$ w/2 drops CD$_3$OD): 8.00 (s, 1H) 7.01 (d, J=8.7 Hz, 2H) 6.74 (d, J=8.4 Hz, 2H) 5.89 (d, J=12.6 Hz, 1H) 5.25 (d, J=9.0 Hz, 1H) 4.55 (d, J=8.7 Hz, 1H) 4.30 (m, 3H) 3.39 (m, 3H) 3.21 (m, 2H) 2.81 (m, 3H) 2.04-2.60 (br, 45H) 1.76-2.04 (m, 5H) 1.34-1.76 (br, 9H) 1.20 (m, 6H) 1.12 (d, J=7.2 Hz, 4H) 1.01 (d, J=6.3 Hz, 3H) 0.89 (t, J=7.1 Hz, 6H) 0.78 (m, 6H)

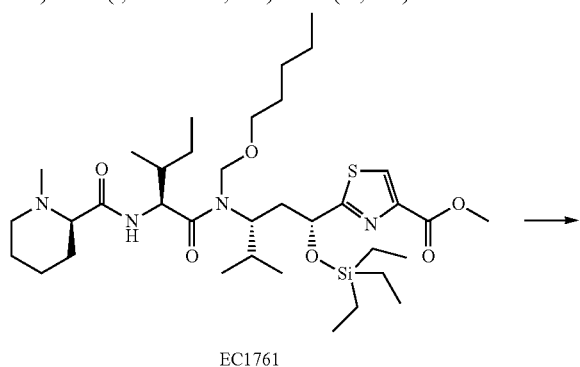

EC1761

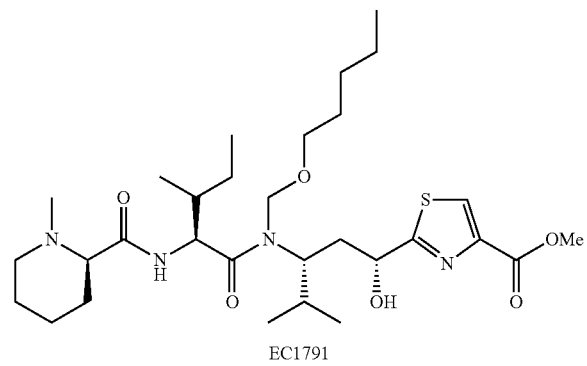

EC1791

Synthesis of EC1791. 100 mg of tripeptide methyl ester EC1761 (0.14 mmol) was dissolved in 1.5 mL of THF and 24 µL of 3HF-NEt$_3$ (0.15 mmol) was added. The mixture was stirred at room temperature for 2 hrs. The solvent was evaporated. The crude product was purified by SiO$_2$ column chromatography (Combiflash®) with DCM/MeOH gradient elution (0% to 10%) to give 80 mg of EC1791 (95%).

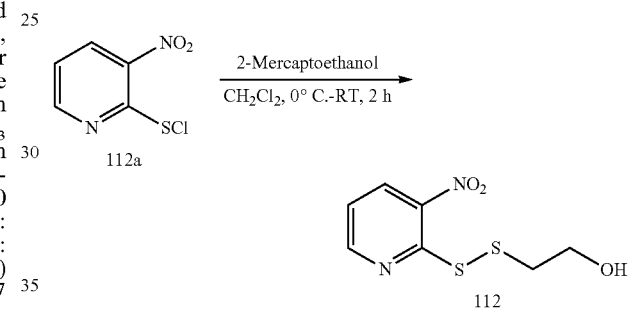

Example

Synthesis of 3-nitro-2-disulfenylethanol 112. A three-necked 500 mL flask was dried and argon purged, then fitted with an addition funnel. 3-Nitro-2-sulfenyl chloride pyridine 112a (5.44 g, 27.11 mmol, 1.4 equiv) was added to the flask and dissolved in 200 mL of CH$_2$Cl$_2$. The solution was cooled to 0° C. Mercaptoethanol (1.33 mL, 18.98 mmol) was diluted with 50 mL of CH$_2$Cl$_2$ and placed in the addition funnel. The 2-mercaptoethanol solution was then added drop-wise slowly over the course of 15 minutes. The reaction progress was monitored by TLC (Rf 0.4 in 5% CH$_3$OH/CH$_2$Cl$_2$). Solvent was removed under reduced pressure and dried. The crude product was purified over silica gel (5% CH$_3$OH/CH$_2$Cl$_2$). The fractions were collected and solvent was removed by evaporating on a rotary evaporator and dried. 3.4 g of 3-nitro-2-disulfenylethanol 112 was obtained (77% yield).

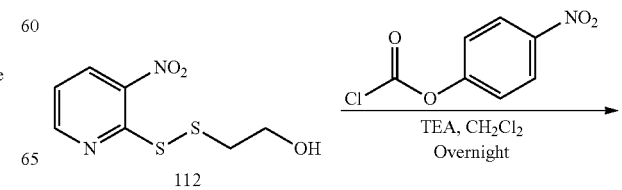

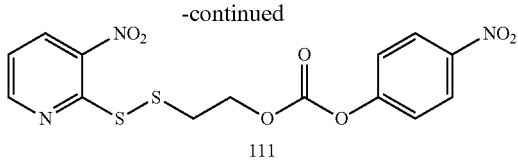

Example

Synthesis of 4-nitrophenyl-(3'-nitropyridin-2'-yl)disulfenylethyl carbonate 111. A 250 mL Round-Bottomed Flask was dried and argon purged. 3-Nitro-2-disulfenylethanol 112 (3.413 g, 14.69 mmol) was added and dissolved in 45 mL of CH$_2$Cl$_2$. 4-Nitrophenylchloroformate (3.663 g, 17.63 mmol, 1.2 equiv) was added, along with triethylamine (2.9 mL, 20.57 mmol, 1.4 equiv), and the mixture stirred under argon overnight. The mixture was concentrated under reduced pressure and dried. The residue was purified by silica (30% EtOAc/petroleum ether) and the fractions were collected, solvent was removed under reduced pressure, and dried. 2.7 g of 4-nitrophenyl-(3'-nitropyridin-2'-yl)disulfenylethyl carbonate 111 was obtained (47% yield).

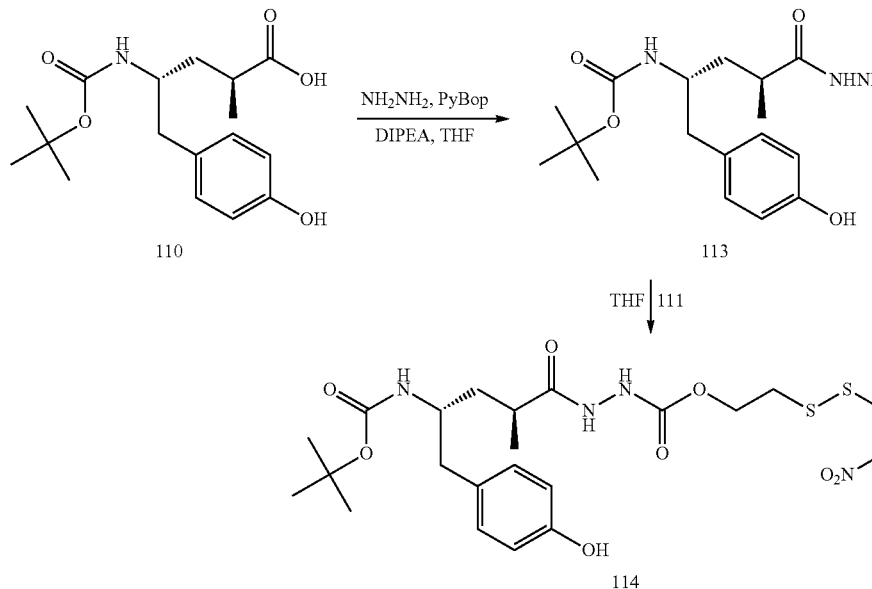

Example

Synthesis of 2-(Boc-tubutyrosine (Tut))hydrazinecarboxylic acid (3'nitropyridyl-2'-yl)disulfanylethyl ester 114. 10.67 g (33 mmol) of Boc-Tut-acid 110 was dissolved in 100 mL anhydrous THF, 17.24 g (33 mmol) of PyBop, and 17.50 mL (99 mmol, 3.0 equiv) of DIPEA were added. The reaction mixture stirred for few minutes, 1.0 mL (31.68 mmol, 0.96 equiv) of hydrazine was added and stirred for 15 minutes. LC-MS analysis (X-Bridge shield RP18, 3.5 μm column; gradient 10% to 100% acetonitrile in 6 min, pH 7.4 buffer) confirmed the hydrazide 113 formation. 14.47 g (36.3 mmol, 1.1 equiv) of 4-nitrophenyl-(3'-nitropyridin-2'-yl)disulfenylethyl carbonate 111 was added. The resulting clear solution was stirred at room temperature for 24 hours. LC-MS analysis (X-Bridge shield RP18, 3.5 μm column; gradient 30% to 100% acetonitrile in 9 min, pH 7.4 buffer) indicated >98% conversion. The reaction mixture was diluted with EtOAc (~1.0 L), washed with sat. NH$_4$Cl (400 mL), sat. NaHCO$_3$ solution (3×300 mL), and brine (300 mL). The organic layer was dried over Na$_2$SO$_4$ (100 g), and concentrated under reduced pressure. The crude product was loaded onto a Teledyne Redisep Gold Silica Column and eluted with MeOH/CH$_2$Cl$_2$ (330 g column; 0 to 10% gradient) using a CombiFlash chromatography system. The fractions were collected and solvent was removed under reduced pressure and dried. 16.10 g of 2-(Boc-Tut)hydrazinecarboxylic acid (3'nitropyridyl-2'-yl)disulfanylethyl ester 114 was obtained (82% yield).

General Procedures:

Scheme 2

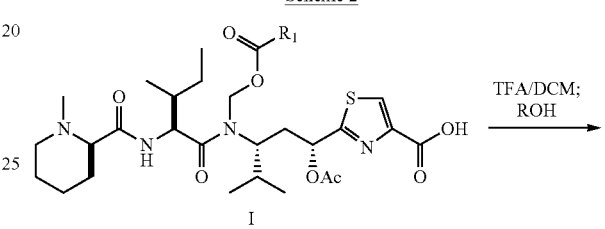

TFA/DCM; ROH

-continued

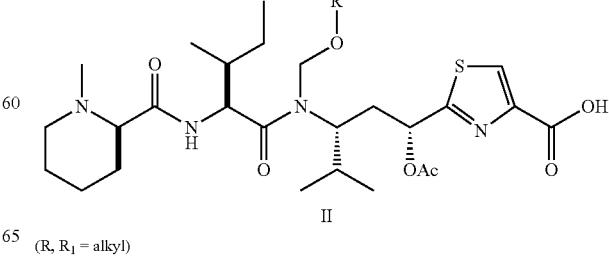

(R, R$_1$ = alkyl)

Synthesis of EC1623 (Scheme 2). EC1008 (I: $R_1$=n-propyl. 103 mg) was dissolved in anhydrous dichloromethane (DCM, 2.0 mL) and to this solution was added trifluoroacetic acid (TFA, 0.50 mL). The resulting solution was stirred at ambient temperature under argon for 20 minutes, and to which was added 1-pentanol (0.72 mL). The reaction mixture was stirred at ambient temperature for 3 minutes, concentrated on a Buchi Rotavapor at 30° C. for 10 minutes, residue stirred at ambient temperature under high vacuum for 75 minutes, and to which was added saturated $NaHCO_3$ solution (10 mL) with vigorous stirring, followed by addition of acetonitrile (ACN, 3.0 mL). The resulting white suspension was stirred at ambient temperature for 3 minutes and let stand to settle. The top clear solution was loaded onto a Biotage SNAP 12 g KP-C18-HS column on a Biotage system. The white solid left in the reaction flask was dissolved in water (5.0 mL) and the solution was also loaded onto the Biotage column. The remaining solid stuck on the glass wall of the reaction flask was dissolved in ACN (2.0 mL). To this solution was added water (6.0 mL) and the resulting cloudy solution was loaded onto the same Biotage column. The reaction mixture was eluted following these parameters: Flow rate: 15 mL/min. A: water; B: CAN. Method: 25% B 2 CV (column volume), 25-50% B 3 CV, and 50% B 5 CV (1 CV=15 mL). Fractions containing the desired product was collected and freeze-dried to afford EC1623 (II: R=n-pentyl. 95.9 mg) as a white powder.

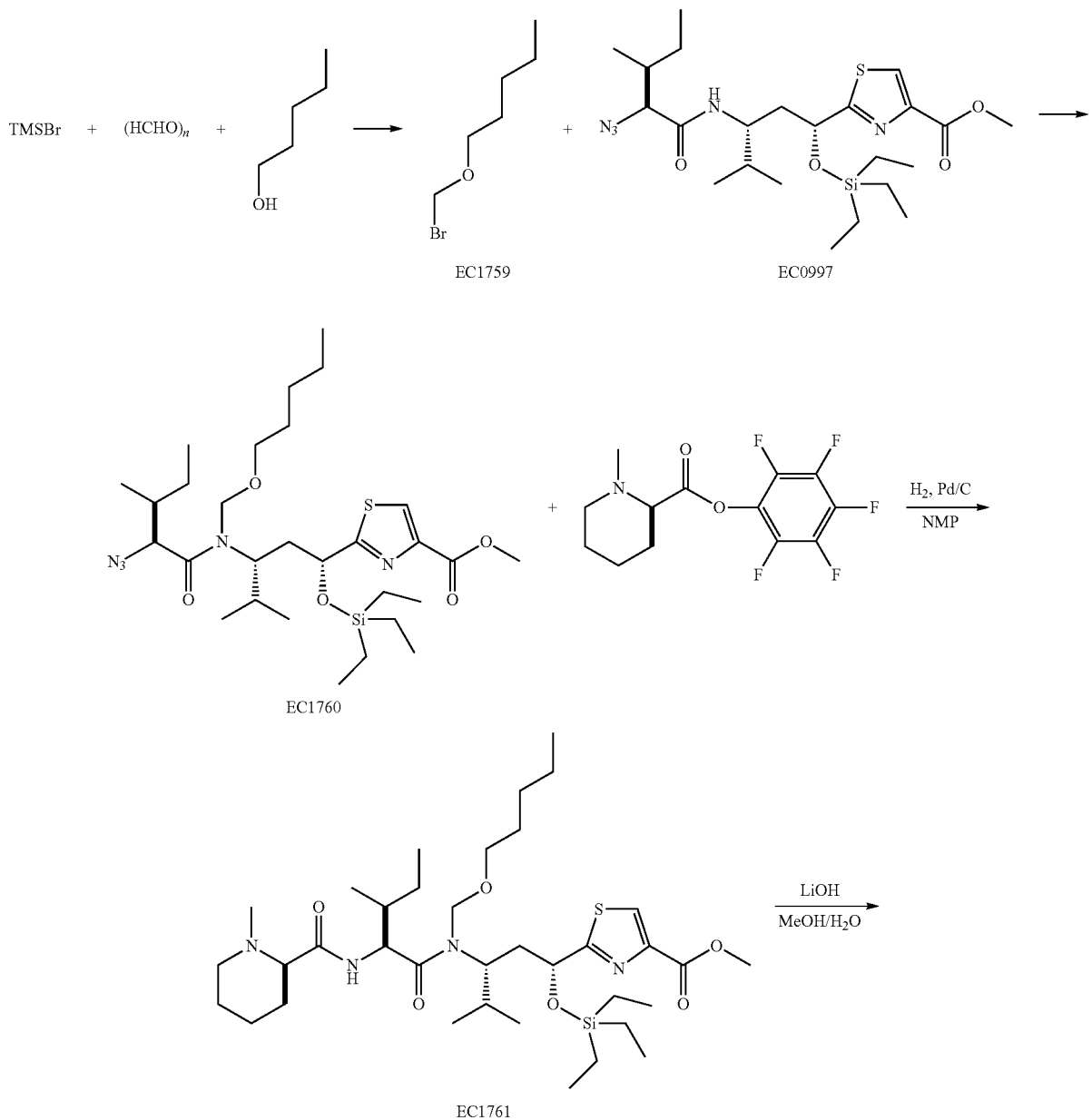

-continued
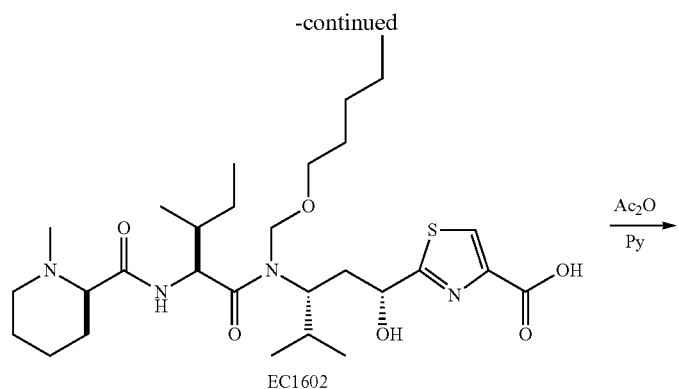
EC1602
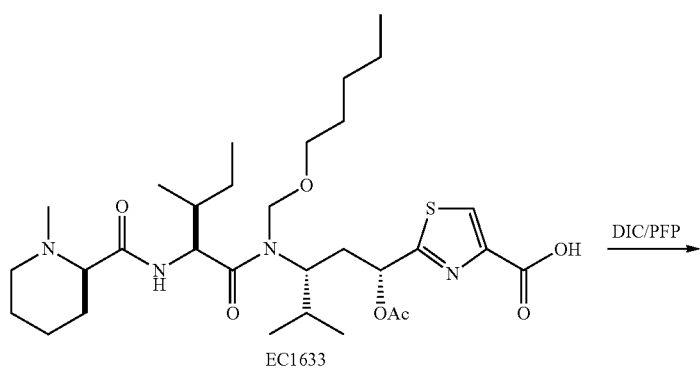
EC1633
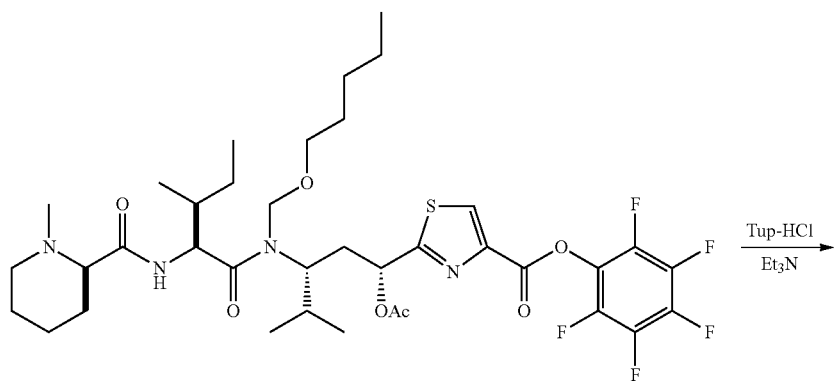
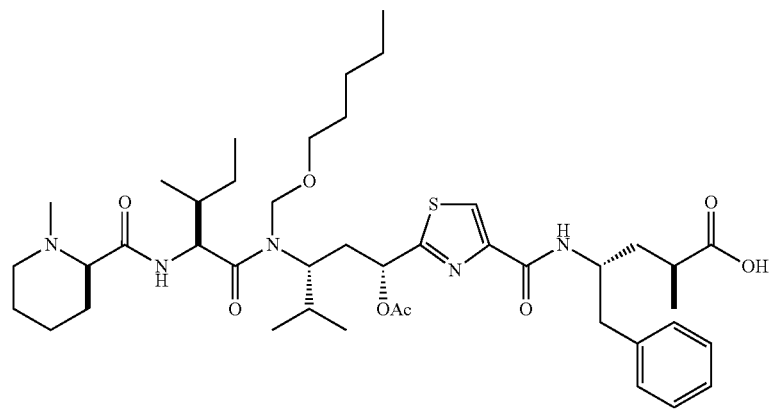
EC1988

Synthesis of EC 1988. 10 mg of EC1633 (0.017 mmol) was dissolved in 0.4 mL of DCM and 73 mg of DCC on resin (10 equiv.) and 6.5 mg of pentafluorophenol (2 equiv.) were added. The reaction was stirred overnight at room temperature. The resin was filtered off and rinsed with DCM. The filtrate was concentrated under reduced pressure. To the resulting residue was added a solution of 4.2 mg of Tup-HCl (0.017 mmol) and 45 μL of Et$_3$N (18 equiv.) in 0.4 mL of DMF. After 5 minutes, HPLC purification (ACN/50 mM NH$_4$HCO$_3$ (pH 7) mobile phase) gave 5 mg (37%) of EC 1988.

LCMS: [M+H]$^+$ m/z=814.52. $^1$H NMR (CD$_3$OD): 8.07 (s, 1H) 7.22 (m, 4H) 7.16 (m, 1H), 5.96 (d, 1H), 5.36 (d, 1H), 4.66 (d, 1H) 4.42 (d, 1H), 4.35 (m, 1H) 3.50 (m, 1H), 3.42 (m, 1H), 3.00 (d, br, 1H), 2.91 (d, 2H), 2.75 (d, br, 1H), 2.50 (m, 2H), 2.25 (s, 3H), 2.21 (m, 1H), 2.11 (s, 3H), 2.00 (m, 2H), 1.79 (m, 3H), 1.45-1.75 (m, 7H), 1.20-1.40 (m, 6H), 1.15 (d, 3H), 1.05 (d, 3H), 0.94 (d, 3H), 0.91 (t, 3H), 0.82 (t, 3H), 0.76 (d, 3H).

$^{13}$C NMR (CD$_3$OD): 180, 174.9, 172.9, 170.5, 169.5, 161.3, 149.3, 138.1, 129.2, 127.9, 125.9, 123.8, 69.5, 68.6, 67.0, 55.1, 53.6, 49.5, 42.9, 40.4, 38.0, 37.6, 36.1, 34.6, 31.0, 29.9, 29.0, 28.2, 24.4, 24.1, 22.5, 22.0, 19.39, 19.34, 18.8, 17.4, 15.0, 12.9, 9.3.

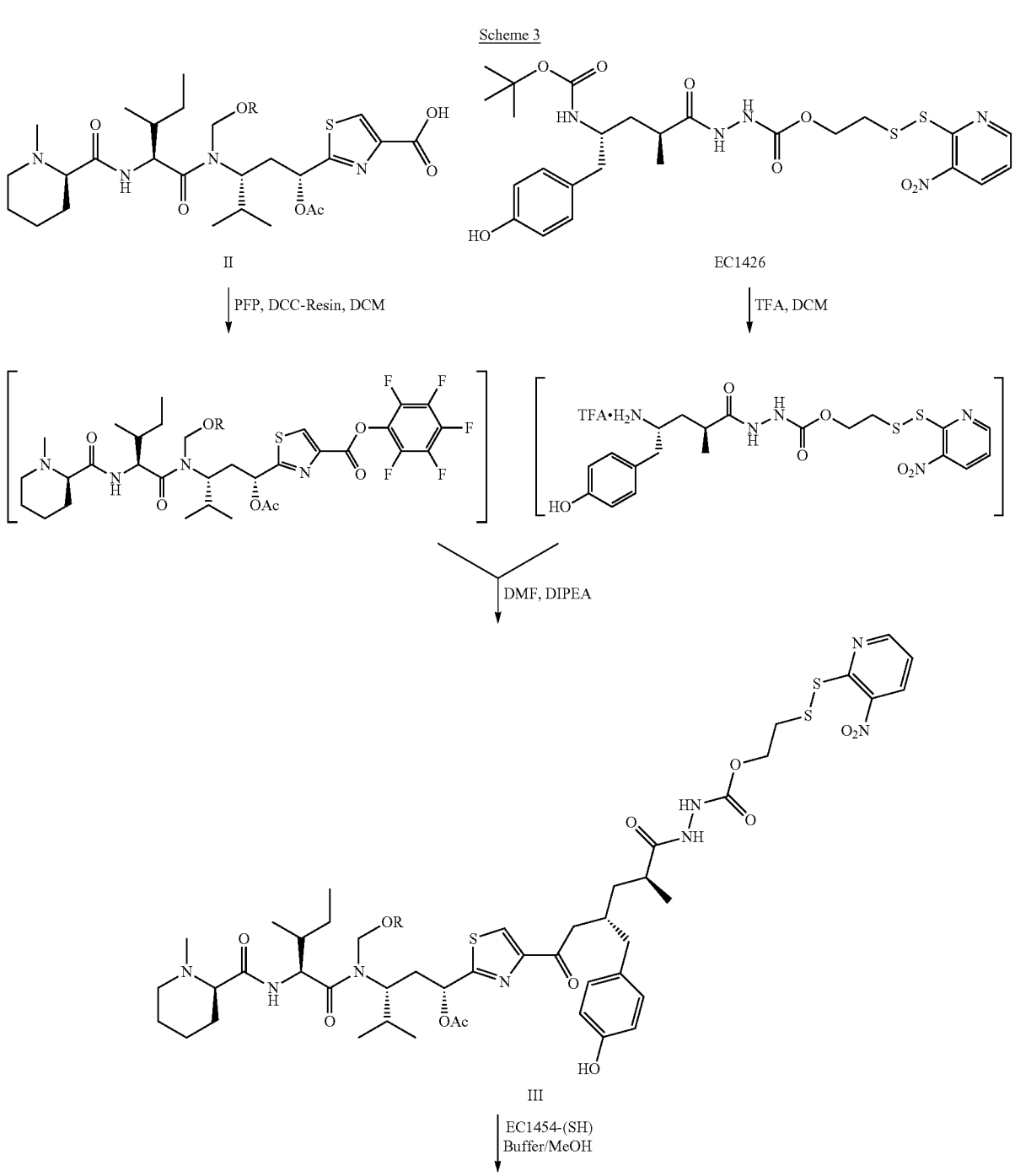

Scheme 3

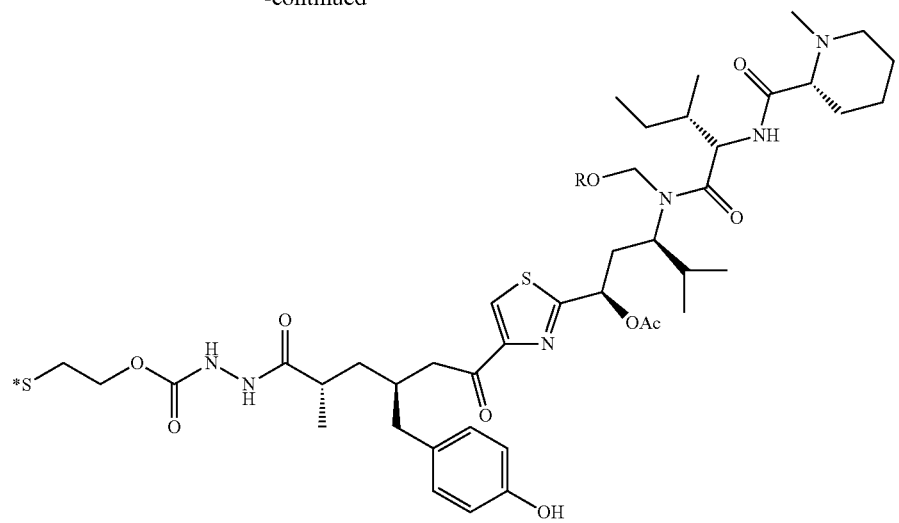

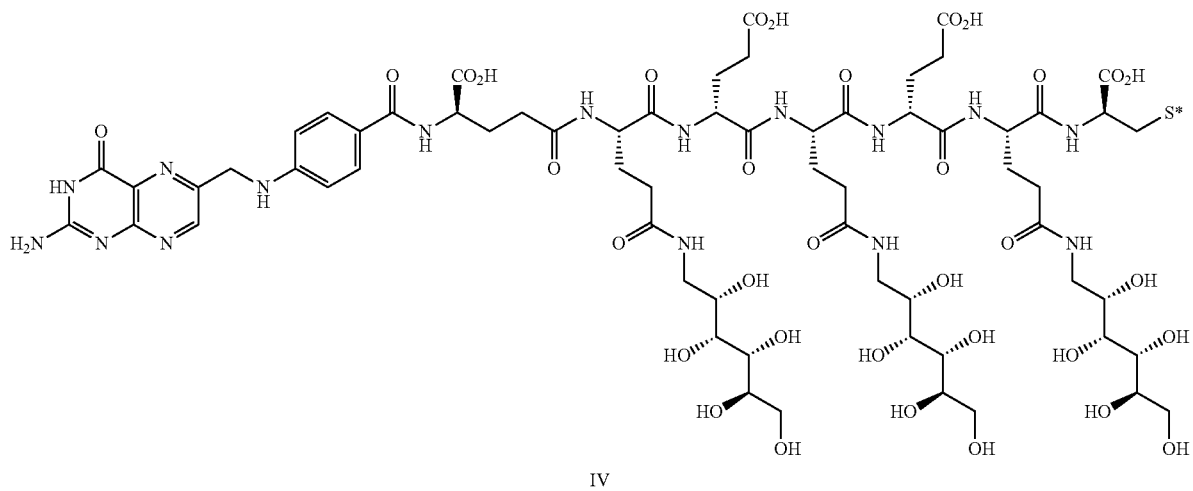

IV (R = alkyl)

Synthesis of EC1662 (Scheme 3).

Step 1: Anhydrous DCM (5.0 mL) was added to a mixture of EC1623 (II: R=n-pentyl. 114 mg), pentafluorophenol (PFP, 67.3 mg), and DCC-resin (2.3 mmol/g, 396 mg) and the suspension was stirred at ambient temperature under argon for 23 hours. The resin was filtered off and washed with anhydrous DCM (3.0 mL) and the combined filtrates were concentrated under reduced pressure to give a residue, which was vacuumed at ambient temperature for 1 hour prior to use in Step 3.

Step 2: EC1426 (114 mg) was dissolved in anhydrous DCM (1.5 mL) and to which was added TFA (0.50 mL). The resulting solution was stirred at ambient temperature under argon for 70 minutes and concentrated under reduced pressure to give a residue, which was co-evaporated with anhydrous DCM (2.0 mL×3) and vacuumed at ambient temperature for 9 hours prior to use in Step 3.

Step 3: The residue from Step 1 was dissolved in anhydrous DCM (1.5 mL) and to this solution was added DIPEA (0.50 mL) followed by a solution of the residue from Step 2 dissolved in anhydrous dimethylformamide (DMF, 1.5 mL). The resulting solution was stirred at ambient temperature under argon for 1 hour, diluted with ethyl acetate (EtOAc, 60 mL), and washed with brine (20 mL×3). The organic layer was separated, dried ($Na_2SO_4$), and concentrated under reduced pressure to give a residue, which was vacuumed at ambient temperature for 2 hours, dissolved in DCM (3.5 mL), and loaded onto a 24 g silica gel column on a CombiFlash system for purification. The materials were eluted with 0-5% MeOH in DCM to afford EC1662 (III: R=n-pentyl. 171 mg) as a white solid.

Synthesis of EC1664 (Scheme 3).

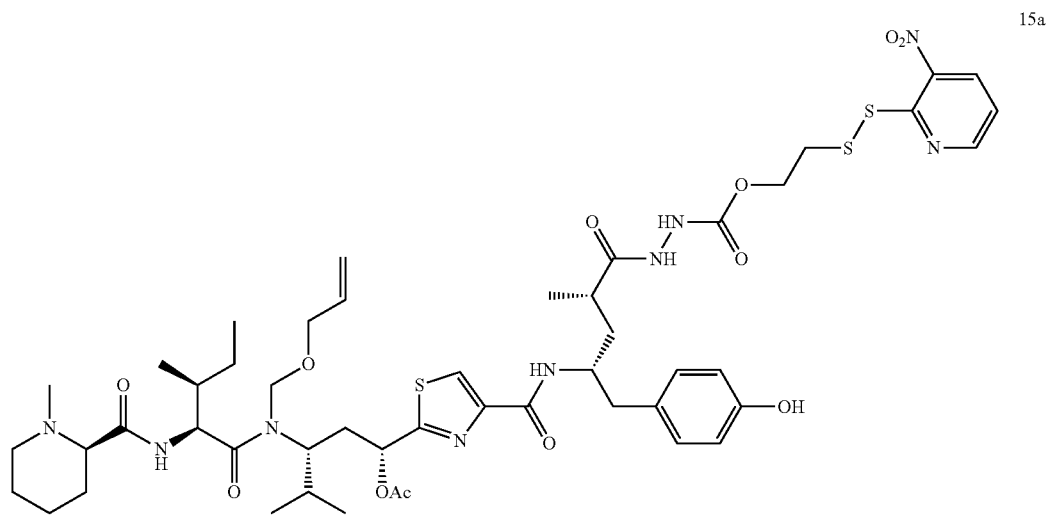 [SMILES: C=CCOCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(O)cc2)C[C@H](C)C(=O)NNC(=O)OCCSSc2ncccc2[N+](=O)[O-])cs1)C(C)C]

Compound 12a (26.4 mg, 0.044 mmol) was dissolved in anhydrous methylene chloride (5 mL) and to this solution was added DCC-resin (2.3 mmol/g, 0.096 g, 0.22 mmol), followed by pentafluorophenol (PFP, 16.4 mg, 0.089 mmol) at rt under argon. The reaction was stirred for 19 hrs at rt. The reaction was filtered and concentrated and the residue was redissolved in dry DMF (5 mL). 2-((3-nitropyridin-2-yl)disulfanyl)ethyl 2-((2S,4R)-4-((tert-butoxycarbonyl)amino)-5-(4-hydroxyphenyl)-2-methylpentanoyl)hydrazinecarboxylate (40.0 mg, 0.067 mmol) was deprotected with TFA/DCM (1:1, 5 mL, 1 drop of TIPS as scavenger) at rt for 1 hr. The solvent was removed under reduced pressure, 5 mL more of DCM was added, and then the solvent was co-evaporated to dryness. The residue was dissolved in dry DMF (2 mL) and was added to the solution of PFP ester intermediate in DMF made above after the addition of DIPEA (23.2 μL, 0.13 mmol) at rt under argon. The reaction was stirred for 19 hrs and diluted with EtOAc (20 mL). The organic phase was washed with water (5 mL×3) and brine. The organic layer was dried over anhydrous $Na_2SO_4$ and concentrated after filtration to give the crude product 15a (52.8 mg), which could be used for conjugation with folate. LCMS: $[M+H]^+$ m/z=1072.92.

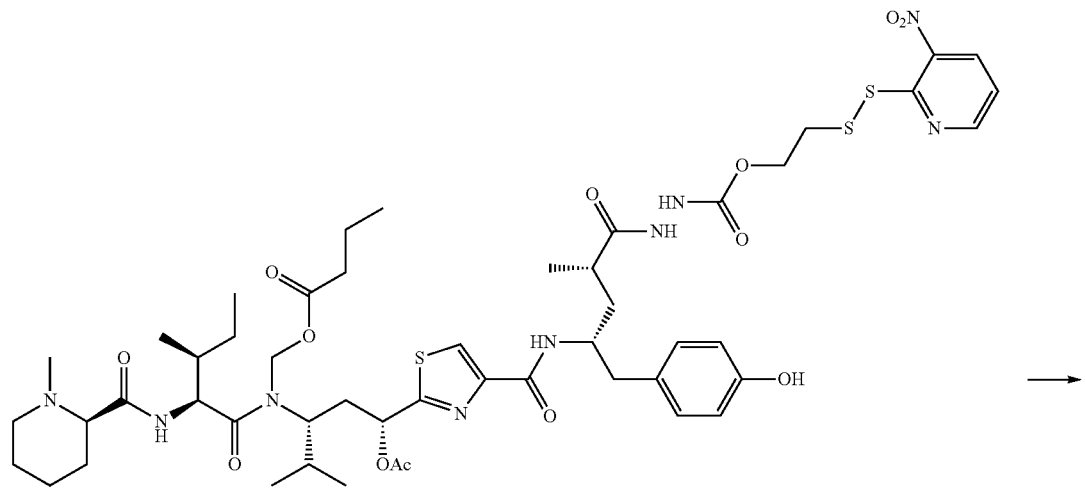

-continued

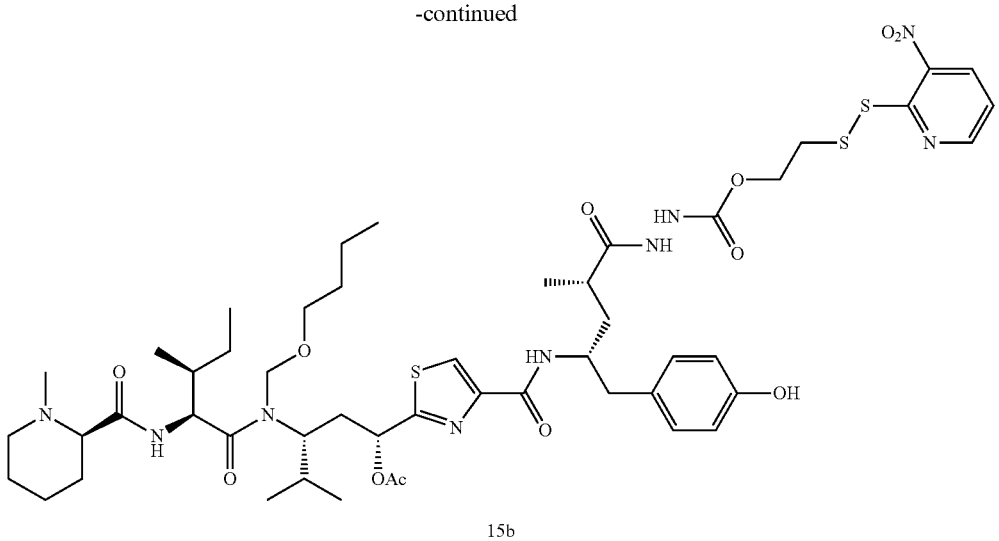

15b

In a 5 mL round bottom flask, 14 (10.0 mg, 0.009 mmol) was dissolved in a solution of trifluoroacetic acid (125 μL, 1.632 mmol) and dichloromethane (0.5 mL) and stirred at room temperature for 1 hr under argon, then 1-butanol (200 μL, 2.186 mmol) added and reaction mixture stirred at room temperature for 30 min under argon. LCMS (10-100% ACN, 50 mM NH$_4$HCO$_3$ pH7) indicated all of the starting material had been consumed and product had been formed. The reaction mixture was purified by preparative HPLC (10-100% ACN, 50 mM NH$_4$HCO$_3$ pH7) to yield 15b (3.2 mg, 32%). LCMS: [M+H]$^+$ m/z=1088.79. $^1$H NMR (CDCl$_3$ w/2 drops CD$_3$OD): 8.86 (s, 1H) 8.47 (d, J=8.0 Hz, 1H) 7.99 (s, 1H) 7.31 (d, J=9.5 Hz, 2H) 7.01 (d, J=7.5 Hz, 2H) 6.73 (d, J=8.5 Hz, 2H) 5.94 (d, J=10.5 Hz, 1H) 5.34 (d, J=10.0 Hz, 1H) 4.58 (m, 3H) 4.38 (t, J=6.0 Hz, 4H), 4.27 (d, J=10.0 Hz, 2H) 3.37 (m, 2H) 3.18 (m, 2H) 3.09 (t, J=6.3 Hz, 3H) 2.70-2.90 (br, 6H) 2.43 (dd, J=11.0 Hz, 3.0 Hz, 2H) 2.26-2.36 (br, 4H) 2.12-2.22 (br, 10H) 2.02-2.12 (br, 2H) 1.86-2.02 (br, 11H) 1.69-1.80 (br, 6H) 1.54-1.69 (br, 10H) 1.34-1.52 (br, 12H) 1.09-1.34 (br, 16H) 1.047 (dd, J=15.0 Hz, 6.5 Hz, 19H) 0.88 (m, 19H) 0.75 (m, 17H). $^{13}$C NMR: 174.95, 174.59, 170.64, 170.23, 161.92, 156.91, 156.06, 153.88, 149.00, 133.77, 130.79, 123.92, 120.98, 115.53, 69.95, 69.61, 67.03, 63.82, 55.32, 53.21, 44.78, 41.42, 40.40, 36.84, 36.38, 35.62, 35.22, 31.54, 31.40, 30.37, 24.99, 24.66, 23.20, 20.68, 20.24, 19.56, 19.27, 17.69, 15.71, 13.72, 10.35

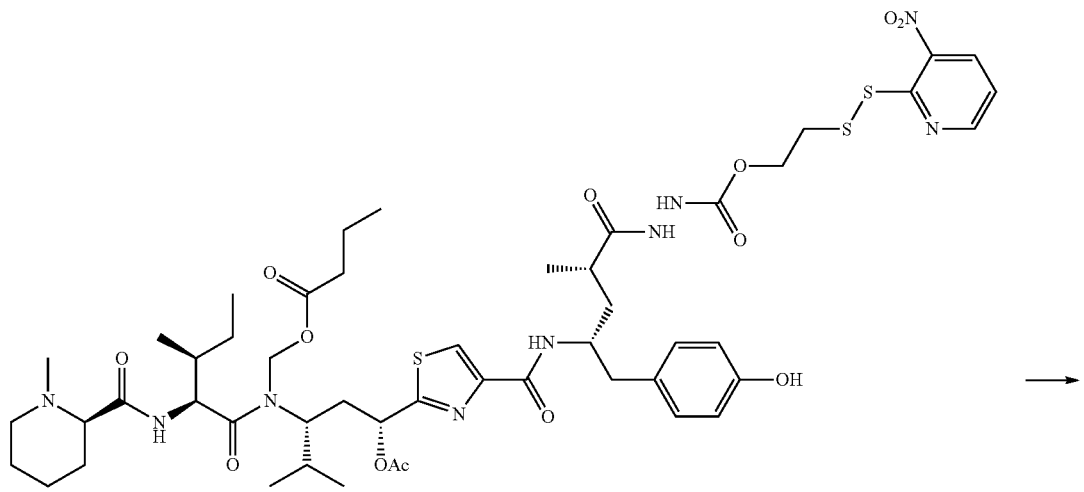

14

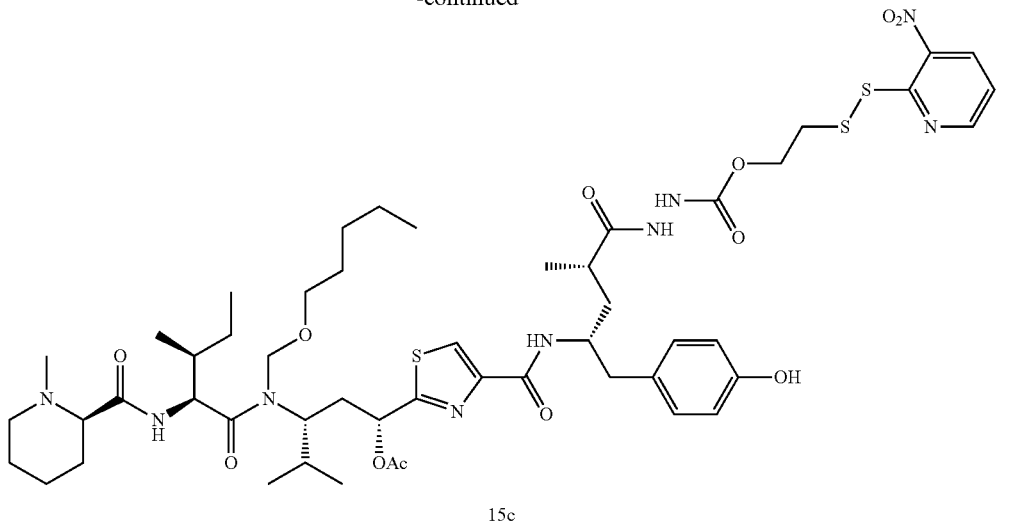

15c

In a 5 mL round bottom flask, 14 (10.0 mg, 0.009 mmol) was dissolved in a solution of trifluoroacetic acid (125 μL, 1.632 mmol) and dichloromethane (0.5 mL) and stirred at room temperature for 1 hr under argon, then 1-pentanol (200 μL, 1.840 mmol) added and reaction mixture stirred at room temperature for 30 min under argon. LC-MS (10-100% ACN, 50 mM NH$_4$HCO$_3$ pH7) indicated all of the starting material had been consumed and product had been formed. The reaction mixture was purified by preparative HPLC (10-100% ACN, 50 mM NH$_4$HCO$_3$ pH7) to yield 15c (3.6 mg, 36%). LCMS: [M+H]$^+$ m/z=1102.77.

Example

General Synthesis of Disulfide Containing Tubulysin Conjugates. A binding ligand-linker intermediate containing a thiol group is taken in deionized water (ca. 20 mg/mL, bubbled with argon for 10 minutes prior to use) and the pH of the suspension was adjusted with aqueous phosphate (bubbled with argon for 10 minutes prior to use) to a pH of about 7.0 (the suspension may become a solution when the pH increased). Additional deionized water is added (ca. 20-25%) to the solution as needed, and to the aqueous solution is added immediately a solution of compound (2) in acetonitrile (ca. 20 mg/mL). The reaction mixture becomes homogenous quickly. After stirring under argon, e.g. for 45 minutes, the reaction mixture is diluted with 2.0 mM sodium phosphate buffer (pH 7.0, ca 150 volume percent) and the acetonitrile is removed under vacuum. The resulting suspension is filtered and the filtrate may be purified by preparative HPLC. Fractions are lyophilized to isolate the conjugates. The foregoing method is equally applicable for preparing other tubulysin conjugates by the appropriate selection of the tubulysin starting compound, including tubulysin starting compounds having a 3-nitropyridin-2-ylthio activating group.

Illustrative binding ligand-linker intermediates are described in WO 2008/112873, the disclosure of which is incorporated herein by reference.

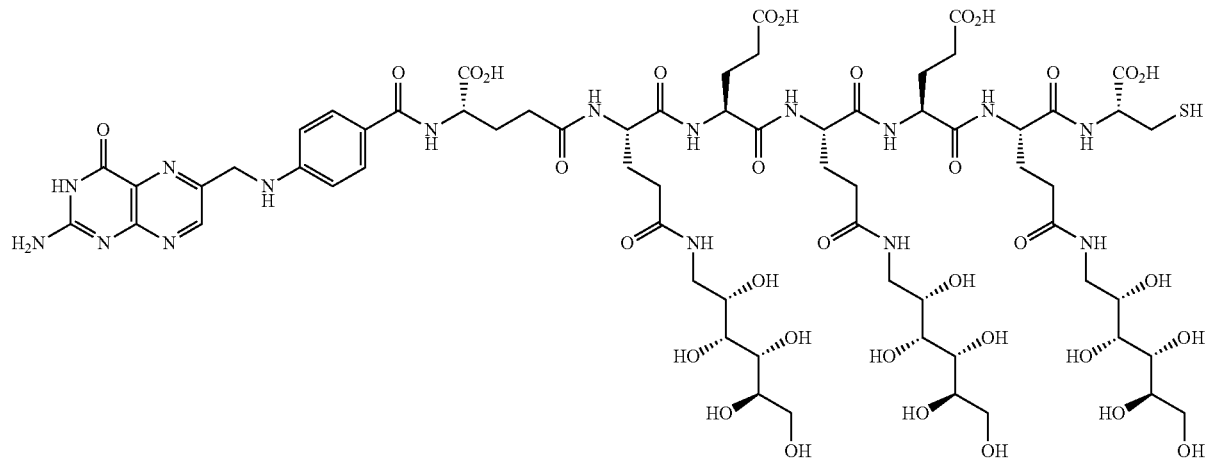 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O)C(=O)O)cc3)nc2c(=O)[nH]1]

EC0488. This binding ligand-linker intermediate was prepared by SPPS according to the general peptide synthesis procedure described herein starting from H-Cys(4-methoxytrityl)-2-chlorotrityl-Resin, and the following SPPS reagents:

| Reagents | mmol | equivalent | MW | amount |
|---|---|---|---|---|
| H-Cys(4-methoxytrityl)-2-chlorotrityl-Resin (loading 0.6 mmol/g) | 0.10 | | | 0.17 g |
| EC0475 | 0.13 | 1.3 | 612.67 | 0.082 g |
| Fmoc-Glu(OtBu)-OH | 0.19 | 1.9 | 425.47 | 0.080 g |
| EC0475 | 0.13 | 1.3 | 612.67 | 0.082 g |
| Fmoc-Glu(OtBu)-OH | 0.19 | 1.9 | 425.47 | 0.080 g |
| EC0475 | 0.13 | 1.3 | 612.67 | 0.082 g |
| Fmoc-Glu-OtBu | 0.19 | 1.9 | 425.47 | 0.080 g |
| $N^{10}$TFA-Pteroic Acid (dissolve in 10 ml DMSO) | 0.16 | 1.6 | 408.29 | 0.066 g |
| DIPEA | | 2.0 eq of AA | | |
| PyBOP | | 1.0 eq of AA | | |

Coupling steps. In a peptide synthesis vessel add the resin, add the amino acid solution, DIPEA, and PyBOP. Bubble argon for 1 hr. and wash 3× with DMF and IPA. Use 20% piperidine in DMF for Fmoc deprotection, 3× (10 min), before each amino acid coupling. Continue to complete all 9 coupling steps. At the end treat the resin with 2% hydrazine in DMF 3× (5 min) to cleave TFA protecting group on Pteroic acid, wash the resin with DMF (3×), IPA (3×), MeOH (3×), and bubble the resin with argon for 30 min.

Cleavage step. Reagent: 92.5% TFA, 2.5% $H_2O$, 2.5% triisopropylsilane, 2.5% ethanedithiol. Treat the resin with cleavage reagent 3× (10 min, 5 min, 5 min) with argon bubbling, drain, wash the resin once with cleavage reagent, and combine the solution. Rotavap until 5 ml remains and precipitate in diethyl ether (35 mL). Centrifuge, wash with diethyl ether, and dry. About half of the crude solid (~100 mg) was purified by HPLC.

HPLC Purification step. Column: Waters Xterra Prep MS C18 10 μm 19×250 mm; Solvent A: 10 mM ammonium acetate, pH 5; Solvent B: ACN; Method: 5 min 0% B to 25 min 20% B 26 mL/min. Fractions containing the product was collected and freeze-dried to give 43 mg EC0488 (51% yield). $^1$H NMR and LC/MS (exact mass 1678.62) were consistent with the product.

A solution of EC1454 (44.1 mg.) in 20 mM phosphate buffer (pH 7.0, 4.0 mL) was added to a solution of EC1662 (24.1 mg) in MeOH (4.8 mL), followed by addition of saturated $Na_2SO_4$ (0.30 mL). The reaction mixture was stirred at ambient temperature under argon for 30 minutes and the solution was injected onto a preparative HPLC (A: 50 M $NH_4HCO_3$ buffer, pH 7.0; B: CAN. Method: 10-80% B in 20 minutes.) for purification. Fractions containing the desired product were collected and freeze-dried to afford EC1664 (IV: R=n-pentyl, disulfide formed by (S*) atoms, 42.8 mg) as a fluffy yellow solid.

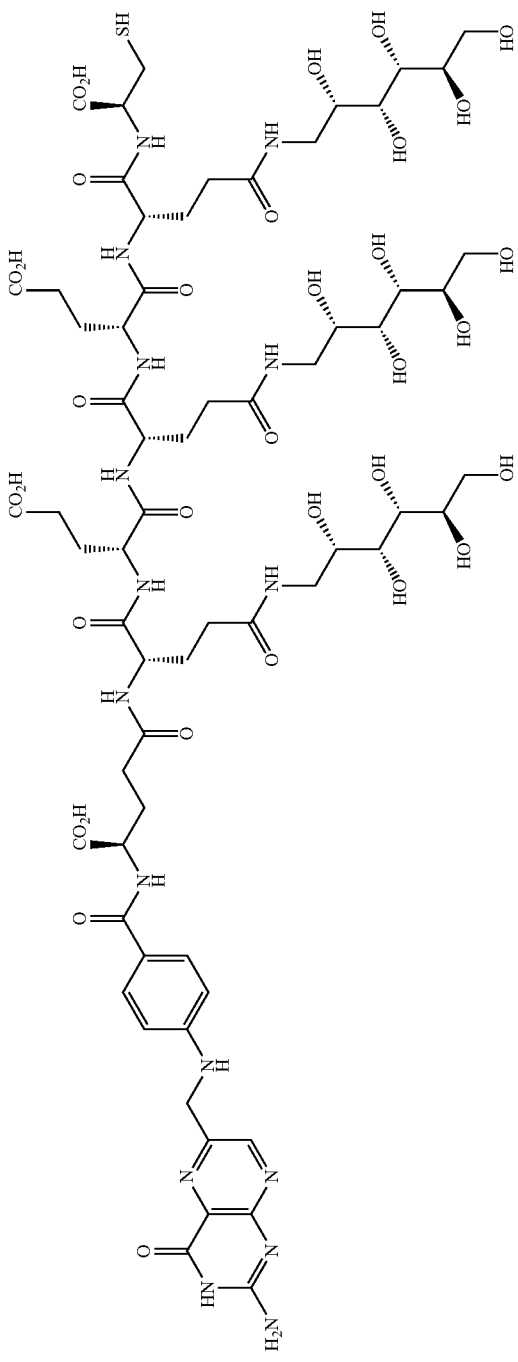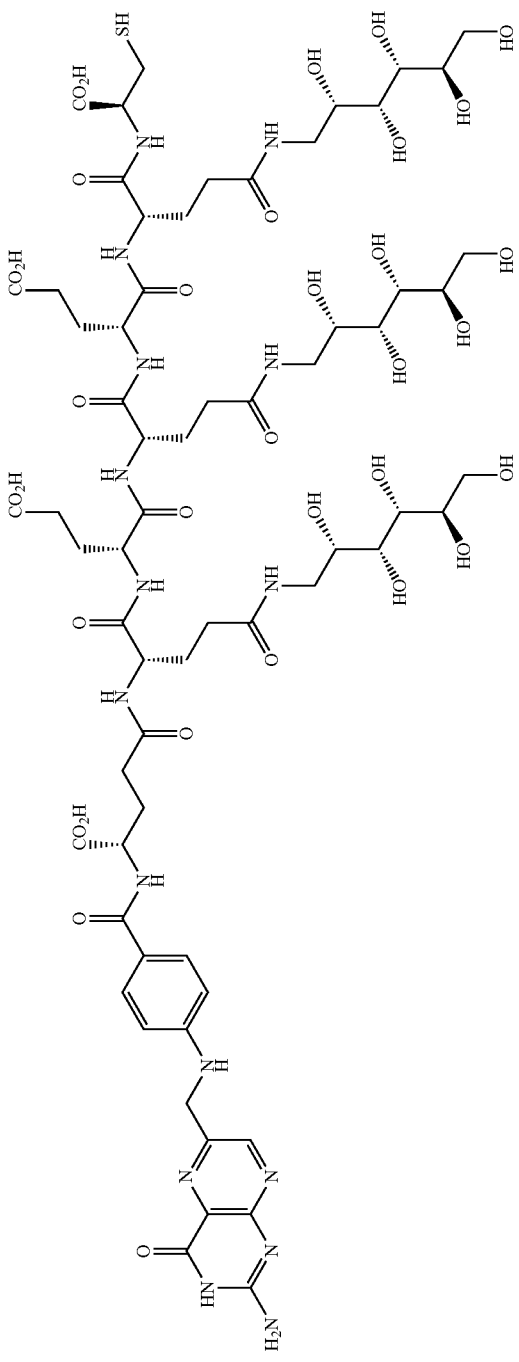

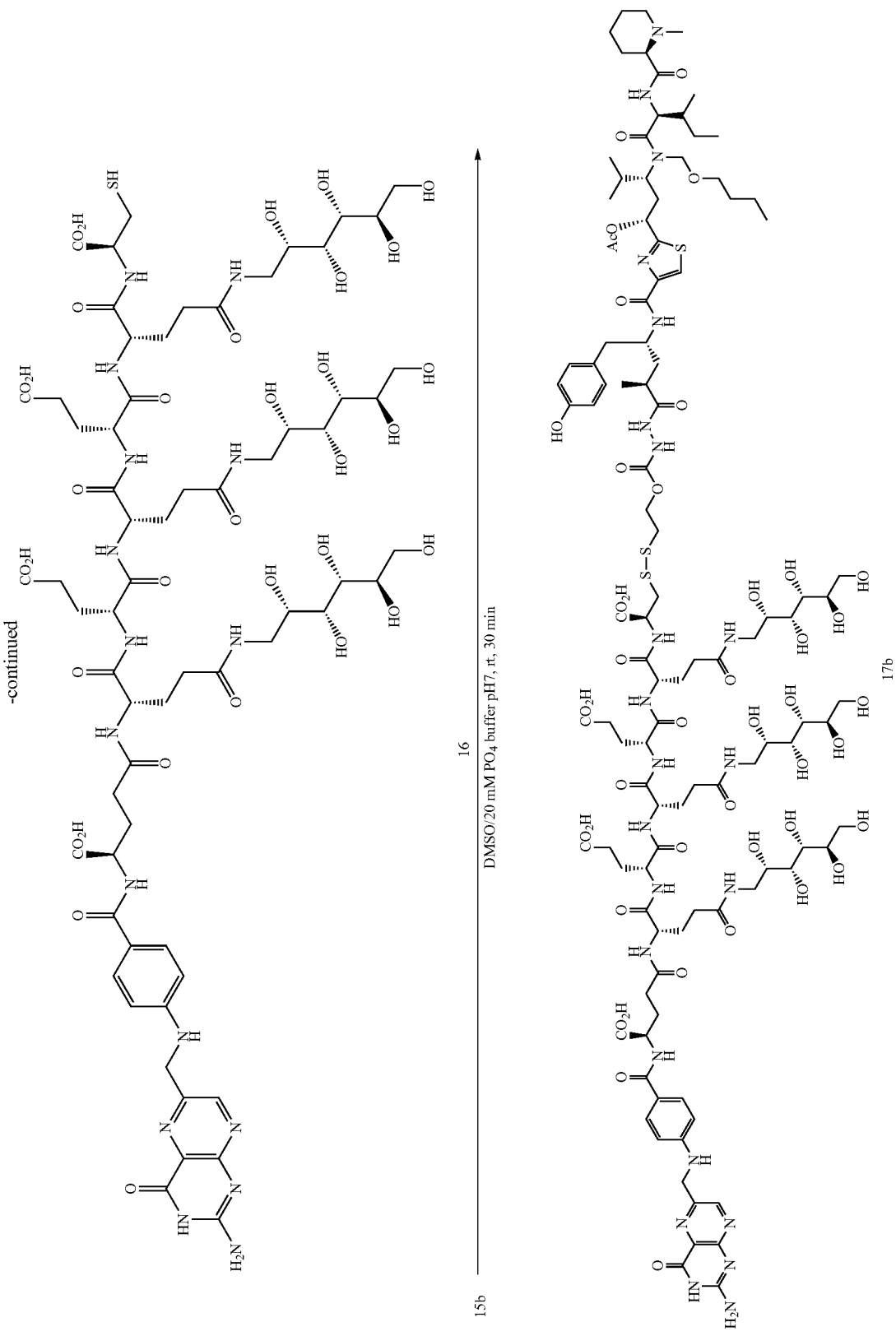

In a 25 mL round bottom flask, 15b (3.2 mg, 0.003 mmol) was dissolved in dimethylsulfoxide (2 mL). A solution of 16 (4.9 mg, 0.003 mmol) in 20 mM, pH7, sodium phosphate buffer (2 mL) was added dropwise, stirring at room temperature with argon bubbling for 30 min. LCMS (10-100% ACN, 50 mM $NH_4HCO_3$ pH7) indicated all of the starting material had been consumed and product had been formed. The reaction mixture was purified by preparative HPLC (10-100% ACN, 50 mM $NH_4HCO_3$ pH7) to yield 17b (4.3 mg, 56%). LCMS: $[M+H]^+$ m/z=1306.82. $^1H$ NMR (9:1 DMSO-d6:$D_2O$): 8.60 (s, 1H) 8.14 (s, 1H) 7.59 (d, J=8.5 Hz, 2H) 6.94 (d, J=7.5 Hz, 2H) 6.60 (dd, J=13.3 Hz, 8.8 Hz, 3H) 5.77 (d, J=11.5 Hz, 1H) 5.20 (d, J=9.5 Hz, 1H) 4.46 (m, 3H) 4.00-4.40 (br, 12H) 3.48-3.62 (br, 11H) 3.28-3.48 (br, 12H) 3.10-3.28 (br, 4H) 2.80-3.08 (br, 7H) 2.60-3.80 (br, 3H) 2.48 (s, 1H) 2.26-2.40 (br, 2H) 2.00-2.26 (br, 19H) 1.58-2.00 (br, 20H) 1.28-1.58 (br, 8H) 1.18 (q, J=7.5 Hz, 3H) 0.84-1.10 (br, 8H) 0.75 (m, 9H) 0.60 (d, J=6.5 Hz, 3H). $^{13}C$ NMR: 175.25, 174.93, 174.36, 173.59, 173.22, 172.76, 172.70, 172.02, 171.85, 171.67, 170.85, 170.34, 169.68, 166.48, 161.94, 160.67, 156.42, 155.80, 154.22, 150.98, 149.56, 149.21, 149.08, 130.64, 129.17, 128.69, 128.08, 124.89, 122.00, 115.31, 111.84, 72.31, 72.23, 71.82, 71.69, 69.84, 69.74, 68.21, 66.59, 63.52, 63.09, 55.04, 53.74, 53.56, 53.23, 52.96, 52.48, 46.11, 43.63, 42.39, 37.43, 35.69, 35.41, 35.19, 32.17, Synthesis of EC1997

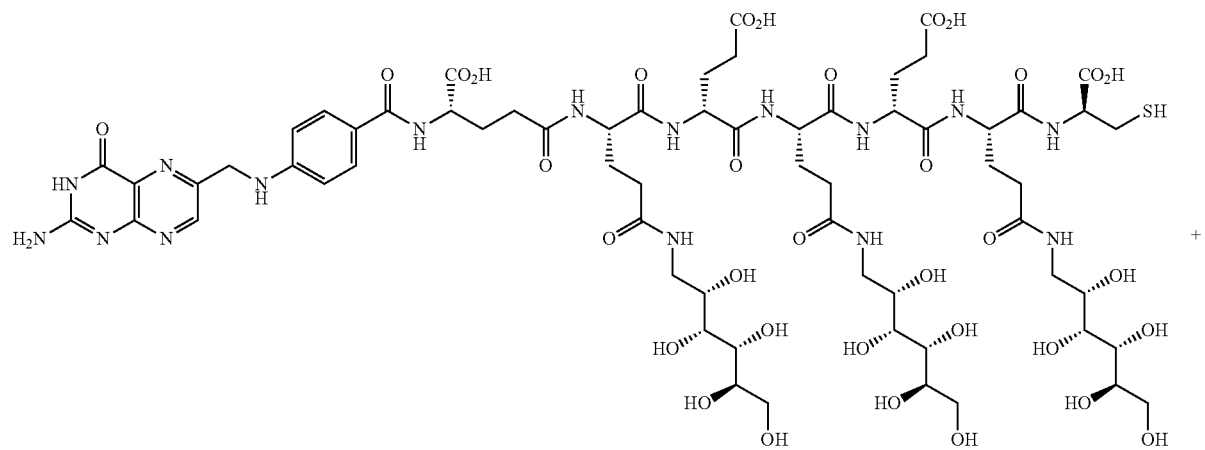

EC1579
$C_{65}H_{98}N_{16}O_{34}S$
Exact Mass: 1678.62
Molecular Weight: 1679.63

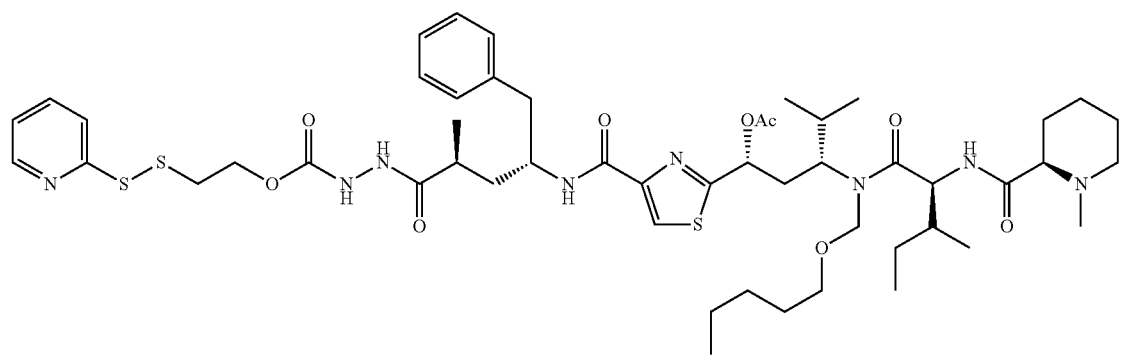

EC1996
Chemical Formula: $C_{51}H_{76}N_8O_9S_3$
Exact Mass: 1040.49
Molecular Weight: 1041.39

-continued

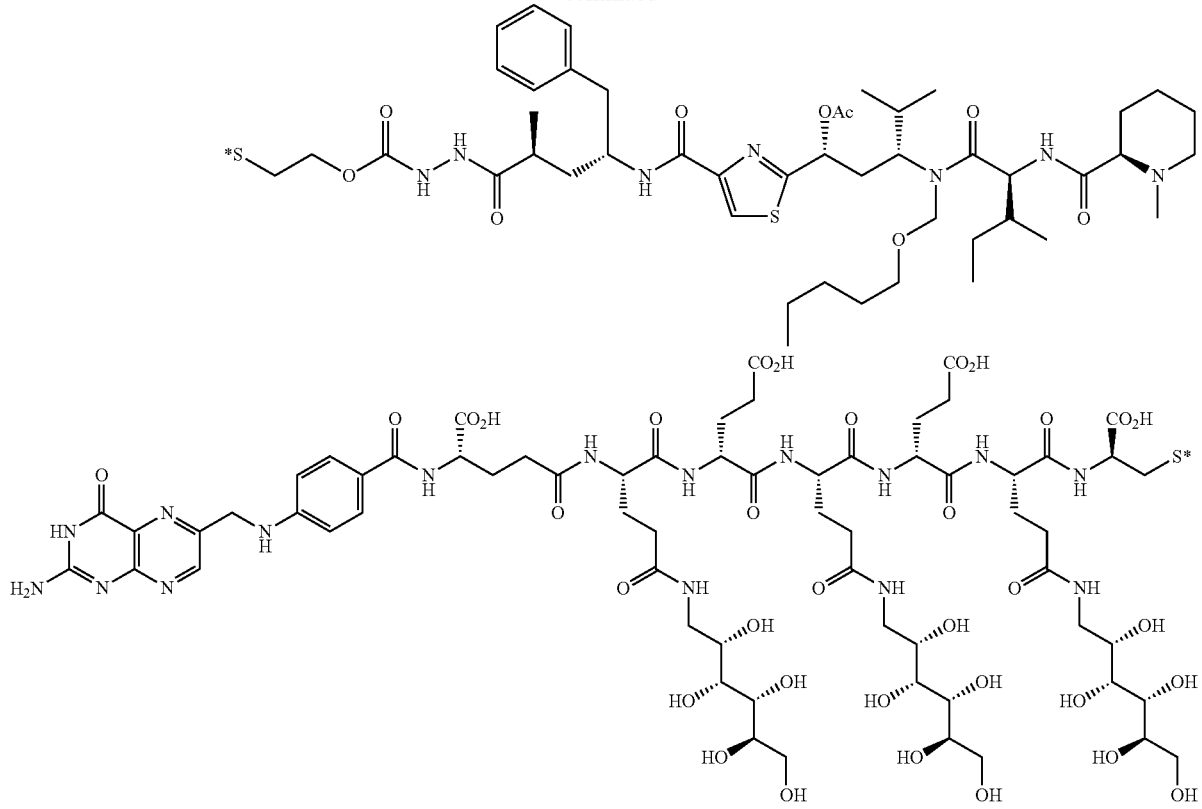

EC1997
Chemical Formula: $C_{111}H_{169}N_{23}O_{43}S_3$
Exact Mass: 2608.09
Molecular Weight: 2609.85

A solution of EC1579 (acidified, 17.0 mg, 0.01 mmole) in DMSO (0.6 mL) was mixed with 7 mg (0.067 mmole) of EC1996 in DMSO (0.2 mL) and purged with argon for 15 min. 14 μL of DIPEA (15 eq.) was added to the mixture. After 5 min., LC/MS showed complete conversion. The reaction mixture was diluted with MeOH and purified by HPLC (Mobile phase A=50 mM $NH_4HCO_3$ buffer, pH=7.0. B=ACN. Method: 5-80% B). Fractions containing the desired product were collected, combined, and freeze-dried to afford 10.5 mg (60%) of EC1997 as a pale yellow solid.

MS (ESI) $[M+2H]^{2+}=1305.86$, $[M+3H]^{3+}=870.77$.

Selected $^1$H NMR (DMSO-d6) δ(ppm) 8.62 (s, 1H), 8.17 (s, 1H), 7.62 (d, 2H), 7.17 (m, 5H), 6.61 (d, 2H), 5.80 (d, 1H), 5.23 (d, 1H), 4.49 (d, 1H), 4.45 (br, 2H), 4.43 (d, 1H), 4.30 (br, 2H), 4.17 (m, 7H), 3.50-3.65 (m, 6H), 2.05 (s, 3H, overlapped with 4H), 1.00 (d, 3H), 0.94 (d, 3H), 0.79 (t, 6H), 0.75 (t, 3H), 0.63 (d, 3H).

The following examples are prepared by the processes described herein.

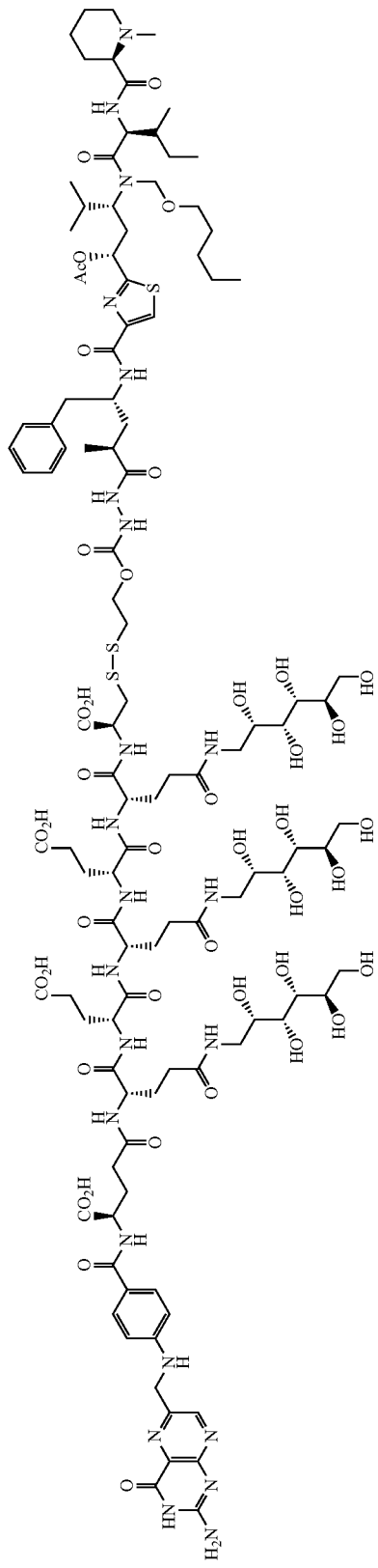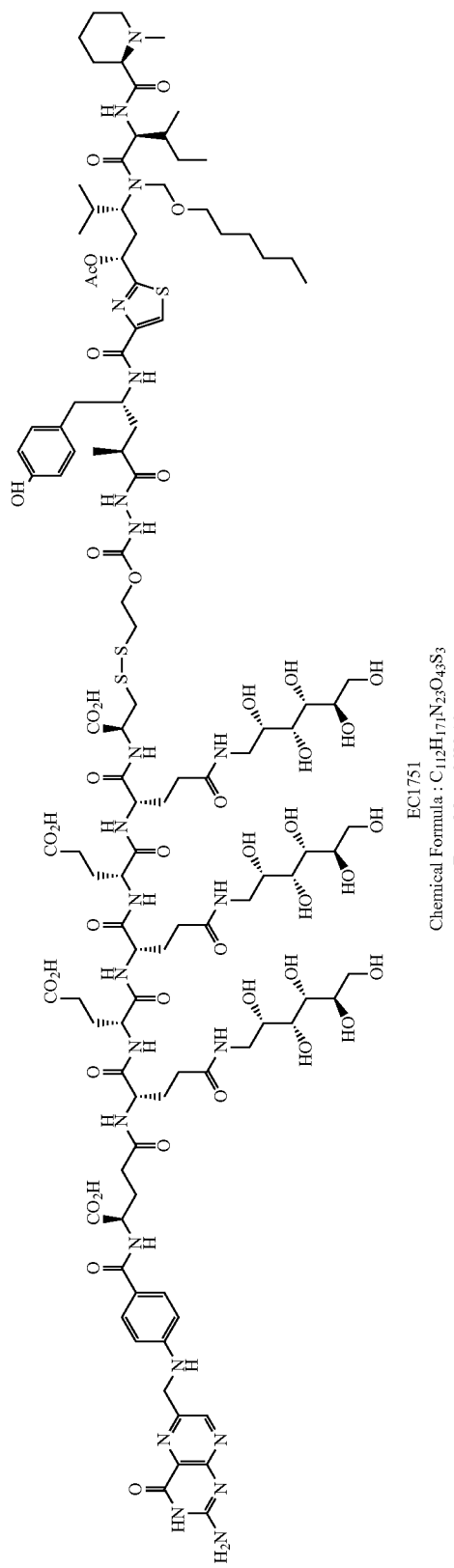

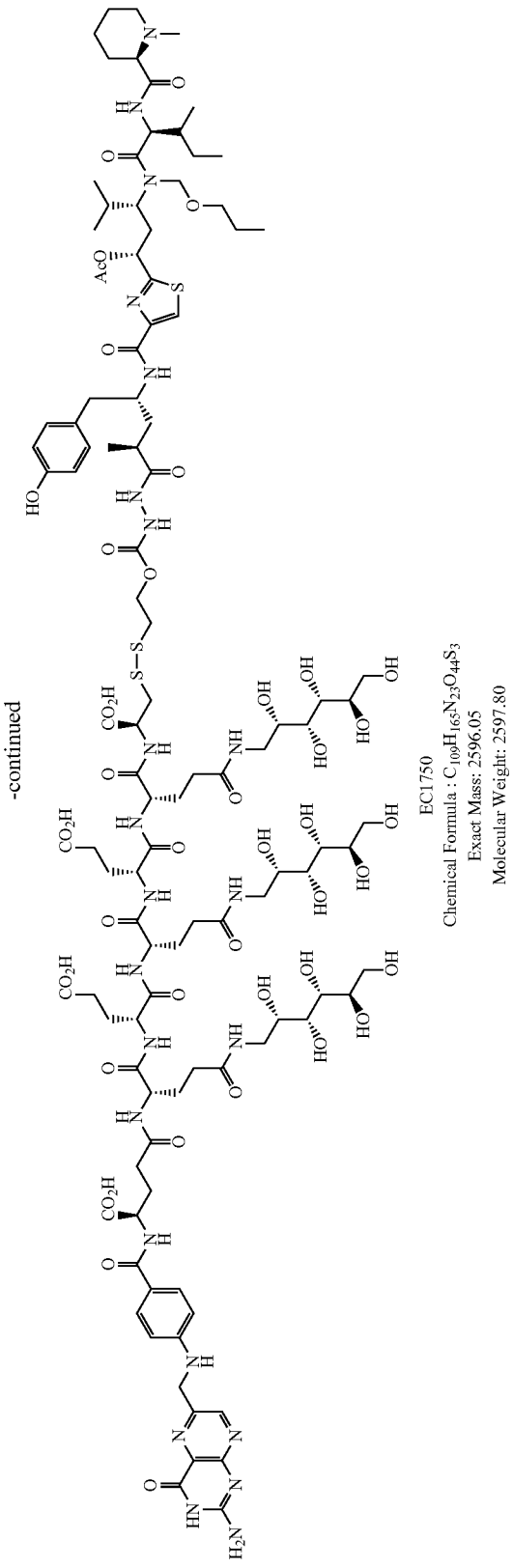
EC1750
Chemical Formula: $C_{109}H_{165}N_{23}O_{44}S_3$
Exact Mass: 2596.05
Molecular Weight: 2597.80

-continued
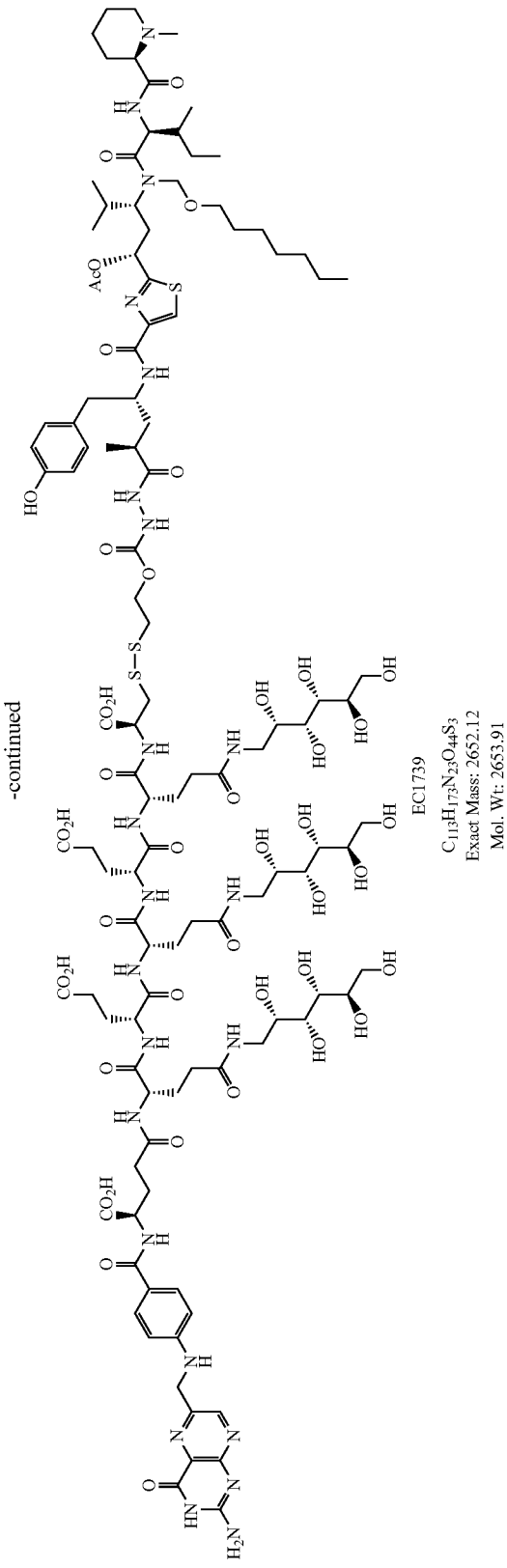
EC1739
$C_{113}H_{173}N_{23}O_{44}S_3$
Exact Mass: 2652.12
Mol. Wt: 2653.91
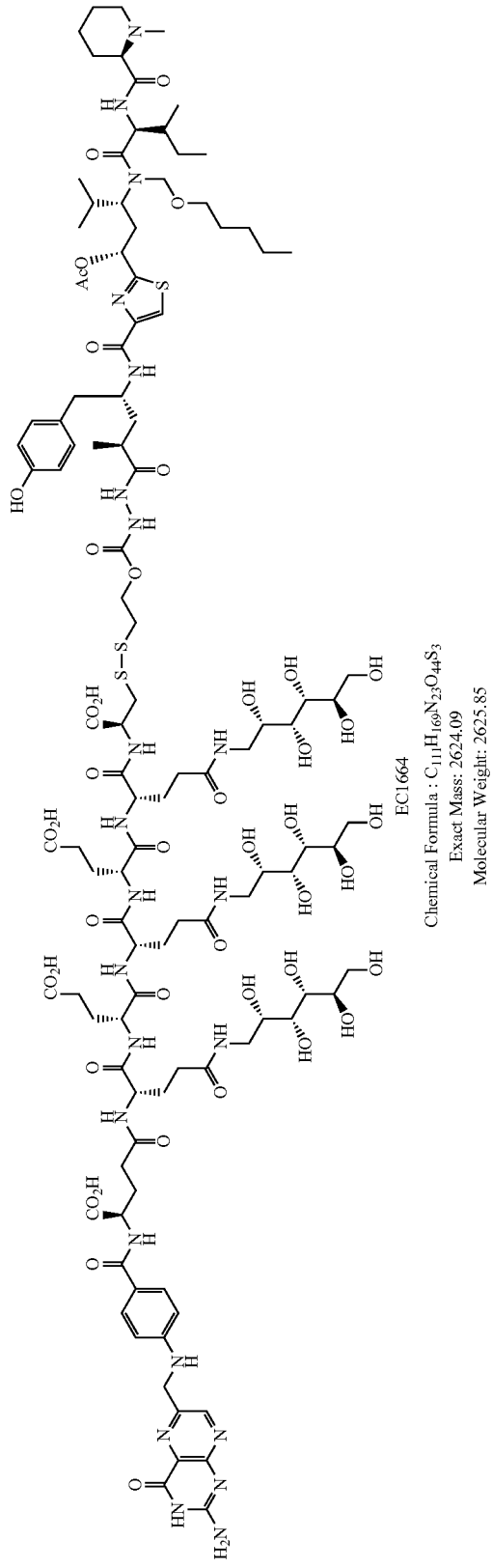
EC1664
Chemical Formula: $C_{111}H_{169}N_{23}O_{44}S_3$
Exact Mass: 2624.09
Molecular Weight: 2625.85

-continued
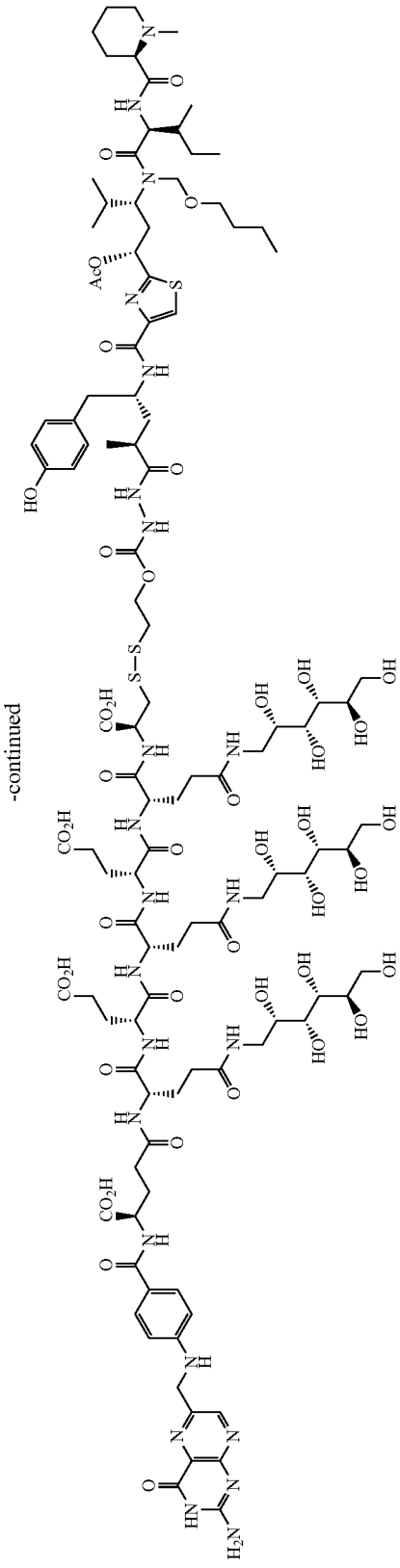
EC1663
Chemical Formula: $C_{110}H_{167}N_{23}O_{44}S_3$
Exact Mass: 2610.07
Molecular Weight: 2611.83

-continued
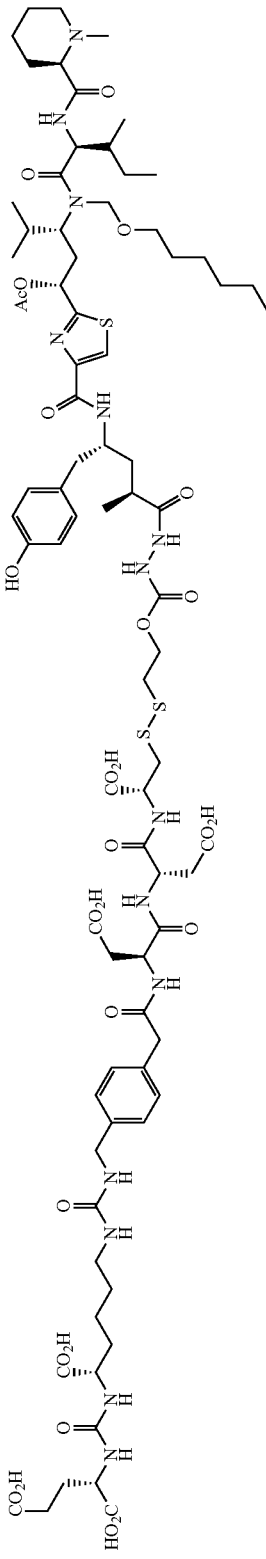
EC1721
Chemical Formula: C$_{81}$H$_{120}$N$_{14}$O$_{27}$S$_3$
Exact Mass: 1816.76
Molecular Weight: 1818.09
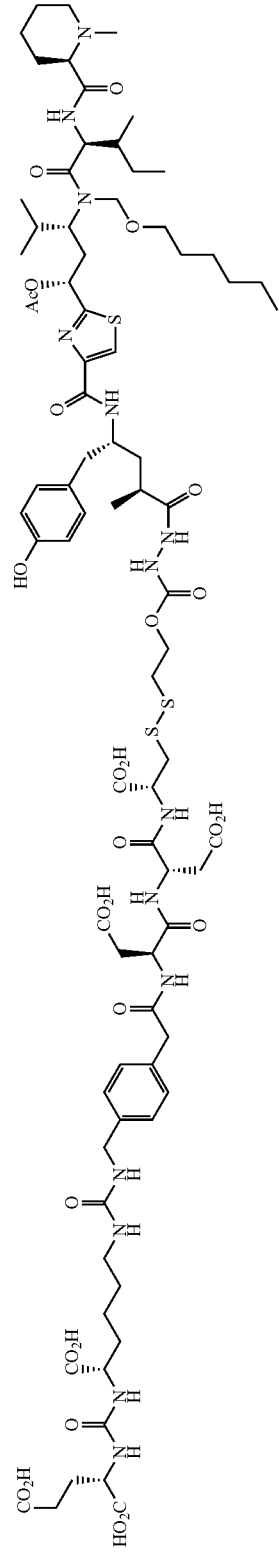
EC1720
C$_{80}$H$_{118}$N$_{14}$O$_{27}$S$_3$
Exact Mass: 1802.75
Mol. Wt.: 1804.07

-continued
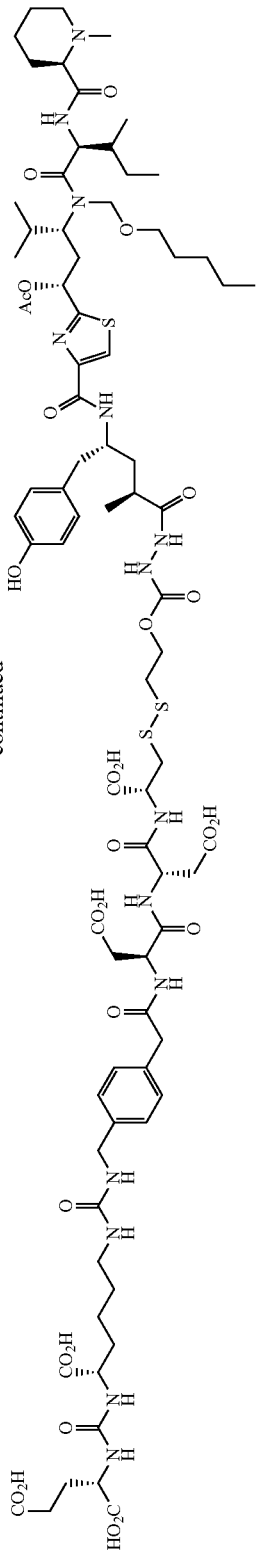
EC1719
C79H116N14O27S3
Exact Mass: 1788.73
Mol. Wt.: 1790.04
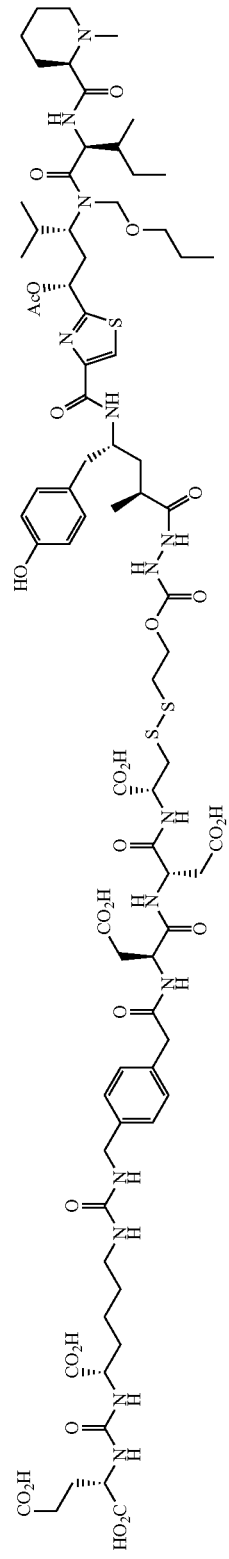
EC1718
C77H112N14O27S3
Exact Mass: 1760.70
Mol. Wt.: 1761.99

-continued
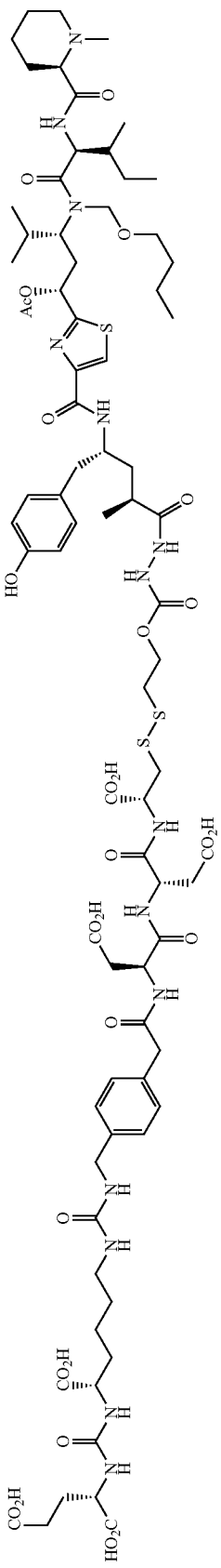
EC1677
Chemical Formula: $C_{78}H_{114}N_{14}O_{27}S_3$
Exact Mass: 1774.71
Molecular Weight: 1776.01

What is claimed is:

1. A process for preparing a compound of the formula

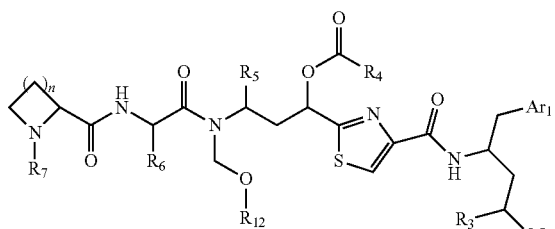
(TE)

or a pharmaceutically acceptable salt thereof; wherein
$Ar_1$ is optionally substituted aryl or optionally substituted heteroaryl;
$R_1$ is hydrogen, optionally substituted alkyl, optionally substituted arylalkyl
$R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted;
$R_3$ is optionally substituted alkyl;
$R_4$ is optionally substituted alkyl or optionally substituted cycloalkyl;
$R_5$ and $R_6$ are each independently selected from the group consisting of optionally substituted alkyl and optionally substituted cycloalkyl;
$R_7$ is hydrogen or optionally substituted alkyl; and
n is 1, 2, 3, or 4;
comprising
(a) treating a compound of formula B

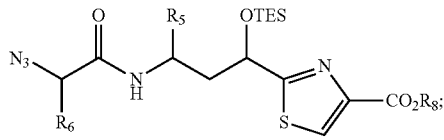
B wherein
$R_5$ and $R_6$ are each independently selected from the group consisting of optionally substituted alkyl and optionally substituted cycloalkyl; and
$R_8$ is $C_1$-$C_6$ unbranched alkyl or arylalkyl, each of which is optionally substituted; with a base and a compound of the formula $YCH_2OR_{12}$, where Y is chloro, bromo, or iodo; and
$R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted;
to provide a compound of the formula CE

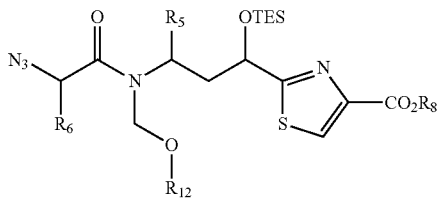
CE wherein
$R_5$ and $R_6$ are each independently selected from the group consisting of optionally substituted alkyl and optionally substituted cycloalkyl;
$R_8$ is $C_1$-$C_6$ unbranched alkyl or arylalkyl, each of which is optionally substituted; and
$R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted;
or
(b) mixing a compound of formula CE

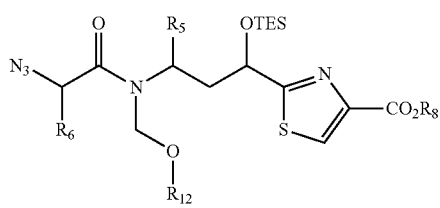
CE wherein
$R_5$ and $R_6$ are each independently selected from the group consisting of optionally substituted alkyl and optionally substituted cycloalkyl;
$R_8$ is $C_1$-$C_6$ unbranched alkyl or arylalkyl, each of which is optionally substituted; and
$R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted;
under reducing conditions with the compound of formula E1

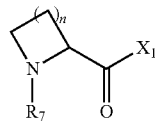
E1 wherein
$X_1$ is a leaving group;
$R_7$ is hydrogen or optionally substituted alkyl; and
n is 1, 2, 3, or 4;
to provide a compound of the formula DE

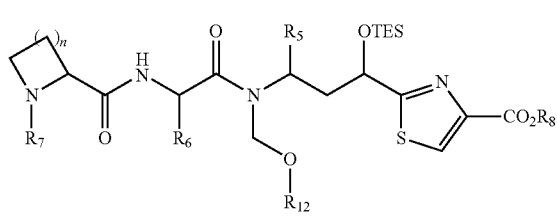
DE wherein
$R_5$ and $R_6$ are each independently selected from the group consisting of optionally substituted alkyl and optionally substituted cycloalkyl;
$R_7$ is hydrogen or optionally substituted alkyl;
$R_8$ is $C_1$-$C_6$ unbranched alkyl or arylalkyl, each of which is optionally substituted;

$R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted; and n is 1, 2, 3, or 4; or (c) treating a compound of the formula DE

DE wherein $R_5$ and $R_6$ are each independently selected from the group consisting of optionally substituted alkyl and optionally substituted cycloalkyl;

$R_7$ is hydrogen or optionally substituted alkyl;

$R_8$ is $C_1$-$C_6$ unbranched alkyl or arylalkyl, each of which is optionally substituted;

$R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted; and n is 1, 2, 3, or 4;

with a base to provide a compound of the formula IE

IE wherein $R_5$ and $R_6$ are each independently selected from the group consisting of optionally substituted alkyl and optionally substituted cycloalkyl;

$R_7$ is hydrogen or optionally substituted alkyl;

$R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted;

n is 1, 2, 3, or 4; or (d) contacting a compound of the formula D

D wherein $R_2$ is selected from the group consisting of optionally substituted alkyl, optionally substituted cycloalkyl, optionally substituted arylalkyl, and optionally substituted heteroarylalkyl;

$R_5$ and $R_6$ are each independently selected from the group consisting of optionally substituted alkyl and optionally substituted cycloalkyl;

$R_7$ is hydrogen or optionally substituted alkyl;

$R_8$ is $C_1$-$C_6$ unbranched alkyl or arylalkyl, each of which is optionally substituted; and n is 1, 2, 3, or 4;

with an alcohol of the formula $R_{12}OH$, wherein $R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted, and a transesterification catalyst selected from the group consisting of trifluoroacetic acid, $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where $R_{13}$ is independently selected from alkyl, arylalkyl, aryl, or cycloalkyl, each of which is optionally substituted;

to provide a compound of the formula FE

FE $R_5$ and $R_6$ are each independently selected from the group consisting of optionally substituted alkyl and optionally substituted cycloalkyl;

$R_7$ is hydrogen or optionally substituted alkyl;

$R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted; and n is 1, 2, 3, or 4; or (e) treating a compound of the formula FE

FE $R_5$ and $R_6$ are each independently selected from the group consisting of optionally substituted alkyl and optionally substituted cycloalkyl;

$R_7$ is hydrogen or optionally substituted alkyl;

$R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted; and n is 1, 2, 3, or 4;

with a metal hydroxide or a metal carbonate to provide a compound of the formula IE

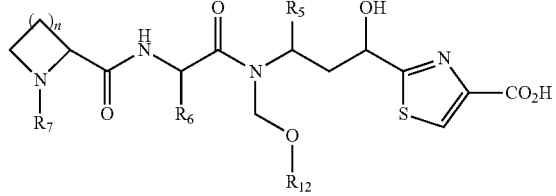

IE wherein
- $R_5$ and $R_6$ are each independently selected from the group consisting of optionally substituted alkyl and optionally substituted cycloalkyl;
- $R_7$ is hydrogen or optionally substituted alkyl;
- $R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted;
- n is 1, 2, 3, or 4; or (f) treating a compound of the formula IE

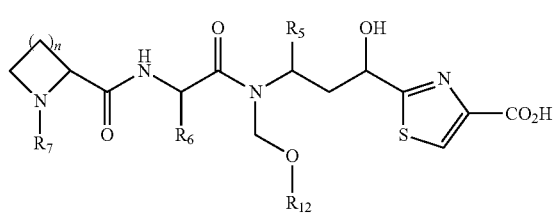

IE wherein
- $R_5$ and $R_6$ are each independently selected from the group consisting of optionally substituted alkyl and optionally substituted cycloalkyl;
- $R_7$ is hydrogen or optionally substituted alkyl;
- $R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted;
- n is 1, 2, 3, or 4;

with an acylating agent of the formula $R_4C(O)X_2$, wherein $R_4$ is optionally substituted alkyl or optionally substituted cycloalkyl; and $X_2$ is a leaving group;

to provide a compound of the formula JE

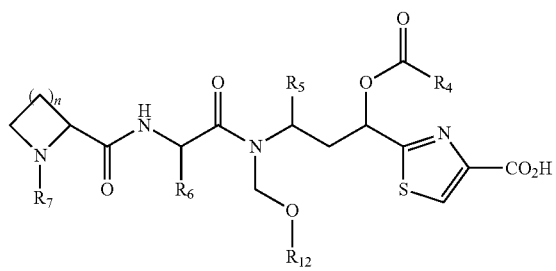

JE wherein
- $R_4$ is optionally substituted alkyl or optionally substituted cycloalkyl;
- $R_5$ and $R_6$ are each independently selected from the group consisting of optionally substituted alkyl and optionally substituted cycloalkyl;
- $R_7$ is hydrogen or optionally substituted alkyl;
- $R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted; and
- n is 1, 2, 3, or 4; or (g1) forming an active ester intermediate from a compound of formula JE

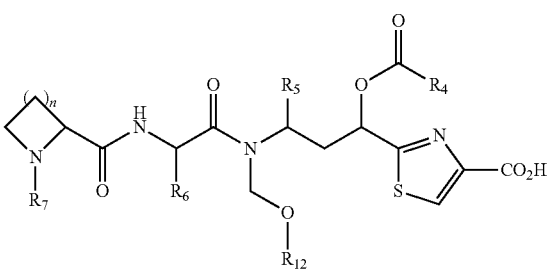

JE wherein
- $R_4$ is optionally substituted alkyl or optionally substituted cycloalkyl;
- $R_5$ and $R_6$ are each independently selected from the group consisting of optionally substituted alkyl and optionally substituted cycloalkyl;
- $R_7$ is hydrogen or optionally substituted alkyl;
- $R_{12}$ is alkyl, alkenyl, alkynyl, heteroalkyl, cycloalkyl, heterocycloalkyl, aryl, arylalkyl, heteroarylalkyl, or heteroarylalkyl, each of which is optionally substituted; and
- n is 1, 2, 3, or 4; and (g2) reacting the active ester intermediate formed in step (g1) with a compound of the formula M

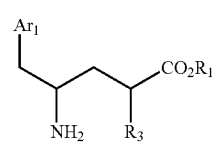

M wherein
- $Ar_1$ is optionally substituted aryl or optionally substituted heteroaryl;
- $R_1$ is hydrogen, optionally substituted alkyl, or optionally substituted arylalkyl; and
- $R_3$ is optionally substituted alkyl;

to provide a compound of the formula TE.

2. The process of claim 1, wherein the base in step (a) is potassium hexamethyldisilazane (KHMDS).

3. The process of claim 1, wherein the compound of the formula $YCH_2OR_{12}$ in step (a) is bromomethyl pentyl ether.

4. The process of claim 1, wherein the reducing conditions of step (c) comprises hydrogen gas and 10% Pd/C.

5. The process of claim 1, wherein the alcohol of step (d) is n-pentanol.

6. The process of claim 1, wherein the transesterification catalyst of step (d) is n-$Bu_2SnO$.

7. The process of claim 1, wherein the metal hydroxide or metal carbonate in step (e) is selected from the group consisting of LiOH, $Li_2CO_3$, NaOH, $Na_2CO_3$, KOH, $K_2CO_3$, $Ca(OH)_2$, $CaCO_3$, $Mg(OH)_2$ and $MgCO_3$.

8. The process of claim 1, wherein the acylating agent of step (f) of the formula $R_4C(O)X_2$ is acetic anhydride.

9. The process of claim 1, wherein $R_{12}$ is $CH_2CH=CH_2$, $CH_2CH_2CH_2CH_3$, or $CH_2CH_2CH_2CH_2CH_3$.

10. The process of claim 1, wherein $R_5$ is iso-propyl.

11. The process of claim 1, wherein $R_6$ is sec-butyl.

12. The process of claim 1, wherein $R_7$ is methyl.

13. The process of claim 1, wherein $R_3$ is methyl.

14. The process of claim 1, wherein $R_4$ is methyl.

15. The process of claim 1, wherein $Ar_1$ is phenyl or 4-hydroxyphenyl.

16. The process of claim 1, wherein $Ar_1$ is phenyl or 4-hydroxyphenyl, $R_3$ is methyl, $R_4$ is methyl, $R_5$ is iso-propyl, $R_6$ is sec-butyl, $R_7$ is methyl, and $R_{12}$ is $CH_2CH=CH_2$, $CH_2CH_2CH_2CH_3$, or $CH_2CH_2CH_2CH_2CH_3$.

* * * * *